US012564973B2

(12) United States Patent  
Devengenzo et al.

(10) Patent No.: US 12,564,973 B2  
(45) Date of Patent: Mar. 3, 2026

(54) TELESCOPING ROBOT

(71) Applicant: Neptune Medical Inc., Burlingame, CA (US)

(72) Inventors: Roman Devengenzo, San Jose, CA (US); Spencer J. Witte, San Francisco, CA (US); Neal Tanner, Austin, TX (US); Aren Hill, Mountain View, CA (US)

(73) Assignee: Neptune Medical Inc., Burlingame, CA (US)

( * ) Notice: Subject to any disclaimer, the term of this patent is extended or adjusted under 35 U.S.C. 154(b) by 0 days.

(21) Appl. No.: 19/210,595

(22) Filed: May 16, 2025

(65) Prior Publication Data

US 2025/0276456 A1 Sep. 4, 2025

Related U.S. Application Data

(63) Continuation of application No. 18/902,906, filed on Sep. 30, 2024, now Pat. No. 12,330,292.

(60) Provisional application No. 63/586,398, filed on Sep. 28, 2023.

(51) Int. Cl.
  *A61B 1/00* (2006.01)
  *B25J 18/02* (2006.01)
(52) U.S. Cl.
  CPC ......... *B25J 18/025* (2013.01); *A61B 1/00149* (2013.01); *A61B 1/00154* (2013.01)
(58) Field of Classification Search
  CPC . A61B 1/00149; A61B 1/00154; B25J 18/025
  See application file for complete search history.

(56) References Cited

U.S. PATENT DOCUMENTS

| | | | |
|---|---|---|---|
| 2,268,321 | A | 12/1941 | Flynn |
| 2,767,705 | A | 10/1956 | Moore |
| 3,466,220 | A | 9/1969 | Allinikov et al. |
| 3,859,986 | A | 1/1975 | Okada et al. |

(Continued)

FOREIGN PATENT DOCUMENTS

| | | | |
|---|---|---|---|
| AU | 2013207571 B2 | 8/2013 | |
| CN | 2613655 Y | 4/2004 | |

(Continued)

OTHER PUBLICATIONS

Tilson et al.; U.S. Appl. No. 19/223,003 entitled "Devices and methods for enhanced visualization of body lumen," filed Feb. 3, 2025.

(Continued)

*Primary Examiner* — Timothy J Neal  
(74) *Attorney, Agent, or Firm* — Shay Glenn LLP

(57) ABSTRACT

Apparatuses and methods for deploying and/or controlling movement of flexible tubular members such as endoscopes, using a sliding link assembly to support the flexible tubular member. For example, these apparatuses may include a base, a link assembly connected to the base and comprising: a plurality of links that are vertically adjacent to each other, in which adjacent pairs of links are each slidably coupled together by opposing flexible bands that extend around a cylindrical surface of a shuttle. A linear drive may drive extension and retraction of the links by engaging with just one shuttle of the link assembly.

25 Claims, 39 Drawing Sheets

(56)                References Cited

U.S. PATENT DOCUMENTS

| | | | |
|---|---|---|---|
| 3,998,216 A | 12/1976 | Hosono |
| 4,066,071 A | 1/1978 | Nagel |
| 4,141,364 A | 2/1979 | Schultze |
| 4,151,800 A | 5/1979 | Dotts et al. |
| 4,160,451 A | 7/1979 | Chittenden |
| 4,176,662 A | 12/1979 | Frazer |
| 4,425,919 A | 1/1984 | Alston, Jr |
| 4,551,140 A | 11/1985 | Shinohara |
| 4,690,131 A | 9/1987 | Lyddy, Jr. et al. |
| 4,696,544 A | 9/1987 | Costella |
| 4,717,379 A | 1/1988 | Ekholmer |
| 4,794,412 A | 12/1988 | Casey et al. |
| 4,794,912 A | 1/1989 | Lia |
| 4,815,450 A | 3/1989 | Patel |
| 4,817,613 A | 4/1989 | Jaraczewski et al. |
| 4,890,602 A | 1/1990 | Hake |
| 4,893,613 A | 1/1990 | Hake |
| 4,913,369 A | 4/1990 | Lia et al. |
| 4,959,058 A | 9/1990 | Michelson |
| 4,961,738 A | 10/1990 | Mackin |
| 4,967,732 A | 11/1990 | Inoue |
| 5,018,436 A | 5/1991 | Evangelista et al. |
| 5,019,121 A | 5/1991 | Krauter |
| 5,037,386 A | 8/1991 | Marcus et al. |
| 5,037,404 A | 8/1991 | Gold et al. |
| 5,050,585 A | 9/1991 | Takahashi |
| 5,105,819 A | 4/1992 | Wollschlager et al. |
| 5,123,421 A | 6/1992 | Sinofsky |
| 5,125,143 A | 6/1992 | Takahashi |
| 5,174,276 A | 12/1992 | Crockard |
| 5,188,595 A | 2/1993 | Jacobi |
| 5,193,525 A | 3/1993 | Silverstein et al. |
| 5,201,908 A | 4/1993 | Jones |
| 5,251,611 A | 10/1993 | Zehel et al. |
| 5,337,733 A | 8/1994 | Bauerfeind et al. |
| 5,360,440 A | 11/1994 | Andersen |
| 5,447,148 A | 9/1995 | Oneda et al. |
| 5,496,292 A | 3/1996 | Burnham |
| 5,531,685 A | 7/1996 | Hemmer et al. |
| 5,531,719 A | 7/1996 | Takahashi |
| 5,577,992 A | 11/1996 | Chiba et al. |
| 5,601,588 A | 2/1997 | Tonomura et al. |
| 5,603,991 A | 2/1997 | Kupiecki et al. |
| 5,607,435 A | 3/1997 | Sachdeva et al. |
| 5,624,381 A | 4/1997 | Kieturakis |
| 5,632,734 A | 5/1997 | Galel et al. |
| 5,637,075 A | 6/1997 | Kikawada |
| 5,662,587 A | 9/1997 | Grundfest et al. |
| 5,662,621 A | 9/1997 | Lafontaine |
| 5,746,692 A | 5/1998 | Bacich et al. |
| 5,749,828 A | 5/1998 | Solomon et al. |
| 5,759,151 A | 6/1998 | Sturges |
| 5,779,624 A | 7/1998 | Chang |
| 5,782,811 A | 7/1998 | Samson et al. |
| 5,823,961 A | 10/1998 | Fields et al. |
| 5,882,347 A | 3/1999 | Laan et al. |
| 5,891,112 A | 4/1999 | Samson |
| 5,891,114 A | 4/1999 | Chin et al. |
| 5,906,591 A | 5/1999 | Dario et al. |
| 5,916,145 A | 6/1999 | Chu et al. |
| 5,916,147 A | 6/1999 | Boury |
| 5,951,539 A | 9/1999 | Nita et al. |
| 5,976,074 A | 11/1999 | Moriyama |
| 6,090,099 A | 7/2000 | Samson et al. |
| 6,159,187 A | 12/2000 | Park et al. |
| 6,162,171 A | 12/2000 | Ng et al. |
| 6,165,123 A | 12/2000 | Thompson |
| 6,179,776 B1 | 1/2001 | Adams et al. |
| 6,190,357 B1 | 2/2001 | Ferrari et al. |
| 6,217,565 B1 | 4/2001 | Cohen |
| 6,276,661 B1 | 8/2001 | Laird |
| 6,296,644 B1 | 10/2001 | Surat et al. |
| 6,309,346 B1 | 10/2001 | Farhadi |
| 6,352,503 B1 | 3/2002 | Matsu et al. |
| 6,364,878 B1 | 4/2002 | Hall |
| 6,368,315 B1 | 4/2002 | Gillis et al. |
| 6,468,203 B2 | 10/2002 | Belson |
| 6,485,409 B1 | 11/2002 | Voloshin et al. |
| 6,503,225 B1 | 1/2003 | Kirsch et al. |
| 6,517,477 B1 | 2/2003 | Wendlandt |
| 6,547,724 B1 | 4/2003 | Soble et al. |
| 6,572,538 B2 | 6/2003 | Takase |
| 6,572,590 B1 | 6/2003 | Stevens et al. |
| 6,579,277 B1 | 6/2003 | Rabiner et al. |
| 6,610,007 B2 | 8/2003 | Belson et al. |
| 6,612,982 B1 | 9/2003 | Ouchi |
| 6,616,628 B2 | 9/2003 | Hayzelden |
| 6,620,126 B2 | 9/2003 | Unsworth et al. |
| 6,623,424 B2 | 9/2003 | Hayakawa et al. |
| 6,712,832 B2 | 3/2004 | Shah |
| 6,726,677 B1 | 4/2004 | Flaherty et al. |
| 6,730,020 B2 | 5/2004 | Peng et al. |
| 6,780,151 B2 | 8/2004 | Grabover et al. |
| 6,783,491 B2 | 8/2004 | Saadat et al. |
| 6,790,173 B2 | 9/2004 | Saadat et al. |
| 6,793,621 B2 | 9/2004 | Butler et al. |
| 6,793,661 B2 | 9/2004 | Hamilton et al. |
| 6,800,056 B2 | 10/2004 | Tartaglia et al. |
| 6,869,393 B2 | 3/2005 | Butler |
| 6,899,673 B2 | 5/2005 | Ogura et al. |
| 6,911,004 B2 | 6/2005 | Kim et al. |
| 6,923,754 B2 | 8/2005 | Lubock |
| 6,960,162 B2 | 11/2005 | Saadat et al. |
| 6,974,411 B2 | 12/2005 | Belson |
| 6,984,203 B2 | 1/2006 | Tartaglia et al. |
| 7,060,199 B2 | 6/2006 | Woydt et al. |
| 7,172,552 B2 | 2/2007 | Wendlandt |
| 7,214,230 B2 | 5/2007 | Brock et al. |
| 7,273,469 B1 | 9/2007 | Chan et al. |
| 7,288,101 B2 | 10/2007 | Deem et al. |
| 7,291,127 B2 | 11/2007 | Eidenschink |
| 7,354,427 B2 | 4/2008 | Fangrow |
| 7,365,509 B2 | 4/2008 | Park et al. |
| 7,438,712 B2 | 10/2008 | Chouinard |
| 7,511,733 B2 | 3/2009 | Takizawa et al. |
| 7,537,562 B2 | 5/2009 | Takano |
| 7,559,916 B2 | 7/2009 | Smith et al. |
| 7,591,782 B2 | 9/2009 | Fujikura |
| 7,598,652 B2 | 10/2009 | Kornbluh et al. |
| 7,658,738 B2 | 2/2010 | Nobis et al. |
| 7,695,428 B2 | 4/2010 | Machida |
| 7,736,323 B2 | 6/2010 | Von Weymarn-Scharli |
| 7,749,196 B2 | 7/2010 | Osborne et al. |
| 7,837,615 B2 | 11/2010 | Le et al. |
| 7,850,725 B2 | 12/2010 | Vardi et al. |
| 7,901,347 B2 | 3/2011 | Sekiguchi et al. |
| 7,909,755 B2 | 3/2011 | Itoi |
| 7,918,819 B2 | 4/2011 | Karmarkar et al. |
| 7,918,845 B2 | 4/2011 | Saadat et al. |
| 7,931,661 B2 | 4/2011 | Saadat et al. |
| 7,935,047 B2 | 5/2011 | Yoshida et al. |
| 7,947,000 B2 | 5/2011 | Vargas et al. |
| 7,957,790 B2 | 6/2011 | Kleen |
| 7,970,455 B2 | 6/2011 | Zilberstein et al. |
| 7,988,621 B2 | 8/2011 | Smith et al. |
| 8,047,236 B2 | 11/2011 | Perry |
| 8,075,476 B2 | 12/2011 | Vargas |
| 8,092,374 B2 | 1/2012 | Smith et al. |
| 8,109,953 B1 | 2/2012 | King, III et al. |
| 8,123,739 B2 | 2/2012 | McQueen et al. |
| 8,125,755 B2 | 2/2012 | Garcia et al. |
| 8,192,422 B2 | 6/2012 | Zubiate et al. |
| 8,206,287 B2 | 6/2012 | Matsuo |
| 8,226,548 B2 | 7/2012 | Kucklick |
| 8,241,299 B2 | 8/2012 | Hibner |
| 8,246,575 B2 | 8/2012 | Viola |
| 8,257,257 B2 | 9/2012 | Takizawa et al. |
| 8,262,677 B2 | 9/2012 | Goto |
| 8,298,161 B2 | 10/2012 | Vargas |
| 8,313,014 B2 | 11/2012 | Bettuchi |
| 8,361,090 B2 | 1/2013 | Belson |
| 8,366,606 B2 | 2/2013 | Watanabe et al. |
| 8,388,519 B2 | 3/2013 | Garcia et al. |
| 8,439,825 B2 | 5/2013 | Sekiguchi |

(56)                  References Cited

U.S. PATENT DOCUMENTS

| | | |
|---|---|---|
| 8,460,179 B2 | 6/2013 | Ikeda et al. |
| 8,485,968 B2 | 7/2013 | Welmer et al. |
| 8,496,648 B2 | 7/2013 | Rogers |
| 8,506,479 B2 | 8/2013 | Piskun et al. |
| 8,517,923 B2 | 8/2013 | Belson et al. |
| 8,545,491 B2 | 10/2013 | Abboud et al. |
| 8,550,989 B2 | 10/2013 | Dohi et al. |
| 8,556,804 B2 | 10/2013 | Smith et al. |
| 8,663,096 B2 | 3/2014 | Viola |
| 8,663,196 B2 | 3/2014 | Kassab et al. |
| 8,708,894 B2 | 4/2014 | Smith et al. |
| 8,721,530 B2 | 5/2014 | Ohline et al. |
| 8,753,312 B2 | 6/2014 | Bowe et al. |
| 8,777,844 B1 | 7/2014 | Sadanand |
| 8,920,369 B2 | 12/2014 | Salahieh et al. |
| 8,969,639 B2 | 3/2015 | Xu et al. |
| 8,992,420 B2 | 3/2015 | Maahs et al. |
| 9,011,318 B2 | 4/2015 | Choset et al. |
| 9,066,655 B2 | 6/2015 | Stefanchik et al. |
| 9,114,228 B2 | 8/2015 | Zook et al. |
| 9,125,653 B2 | 9/2015 | Kovach |
| 9,155,451 B2 | 10/2015 | Smith et al. |
| 9,192,284 B2 | 11/2015 | Hirsch et al. |
| 9,192,288 B2 | 11/2015 | Okaniwa |
| 9,211,140 B2 | 12/2015 | Lauryssen et al. |
| 9,220,398 B2 | 12/2015 | Woodley et al. |
| 9,226,825 B2 | 1/2016 | Starksen et al. |
| 9,241,611 B2 | 1/2016 | Konno |
| 9,254,123 B2 | 2/2016 | Alvarez et al. |
| 9,282,993 B1 | 3/2016 | Cohen et al. |
| 9,295,511 B2 | 3/2016 | Smith et al. |
| 9,333,287 B2 | 5/2016 | Nitsan et al. |
| 9,358,073 B2 | 6/2016 | Piligian et al. |
| 9,364,955 B2 | 6/2016 | Oyola et al. |
| 9,386,910 B2 | 7/2016 | West |
| 9,498,108 B1 | 11/2016 | Lombardi |
| 9,498,198 B2 | 11/2016 | Hu et al. |
| 9,505,125 B2 | 11/2016 | Zubiate et al. |
| 9,585,546 B2 | 3/2017 | Surti et al. |
| 9,610,068 B2 | 4/2017 | Kappel et al. |
| 9,649,473 B2 | 5/2017 | Gregorich et al. |
| 9,763,562 B2 | 9/2017 | Avitsian et al. |
| 9,814,372 B2 | 11/2017 | Smith et al. |
| 9,913,570 B2 | 3/2018 | Kucharski et al. |
| 9,937,324 B2 | 4/2018 | Kim et al. |
| 9,993,142 B2 | 6/2018 | Salman et al. |
| 10,092,291 B2 | 10/2018 | Voegele et al. |
| 10,307,042 B2 | 6/2019 | Lombardi |
| 10,463,495 B2 | 11/2019 | Rogers et al. |
| 10,625,413 B1 | 4/2020 | McPherson |
| 11,006,975 B1 | 5/2021 | Cohen et al. |
| 11,020,214 B2 | 6/2021 | Gupta et al. |
| 11,122,971 B2 | 9/2021 | Tilson et al. |
| 11,135,398 B2 | 10/2021 | Tilson et al. |
| 11,219,351 B2 | 1/2022 | Tilson et al. |
| 11,478,608 B2 | 10/2022 | Tilson et al. |
| 11,554,248 B1 | 1/2023 | Tilson et al. |
| 11,724,065 B2 | 8/2023 | Tilson et al. |
| 11,744,443 B2 | 9/2023 | Lopez et al. |
| 11,793,392 B2 | 10/2023 | Tilson et al. |
| 11,937,778 B2 | 3/2024 | Tilson et al. |
| 11,944,277 B2 | 4/2024 | Tilson et al. |
| 12,059,128 B2 | 8/2024 | Tilson et al. |
| 12,082,776 B2 | 9/2024 | Tilson et al. |
| 12,102,289 B2 | 10/2024 | Tilson et al. |
| 12,121,677 B2 | 10/2024 | Gomes et al. |
| 12,193,637 B2 | 1/2025 | Tilson et al. |
| 12,285,571 B2 | 4/2025 | Tilson et al. |
| 12,295,550 B2 | 5/2025 | Tilson et al. |
| 12,311,122 B2 | 5/2025 | Tilson et al. |
| 12,324,565 B2 | 6/2025 | Tilson et al. |
| 12,329,473 B2 | 6/2025 | Tilson et al. |
| 12,330,292 B2 * | 6/2025 | Devengenzo ........ A61B 1/0016 |
| 12,336,695 B2 | 6/2025 | Tilson et al. |
| 2001/0041881 A1 | 11/2001 | Sarge et al. |
| 2002/0049423 A1 | 4/2002 | Howell et al. |
| 2002/0107478 A1 | 8/2002 | Wendlandt |
| 2002/0161355 A1 | 10/2002 | Wollschlager |
| 2003/0023259 A1 | 1/2003 | Dubrul et al. |
| 2003/0035048 A1 | 2/2003 | Shipp |
| 2003/0036748 A1 | 2/2003 | Cooper et al. |
| 2003/0083546 A1 | 5/2003 | Butler et al. |
| 2003/0122374 A1 | 7/2003 | Ouchi et al. |
| 2003/0153866 A1 | 8/2003 | Long et al. |
| 2003/0208220 A1 | 11/2003 | Worley et al. |
| 2003/0216681 A1 | 11/2003 | Zhang et al. |
| 2003/0216691 A1 | 11/2003 | Jacobson |
| 2003/0225379 A1 | 12/2003 | Schaffer et al. |
| 2004/0019252 A1 | 1/2004 | Hirata |
| 2004/0044350 A1 | 3/2004 | Martin et al. |
| 2004/0092960 A1 | 5/2004 | Abrams et al. |
| 2004/0186349 A1 | 9/2004 | Ewers et al. |
| 2004/0186350 A1 | 9/2004 | Brenneman et al. |
| 2004/0242958 A1 | 12/2004 | Fujikawa et al. |
| 2004/0243227 A1 | 12/2004 | Starksen et al. |
| 2004/0260236 A1 | 12/2004 | Manning et al. |
| 2005/0004523 A1 | 1/2005 | Osborne et al. |
| 2005/0005363 A1 | 1/2005 | Giori et al. |
| 2005/0010237 A1 | 1/2005 | Niazi |
| 2005/0085829 A1 | 4/2005 | Kraemer et al. |
| 2005/0154258 A1 | 7/2005 | Tartaglia et al. |
| 2005/0165275 A1 | 7/2005 | Von Felten et al. |
| 2005/0165366 A1 | 7/2005 | Brustad et al. |
| 2005/0203340 A1 | 9/2005 | Butler et al. |
| 2005/0261581 A1 | 11/2005 | Hughes et al. |
| 2005/0272974 A1 | 12/2005 | Iddan |
| 2005/0277966 A1 | 12/2005 | Ewers et al. |
| 2006/0041188 A1 | 2/2006 | Dirusso et al. |
| 2006/0047183 A1 | 3/2006 | Park |
| 2006/0058582 A1 | 3/2006 | Maahs et al. |
| 2006/0063973 A1 | 3/2006 | Makower et al. |
| 2006/0106285 A1 | 5/2006 | Boulais et al. |
| 2006/0129130 A1 | 6/2006 | Tal et al. |
| 2006/0178560 A1 | 8/2006 | Saadat et al. |
| 2006/0192465 A1 | 8/2006 | Kornbluh et al. |
| 2006/0199999 A1 | 9/2006 | Ikeda et al. |
| 2006/0235457 A1 | 10/2006 | Belson |
| 2006/0235458 A1 | 10/2006 | Belson |
| 2006/0258906 A1 | 11/2006 | Binmoeller |
| 2006/0264707 A1 | 11/2006 | Kinney |
| 2006/0264821 A1 | 11/2006 | Vo et al. |
| 2006/0287666 A1 | 12/2006 | Saadat et al. |
| 2007/0015965 A1 | 1/2007 | Cox et al. |
| 2007/0038025 A1 | 2/2007 | Yoshida |
| 2007/0045504 A1 | 3/2007 | Wollschlager |
| 2007/0088367 A1 | 4/2007 | Von Weymarn-Scharli |
| 2007/0100414 A1 | 5/2007 | Licata et al. |
| 2007/0106302 A1 | 5/2007 | Ortiz |
| 2007/0118015 A1 | 5/2007 | Wendlandt |
| 2007/0135803 A1 | 6/2007 | Belson |
| 2007/0137371 A1 * | 6/2007 | Devengenzo .......... A61B 34/30 74/490.01 |
| 2007/0156018 A1 | 7/2007 | Krauter et al. |
| 2007/0219411 A1 | 9/2007 | Dejima et al. |
| 2007/0239252 A1 | 10/2007 | Hopkins et al. |
| 2007/0250113 A1 | 10/2007 | Hegeman et al. |
| 2007/0250149 A1 | 10/2007 | Depen et al. |
| 2007/0255101 A1 | 11/2007 | Or |
| 2007/0260121 A1 | 11/2007 | Bakos et al. |
| 2007/0282358 A1 | 12/2007 | Remiszewski et al. |
| 2008/0051635 A1 | 2/2008 | Tanaka et al. |
| 2008/0058722 A1 | 3/2008 | Oepen et al. |
| 2008/0091073 A1 | 4/2008 | Park |
| 2008/0103440 A1 | 5/2008 | Ferren et al. |
| 2008/0139887 A1 | 6/2008 | Fitzpatrick |
| 2008/0172037 A1 | 7/2008 | Huang et al. |
| 2008/0188928 A1 | 8/2008 | Salahleh et al. |
| 2008/0200762 A1 | 8/2008 | Stokes et al. |
| 2008/0214893 A1 | 9/2008 | Tartaglia et al. |
| 2008/0234546 A1 | 9/2008 | Kawano et al. |
| 2008/0242928 A1 | 10/2008 | Kawano et al. |
| 2008/0249362 A1 | 10/2008 | Jiang et al. |
| 2008/0262300 A1 | 10/2008 | Ewers et al. |
| 2008/0275299 A1 | 11/2008 | Park |

(56) References Cited

U.S. PATENT DOCUMENTS

| | | |
|---|---|---|
| 2009/0023983 A1 | 1/2009 | Stefanchik |
| 2009/0048483 A1 | 2/2009 | Yamamoto |
| 2009/0062611 A1 | 3/2009 | Toyama |
| 2009/0062837 A1 | 3/2009 | Gasche et al. |
| 2009/0062872 A1 | 3/2009 | Chin et al. |
| 2009/0104250 A1 | 4/2009 | Boyden et al. |
| 2009/0112063 A1 | 4/2009 | Bakos et al. |
| 2009/0112064 A1 | 4/2009 | Levey et al. |
| 2009/0131752 A1 | 5/2009 | Park |
| 2009/0157068 A1 | 6/2009 | Kallel et al. |
| 2009/0187163 A1 | 7/2009 | Uihlein |
| 2009/0240202 A1 | 9/2009 | Drasler et al. |
| 2009/0248041 A1 | 10/2009 | Williams et al. |
| 2009/0259200 A1 | 10/2009 | Lampropoulos et al. |
| 2009/0264704 A1 | 10/2009 | Shtul |
| 2010/0010308 A1 | 1/2010 | Braun et al. |
| 2010/0010437 A1 | 1/2010 | Miles et al. |
| 2010/0010504 A1 | 1/2010 | Simaan et al. |
| 2010/0016663 A1 | 1/2010 | Maisch et al. |
| 2010/0036363 A1 | 2/2010 | Watanabe et al. |
| 2010/0069712 A1 | 3/2010 | Yamaya |
| 2010/0069716 A1 | 3/2010 | Chin et al. |
| 2010/0076451 A1 | 3/2010 | Zwolinski et al. |
| 2010/0087711 A1 | 4/2010 | Edwards |
| 2010/0137686 A1 | 6/2010 | Meron et al. |
| 2010/0145151 A1 | 6/2010 | Fukunaga et al. |
| 2010/0160735 A1 | 6/2010 | Bakos |
| 2010/0185172 A1 | 7/2010 | Fabro |
| 2010/0204546 A1 | 8/2010 | Hassidov et al. |
| 2010/0268025 A1 | 10/2010 | Belson |
| 2010/0331625 A1 | 12/2010 | Rosemurgy et al. |
| 2010/0331820 A1 | 12/2010 | Prisco et al. |
| 2011/0015729 A1 | 1/2011 | Jimenez et al. |
| 2011/0023888 A1 | 2/2011 | Vazales et al. |
| 2011/0040282 A1 | 2/2011 | Uihlein |
| 2011/0046442 A1 | 2/2011 | Matsushita |
| 2011/0049282 A1 | 3/2011 | Danielsson |
| 2011/0054253 A1 | 3/2011 | Jordá Albiñana et al. |
| 2011/0087070 A1 | 4/2011 | Tilson et al. |
| 2011/0237888 A1 | 9/2011 | Matsushita |
| 2011/0245611 A1 | 10/2011 | Yeh et al. |
| 2011/0245858 A1 | 10/2011 | Milsorn et al. |
| 2011/0282149 A1 | 11/2011 | Vargas et al. |
| 2011/0288553 A1 | 11/2011 | Jansen et al. |
| 2011/0301414 A1 | 12/2011 | Hotto et al. |
| 2011/0306950 A1 | 12/2011 | Cucin |
| 2011/0319714 A1 | 12/2011 | Roelle et al. |
| 2012/0004676 A1 | 1/2012 | Vargas |
| 2012/0022329 A1 | 1/2012 | Wagh et al. |
| 2012/0041291 A1 | 2/2012 | Ferren et al. |
| 2012/0095448 A1 | 4/2012 | Kaji |
| 2012/0095548 A1 | 4/2012 | Gregorich et al. |
| 2012/0108902 A1 | 5/2012 | Frassica et al. |
| 2012/0130173 A1 | 5/2012 | Lutze et al. |
| 2012/0143005 A1 | 6/2012 | Yeh et al. |
| 2012/0165607 A1 | 6/2012 | Ashida et al. |
| 2012/0165792 A1 | 6/2012 | Ortiz et al. |
| 2012/0172651 A1 | 7/2012 | Cutrer |
| 2012/0209062 A1 | 8/2012 | Qiao |
| 2012/0209292 A1 | 8/2012 | Devengenzo et al. |
| 2012/0277528 A1 | 11/2012 | Qiao |
| 2012/0277729 A1 | 11/2012 | Melsheimer |
| 2013/0131641 A1 | 5/2013 | Jimenez et al. |
| 2013/0190565 A1 | 7/2013 | Gora et al. |
| 2013/0274553 A1 | 10/2013 | Piskun |
| 2013/0304179 A1 | 11/2013 | Bialas et al. |
| 2013/0333472 A1 | 12/2013 | Georgeson |
| 2013/0338440 A1 | 12/2013 | Sinai et al. |
| 2014/0005683 A1 | 1/2014 | Stand et al. |
| 2014/0073853 A1 | 3/2014 | Swisher et al. |
| 2014/0081169 A1 | 3/2014 | Gerding et al. |
| 2014/0088459 A1 | 3/2014 | Roush et al. |
| 2014/0142393 A1 | 5/2014 | Piskun et al. |
| 2014/0155702 A1 | 6/2014 | Tilson et al. |
| 2014/0155783 A1 | 6/2014 | Starksen et al. |
| 2014/0188054 A1 | 7/2014 | Iijima et al. |
| 2014/0234600 A1 | 8/2014 | Wang et al. |
| 2014/0243796 A1 | 8/2014 | Tegg et al. |
| 2014/0243873 A1 | 8/2014 | Franklin |
| 2014/0275860 A1 | 9/2014 | Rottenberg et al. |
| 2014/0276601 A1 | 9/2014 | Edward |
| 2014/0276642 A1 | 9/2014 | Cully et al. |
| 2014/0309587 A1 | 10/2014 | Kim et al. |
| 2014/0343358 A1 | 11/2014 | Hameed et al. |
| 2014/0371718 A1 | 12/2014 | Alvarez et al. |
| 2014/0371764 A1 | 12/2014 | Oyola et al. |
| 2015/0018616 A1 | 1/2015 | Kumoyama |
| 2015/0038919 A1 | 2/2015 | Bramwell et al. |
| 2015/0073216 A1 | 3/2015 | Papay |
| 2015/0073342 A1 | 3/2015 | Pacheco et al. |
| 2015/0073409 A1 | 3/2015 | Watson et al. |
| 2015/0094656 A1 | 4/2015 | Salahieh et al. |
| 2015/0119640 A1 | 4/2015 | Reydel |
| 2015/0126814 A1 | 5/2015 | Mesallum et al. |
| 2015/0133729 A1 | 5/2015 | Reydel |
| 2015/0142013 A1 | 5/2015 | Tanner et al. |
| 2015/0148602 A1 | 5/2015 | Hill et al. |
| 2015/0148606 A1 | 5/2015 | Rottenberg et al. |
| 2015/0164314 A1 | 6/2015 | Peterson |
| 2015/0173836 A1 | 6/2015 | Pack et al. |
| 2015/0216589 A1 | 8/2015 | Wittenberger et al. |
| 2015/0276097 A1 | 10/2015 | Carlson et al. |
| 2015/0335387 A1 | 11/2015 | Atzinger et al. |
| 2015/0342608 A1 | 12/2015 | Hernandez |
| 2015/0369325 A1 | 12/2015 | Bureau et al. |
| 2016/0007832 A1 | 1/2016 | Shimada |
| 2016/0015259 A1 | 1/2016 | Mody et al. |
| 2016/0038002 A1 | 2/2016 | Peters et al. |
| 2016/0058268 A1 | 3/2016 | Salman et al. |
| 2016/0066773 A1 | 3/2016 | Cooper et al. |
| 2016/0096004 A1 | 4/2016 | Gerrans et al. |
| 2016/0129547 A1 | 5/2016 | Duescher et al. |
| 2016/0136393 A1 | 5/2016 | Tsai et al. |
| 2016/0174829 A1 | 6/2016 | Reydel |
| 2016/0198935 A1 | 7/2016 | Choi et al. |
| 2016/0206425 A1 | 7/2016 | Madrid et al. |
| 2016/0270870 A1 | 9/2016 | Kowshik |
| 2016/0279388 A1 | 9/2016 | Barrish et al. |
| 2016/0287059 A1 | 10/2016 | Ha et al. |
| 2016/0324412 A1 | 11/2016 | Hassidov et al. |
| 2017/0023154 A1 | 1/2017 | Jaeker et al. |
| 2017/0156567 A1 | 6/2017 | Kaneko |
| 2017/0157363 A1 | 6/2017 | Barrish et al. |
| 2017/0312920 A1 | 11/2017 | Yip et al. |
| 2017/0333681 A1 | 11/2017 | Di Caprio et al. |
| 2017/0340862 A1 | 11/2017 | Calabrese et al. |
| 2017/0360281 A1 | 12/2017 | Ponsky |
| 2018/0015257 A1 | 1/2018 | Krolik et al. |
| 2018/0043134 A1 | 2/2018 | Alvarez et al. |
| 2018/0064366 A1 | 3/2018 | Sweeney et al. |
| 2018/0085559 A1 | 3/2018 | Laby et al. |
| 2018/0126144 A1 | 5/2018 | Furnish et al. |
| 2018/0132705 A1 | 5/2018 | Higuchi |
| 2018/0184885 A1 | 7/2018 | St. George |
| 2018/0249893 A1 | 9/2018 | Yeung et al. |
| 2018/0256876 A1 | 9/2018 | Furnish et al. |
| 2018/0263469 A1 | 9/2018 | Okaniwa et al. |
| 2018/0264239 A1 | 9/2018 | Piskun |
| 2018/0289925 A1 | 10/2018 | Palmer et al. |
| 2018/0326197 A1 | 11/2018 | McArthur et al. |
| 2018/0361116 A1 | 12/2018 | Quick et al. |
| 2018/0374603 A1 | 12/2018 | Greenwood |
| 2019/0046012 A1 | 2/2019 | Ikeda |
| 2019/0175799 A1 | 6/2019 | Hsu et al. |
| 2019/0226447 A1 | 7/2019 | Stecher et al. |
| 2019/0247050 A1 | 8/2019 | Goldsmith |
| 2020/0022712 A1 | 1/2020 | Deville et al. |
| 2020/0030575 A1 | 1/2020 | Bogusky et al. |
| 2020/0100653 A1 | 4/2020 | Nakamura |
| 2020/0171276 A1 | 6/2020 | Onozuka |
| 2020/0230808 A1 | 7/2020 | Simaan et al. |
| 2020/0237198 A1 | 7/2020 | Liu et al. |
| 2020/0315429 A1 | 10/2020 | Russo et al. |
| 2020/0315433 A1 | 10/2020 | Axon et al. |

(56)  References Cited

U.S. PATENT DOCUMENTS

| | | |
|---|---|---|
| 2020/0383677 A1 | 12/2020 | Piligian et al. |
| 2020/0391002 A1 | 12/2020 | Hilton et al. |
| 2021/0000505 A1 | 1/2021 | Lenker et al. |
| 2021/0030260 A1 | 2/2021 | Julian et al. |
| 2021/0045626 A1 | 2/2021 | Hsu et al. |
| 2021/0114507 A1 | 4/2021 | Alexander et al. |
| 2021/0153965 A1 | 5/2021 | Lau et al. |
| 2021/0197684 A1 | 7/2021 | Graham et al. |
| 2021/0228973 A1 | 7/2021 | Conte |
| 2021/0323767 A1 | 10/2021 | Liu et al. |
| 2021/0330938 A1 | 10/2021 | Kendrick et al. |
| 2022/0000346 A1 | 1/2022 | Switzer |
| 2022/0087764 A1 | 3/2022 | Levinson et al. |
| 2022/0192466 A1 | 6/2022 | Nishimura |
| 2022/0347430 A1 | 11/2022 | Pedersen |
| 2023/0017488 A1 | 1/2023 | Somasundaram et al. |
| 2023/0034024 A1 | 2/2023 | Cope et al. |
| 2023/0062769 A1 | 3/2023 | Lichtenstein |
| 2023/0070264 A1 | 3/2023 | Leuthardt et al. |
| 2023/0121021 A1 | 4/2023 | Sinay et al. |
| 2023/0138203 A1 | 5/2023 | Bazdanes et al. |
| 2023/0210351 A1 | 7/2023 | Scheeff et al. |
| 2023/0338702 A1 | 10/2023 | Tilson et al. |
| 2023/0346204 A1 | 11/2023 | Tilson et al. |
| 2023/0346205 A1 | 11/2023 | Tilson et al. |
| 2023/0346399 A1 | 11/2023 | Schaller et al. |
| 2023/0353879 A1 | 11/2023 | Nishide et al. |
| 2023/0380662 A1 | 11/2023 | Slawinski et al. |
| 2023/0404486 A1 | 12/2023 | Carreel et al. |
| 2023/0404701 A1 | 12/2023 | Romo et al. |
| 2024/0016638 A1 | 1/2024 | McGowan et al. |
| 2024/0016639 A1 | 1/2024 | McGowan et al. |
| 2024/0024640 A1 | 1/2024 | Gomes et al. |
| 2024/0082557 A1 | 3/2024 | Tilson et al. |
| 2024/0090744 A1 | 3/2024 | Lopez et al. |
| 2024/0165833 A1 | 5/2024 | Tanner et al. |
| 2024/0293003 A1 | 9/2024 | Tilson et al. |
| 2024/0339112 A1 | 10/2024 | Rabinovich et al. |
| 2024/0350768 A1 | 10/2024 | Tilson et al. |
| 2024/0358232 A1 | 10/2024 | Joseph et al. |
| 2025/0031949 A1 | 1/2025 | Tilson et al. |
| 2025/0065078 A1 | 2/2025 | Morris et al. |
| 2025/0082178 A1 | 3/2025 | Witte et al. |
| 2025/0089992 A1 | 3/2025 | Tilson et al. |
| 2025/0090801 A1 | 3/2025 | Zayed et al. |
| 2025/0107697 A1 | 4/2025 | Tilson et al. |
| 2025/0107812 A1 | 4/2025 | Eisler et al. |
| 2025/0134352 A1 | 5/2025 | Tilson et al. |
| 2025/0135159 A1 | 5/2025 | Gomes et al. |
| 2025/0160620 A1 | 5/2025 | Lopez et al. |
| 2025/0160891 A1 | 5/2025 | Gomes et al. |
| 2025/0169678 A1 | 5/2025 | Tilson et al. |
| 2025/0194904 A1 | 6/2025 | Tilson et al. |
| 2025/0262407 A1 | 8/2025 | Tilson et al. |
| 2025/0281718 A1 | 9/2025 | Tilson et al. |

FOREIGN PATENT DOCUMENTS

| | | | |
|---|---|---|---|
| CN | 1706349 A | 12/2005 | |
| CN | 1732855 A | 2/2006 | |
| CN | 1764800 A | 4/2006 | |
| CN | 1806770 A | 7/2006 | |
| CN | 1861011 A | 11/2006 | |
| CN | 101119765 A | 2/2008 | |
| CN | 101129255 A | 2/2008 | |
| CN | 101888872 A | 11/2010 | |
| CN | 102137628 A | 7/2011 | |
| CN | 201899767 U | 7/2011 | |
| CN | 102711585 A | 10/2012 | |
| CN | 102872519 A | 1/2013 | |
| CN | 103384500 A | 11/2013 | |
| CN | 104168860 A | 11/2014 | |
| CN | 104287684 B | 3/2016 | |
| CN | 105759418 A | 7/2016 | |
| CN | 105813536 A | 7/2016 | |
| CN | 105832279 A | 8/2016 | |
| CN | 106137397 A | 11/2016 | |
| CN | 106455929 A | 2/2017 | |
| CN | 106488744 A | 3/2017 | |
| CN | 106659367 A | 5/2017 | |
| CN | 106823102 A | 6/2017 | |
| CN | 107296584 A | 10/2017 | |
| CN | 107697631 A | 2/2018 | |
| CN | 110077771 A | 8/2019 | |
| CN | 110582324 A | 12/2019 | |
| CN | 212558299 U | 2/2021 | |
| DE | 102005039601 A1 | 2/2007 | |
| EP | 401129 A1 | 12/1990 | |
| EP | 0941743 A2 | 9/1999 | |
| EP | 1662972 A2 | 6/2006 | |
| EP | 1695657 A1 | 8/2006 | |
| EP | 1487318 B1 | 3/2008 | |
| EP | 2016914 A2 | 1/2009 | |
| EP | 1499227 B1 | 10/2010 | |
| EP | 2258322 A2 | 12/2010 | |
| EP | 2364637 A1 | 9/2011 | |
| EP | 2368481 A1 | 9/2011 | |
| EP | 2368483 A1 | 9/2011 | |
| EP | 3256052 A1 | 12/2017 | |
| EP | 2604175 B1 | 11/2019 | |
| GB | 2482355 A | 10/2010 | |
| GB | 2497544 A | 6/2013 | |
| JP | S6289014 A | 4/1987 | |
| JP | H05220102 A | 8/1993 | |
| JP | H05293077 A | 11/1993 | |
| JP | H0644503 U | 6/1994 | |
| JP | H06335531 A | 12/1994 | |
| JP | 2002125921 A | 5/2002 | |
| JP | 2003501197 A | 1/2003 | |
| JP | 2003508133 A | 3/2003 | |
| JP | 2005152300 A | 6/2005 | |
| JP | 2005323778 A | 11/2005 | |
| JP | 2006068449 A | 3/2006 | |
| JP | 03965108 B2 | 8/2007 | |
| JP | 2009506839 A | 2/2009 | |
| JP | 2009507617 A | 2/2009 | |
| JP | 2009061173 A | 3/2009 | |
| JP | 2010000360 A | 1/2010 | |
| JP | 2011194126 A | 10/2011 | |
| JP | 2012183232 A | 9/2012 | |
| JP | 2013514150 A | 4/2013 | |
| JP | 2013176465 A | 9/2013 | |
| JP | 2014124475 A | 7/2014 | |
| JP | 2015525609 A | 9/2015 | |
| JP | 2018500054 A | 1/2018 | |
| JP | 2018514350 A | 6/2018 | |
| JP | 2018525197 A | 9/2018 | |
| JP | 2018537229 A | 12/2018 | |
| JP | 6829351 B1 | 2/2021 | |
| JP | 2021175686 A | 11/2021 | |
| KR | 10-2015-0131502 A | 11/2015 | |
| KR | 20180053852 A | 5/2018 | |
| KR | 101908933 B1 | 10/2018 | |
| WO | WO97/43941 A1 | 11/1997 | |
| WO | WO99/053827 A1 | 10/1999 | |
| WO | WO03/013348 A1 | 2/2003 | |
| WO | WO2005/110199 A1 | 11/2005 | |
| WO | WO2005/110200 A1 | 11/2005 | |
| WO | WO2007/035931 A2 | 3/2007 | |
| WO | WO2008/041809 A1 | 4/2008 | |
| WO | WO2008/122969 A1 | 10/2008 | |
| WO | WO2008/122997 A1 | 10/2008 | |
| WO | WO2009/154192 A1 | 12/2009 | |
| WO | WO2011/018147 A1 | 2/2011 | |
| WO | WO2011/018157 A1 | 2/2011 | |
| WO | WO2011/148172 A2 | 12/2011 | |
| WO | WO2012/054480 A1 | 4/2012 | |
| WO | WO2012/080947 A1 | 6/2012 | |
| WO | WO2012/122288 A2 | 9/2012 | |
| WO | WO2013/132992 A1 | 9/2013 | |
| WO | WO2016/034598 A1 | 3/2016 | |
| WO | WO2016/190324 A1 | 12/2016 | |
| WO | WO2017/041052 A1 | 3/2017 | |
| WO | WO2018/035452 A1 | 8/2017 | |

(56)  References Cited

FOREIGN PATENT DOCUMENTS

| WO | WO2019/054867 | A1 | 3/2019 |
|----|---------------|----|--------|
| WO | WO2019/160865 | A1 | 8/2019 |
| WO | WO2020/018934 | A1 | 1/2020 |
| WO | WO2020/214221 | A1 | 10/2020 |
| WO | WO2020/237426 | A1 | 12/2020 |
| WO | WO2021/202336 | A1 | 10/2021 |
| WO | WO2021/242884 | A1 | 12/2021 |
| WO | WO2022/051682 | A1 | 3/2022 |
| WO | WO2022/087093 | A1 | 4/2022 |
| WO | WO2022/146939 | A1 | 7/2022 |
| WO | WO2022/159861 | A1 | 7/2022 |
| WO | WO2023/122667 | A1 | 6/2023 |
| WO | WO2023/122767 | A2 | 6/2023 |
| WO | WO2023/133403 | A1 | 7/2023 |
| WO | WO2023/154743 | A2 | 8/2023 |
| WO | WO2023/212641 | A2 | 11/2023 |
| WO | WO2023/225520 | A2 | 11/2023 |
| WO | WO2013/184192 | A2 | 12/2023 |
| WO | WO2024/233497 | A1 | 11/2024 |
| WO | WO2025/129198 | A1 | 6/2025 |
| WO | WO2025/199177 | A1 | 9/2025 |

OTHER PUBLICATIONS

Dow, Dow white paper: Can you estimate modulus from durometer hardness for silicones: Yes, but you only roughly and you must choose your modulus carefully!; 5 pages; retrieved from the internet (https://www.dow.com/content/dam/doc/documents/en-us/tech-art/11/11-37/11-3716-01-durometer-hardness-for-silicones.pdf) on Jan. 18, 2023.

Bearing Works; PTFE Datasheet; 2 pages; Jan. 21, 2021 retrieved from the internet (https://www.bearingworks.com/uploaded-assets/pdfs/retainers/ptfe-datasheet.pdf) on Nov. 10, 2023.

Entrada® colonic overtube product brochure downloaded from internet http://www.usendoscopy.com/-/media/Files/Documents/Spec-Sheet-International/760358c_entrada_intl_ss_web.pdf Accessed Date: Jun. 5, 2017 (the year of publication is sufficiently earlier than the effective U.S. filing date and any foreign priority date so that the particular month of publication is not in issue) 2009.

Filip et al.; Design, Implementation, and Testing of a miniature self-stabilizing capsule endoscope with wireless image transmission capabilities; Inti. Journal "Information Technologies & Knowl-edge"; 5(1); downloaded from http://www.foibg.com/ijitk/ijitk-vol05/ijitk05-1-p01.pdf on Jul. 28, 2016; (the year of publication is sufficiently earlier than the effective U.S. filing date and any foreign priority date so that the particular month of publication is not in issue) 2011.

Loeve et al.; Endoscope Shaft-Rigidity Control Mechanism: "Forguide"; IEEE Trans. on Biomed. Eng.; 59(2); pp. 542-551; Feb. 2012.

Loeve et al.; Vacuum packed particles as flexible endoscope guides with controllable rigidity; Granular Matter; 12(6); pp. 543-554; Jun. 24, 2010.

Mayinger et al.; Disposable-sheath, flexible gastroscope system versus standard gastroscopes: a prospective, randomized trial; Gastrointestinal Endoscopy; 50(4); pp. 461-467; Oct. 1999.

Mayinger et al.; Disposable protection for flexible gastroenterologic endoscopy: prospective comparative evaluation of a new gastroscopy system (Endosheath) compared to the standard fiberglass gastroscope; (English Abstract Only); Zeitschrift Fur Gastrenterologia; 36(6); pp. 501-507; Jun. 1998 (Eng Abs only).

Ofstead et al.; A systematic review of disposable sheath use during flexible endoscopy; AORN Journal; 109(6); pp. 757-771; Jun. 2019.

Rothstein et al.; Disposable, sheathed, flexible sigmoidoscopy: a prospective, multicenter, randomized trial; Gastrointestinal Endoscopy; 41(6); pp. 566-572; Jun. 1995.

Sardinha et al.; Efficiency and productivity of a sheathed fiberoptic sigmoidoscope compared with a conventional sigmoidoscope; Diseases of the Colon and Rectum; 40(10); pp. 1248-1253; Oct. 1997.

Shah et al.; Magnetic Imaging of Colonoscopy: An Audit of Looping, Accuracy and Ancillary maneuvers; Gastrointest. Endosc.; 52(1); pp. 1-8; Jul. 1, 2000.

Simi et al.; Design, Fabrication, and Testing of a Capsule With Hybrid Locomotion for Gastrointestinal Tract Exploration; IEEE/ASME Trans on Mechatronics; 15(2); pp. 170-x; Apr. 2010.

Valdastri et al.; Advanced Technologies for Gastrointestinal Endoscopy; Annu. Rev. Biomed. Eng.; 14; pp. 397-429; May 2012.

Zhao et al.; Development of a variable stiffness over tube based on low-melting-point-alloy for endoscopic surgery; J. Med. Devices; 10(2); 8 pages; May 12, 2016.

Ferrante et al.; U.S. Appl. No. 18/851,053 entitled "Methods and apparatuses for navigating using a pair of rigidizing devices," filed Sep. 25, 2024.

Tilson et al.; U.S. Appl. No. 19/100,929 entitled "Dynamic rigidization methods and apparatuses," filed Feb. 3, 2025.

Tilson et al.; U.S. Appl. No. 19/210,485 entitled "Methods of attaching a rigidizing sheath to an endoscope," filed May 16, 2025.

* cited by examiner

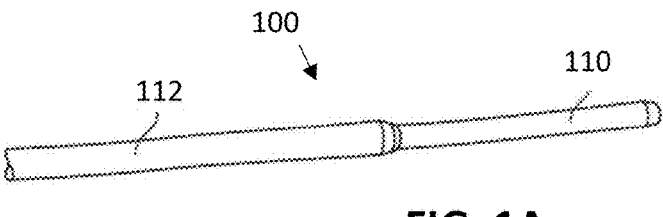
FIG. 1A
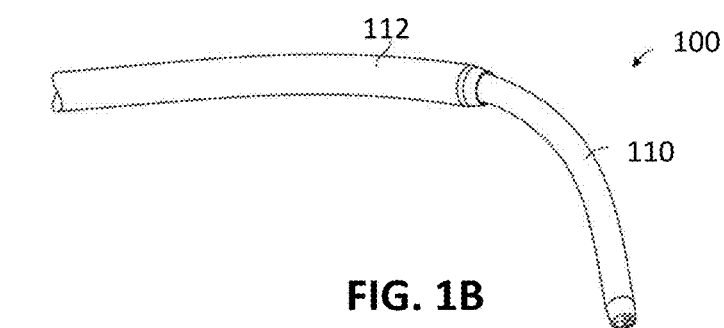
FIG. 1B
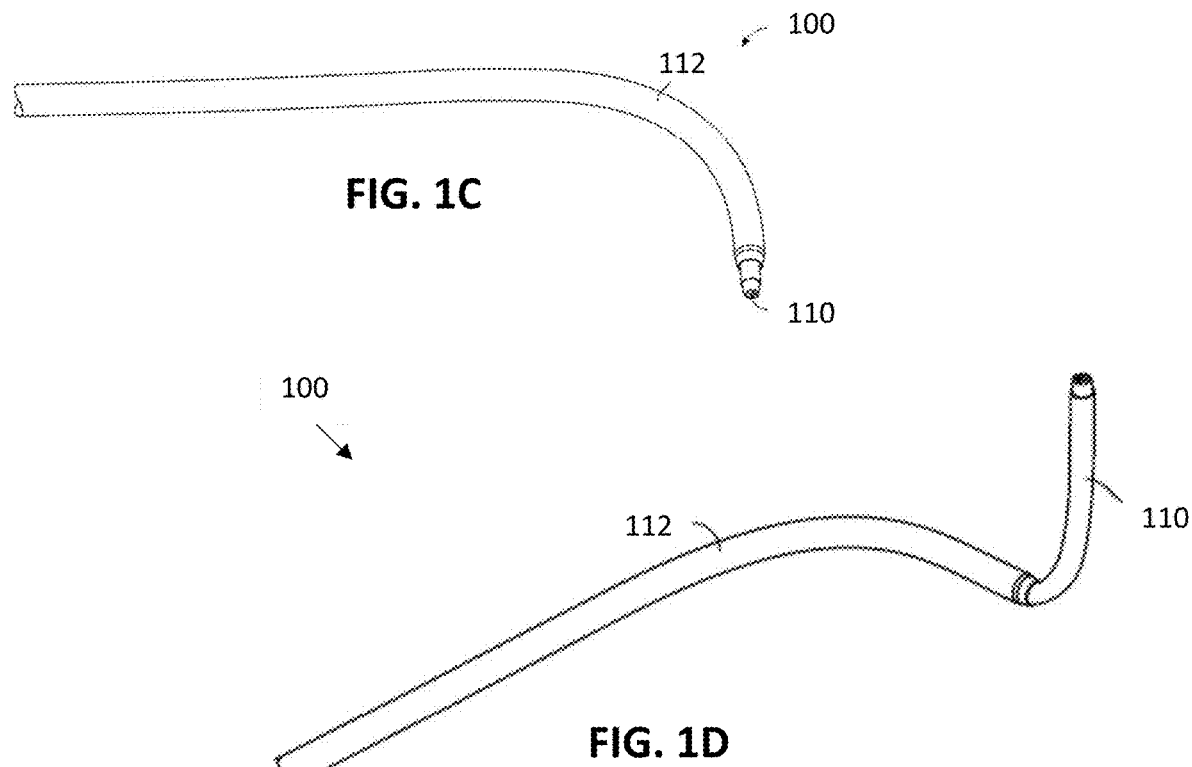
FIG. 1C
FIG. 1D

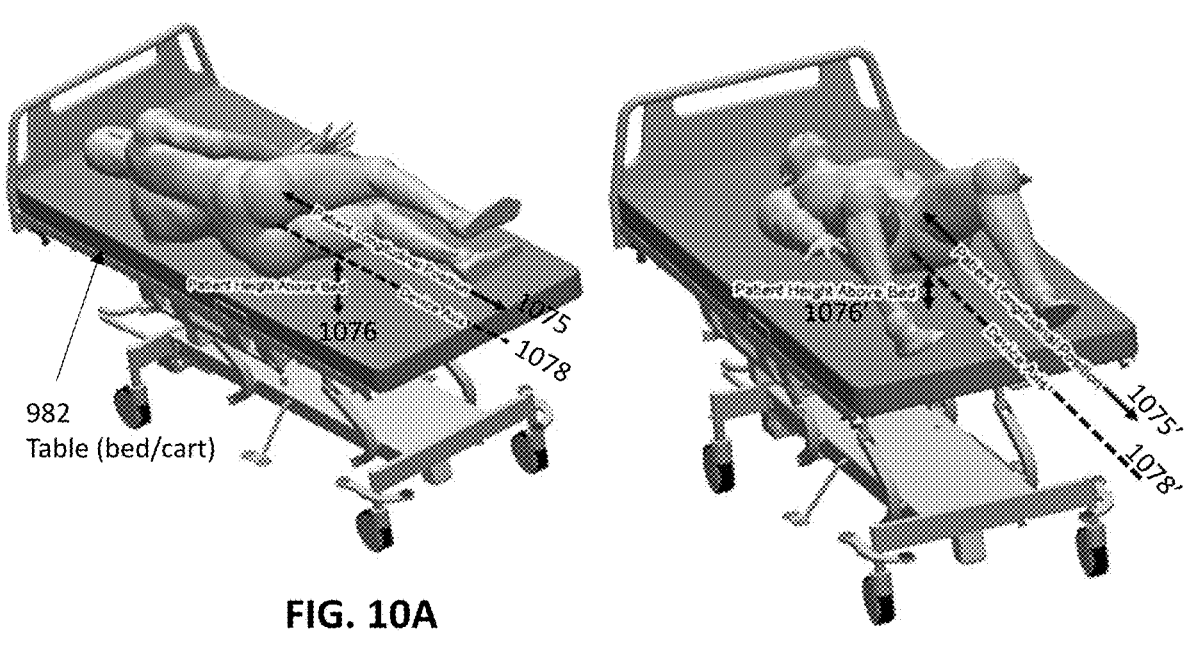
982
Table (bed/cart)
FIG. 10A
FIG. 10B
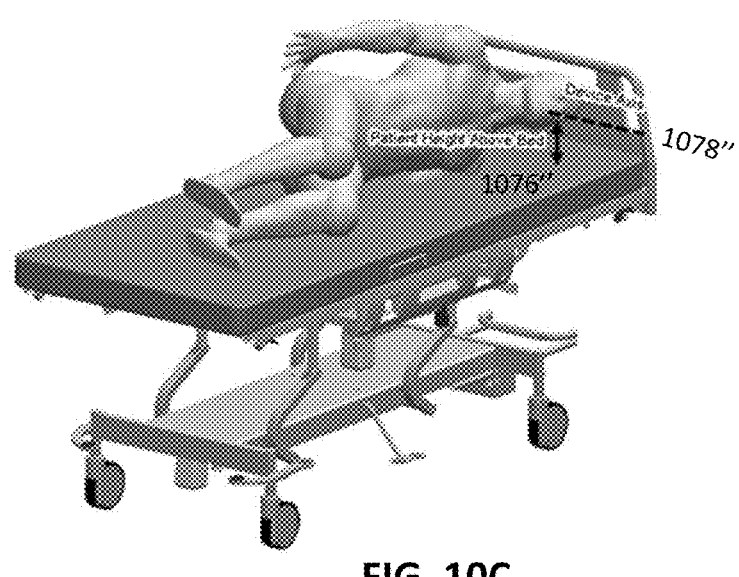
FIG. 10C

1100

1101

1176

1192

1193

1182

1200

1201

1276

1290

1337'
Yaw Axis
Rotation about a vertical axis

1301

1337

1335

1335'
Vertical Lift Axis ~ Up & Down motion

1341

1351

1401

1462
IWC Tool Entry

1431

1500

1501

1581

1582

1600

1682

1682

1600

TELESCOPING ROBOT

CLAIM OF PRIORITY

This patent application is a continuation of U.S. patent application Ser. No. 18/902,906, titled "TELESCOPING ROBOT," filed Sep. 30, 2024, now U.S. Patent Application Publication No. 2025/0108522, which claims priority to U.S. Provisional Patent Application No. 63/586,398, titled "TELESCOPING ROBOT" and filed on Sep. 28, 2023. Each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Medical procedures such as endoscopy may involve accessing and visualizing the inside of a patient's anatomy for diagnostic and/or therapeutic purposes. For example, gastroenterology, urology, and bronchoscopy involve medical procedures that allow a physician to examine patient lumens, such as the gastrointestinal tract, urology tract, vasculature, and airways. During these procedures, flexible tools or instruments, generally referred to as flexible tubular members such as endoscopes, overtubes, catheters, or guidewires, are inserted into the patient through an orifice (e.g., a natural orifice or an incision) and advanced towards a tissue site identified for subsequent diagnosis and/or treatment. The medical instrument can be controllable and articulable to facilitate navigation through the anatomy.

Management of these devices may be particularly challenging in already crowded operating rooms. Colonoscopes are just one example of a device, in this case an endoscope, that may be long and difficult to manage, particularly for robotic systems in which advancing/retracting and/or steering may be driven by a controller such as a robotic controller. Enteroscopes are used for navigation of the small intestine, and they may be even longer in length. Similar challenges exist for catheters, which are also longer length and flexible. Vascular catheters may advance into the neurovasculature, peripheral vasculature, pulmonary vasculature, and the cardiac and coronary vasculature. Guidewires may be used in the vasculature, usually in conjunction with catheters. Overtubes may be used with endoscopes. Overtubes may be used in conjunction with endoscopes, or an endoscope may be withdrawn such that only an overtube remains.

Although a large number of elongate, flexible, insertable tools (flexible tubular members, e.g., endoscopes, catheters, overtubes, guidewires, etc.) are used, or have been suggested for use, in medical procedures, controlling the insertion and operation of such apparatuses becomes increasingly unwieldy as their length increases. Thus, there is a need for storage and deploying methods and apparatuses that allow compact and efficient operation of elongate medical instruments including flexible tubular members such as endoscopes, catheters, overtubes and guidewires.

SUMMARY OF THE DISCLOSURE

Described herein are robotic apparatuses (e.g., systems, devices, etc.) and methods for positioning (relative to the patient), loading, dispensing or deploying, driving (e.g., advancing/retracting, steering, etc.), and withdrawing one or more flexible tubular members. A flexible tubular member may include one or more of: endoscopes, catheters, overtubes and/or guidewires, and in particular long-length endoscopes, including colonoscopes and enteroscopes. The methods and apparatuses described herein may address the challenges of positioning, loading, dispensing or deploying, driving, and withdrawing and/or otherwise operating such elongate medical instruments.

In general, these apparatuses provide a telescoping platform for supporting and controlling a flexible tubular member, and in particular a nested robotic endoscope that may provide significant advantages over previously described delivery and control platforms. In particular, the telescoping platform may allow extension and retraction relative to a base in both proximal and distal directions (e.g., bidirectional) from an un-extended neutral position in which the platform (e.g., the link assembly) has a compact footprint. This design may generally be significantly more compact than previously described positioning and/or controlling systems, and in particular than previously described telescoping positioning and/or controlling systems.

In some cases, it may be particularly beneficial to configure the link assembly of the apparatus (e.g., system) so that the link assembly is oriented with multiple links arranged adjacent to each other in a vertical direction. Each link may be a platform or plank shape that is generally long and thin. Each link may have a width that is less than the length and height, and may include a first major surface along both a front side and a back side (along the length and height). The link may enclose one or more elements within its thickness, such as a belt (e.g., a synchronization belt, as described below). The links of the link assembly may be similar or identical in their general shape. The innermost link may be coupled to the mount assembly or attachments for the flexible tubular member and/or flexible tubular member driver). The mount assembly may be configured to include multiple actuating regions that may separately mount to different regions of the flexible tubular member, or in some cases an inner endoscope and an outer overtube, which may move relative to each other. The outmost link may be coupled to the link assembly driver and/or may couple to the rest of the system, e.g., to the base or to an arm supported by the base. In some examples the links may have a rectangular cross-section (or generally rectangular, e.g., rectanguloid) that has a thickness that is less than its height (vertical height) and that is longer (in a proximal-to-distal direction) than it is wide or high. In general, arranging the link assembly with the links in a vertical direction may both provide superior support as the links are coupled adjacent to each other along their width (e.g., sistered to each other) vertically, as well as permitting the mounting region for the flexible tubular member (in some cases both the inner and outer members of a nested device, e.g., mounting to different portions of a mounting assembly) to be positioned lower than (e.g., closer to the floor) the top of the vertically-arranged link assembly. Since in some embodiments the spacing between the surface of the bed or table on which the patient is positioned and the entry point into the patient's anatomy (e.g., anus, mouth, etc.) may be limited, this configuration may permit access that is in-line with the patient's body. As used herein, a link may refer to a body such as a plate, panel, frame, leaf, slab, etc. The link may be solid or hollow, and/or may include one or more internal structures. The link may include one or more windows, opening, or passages therethrough.

In general, the flexible tubular member described herein may be an elongate medical instrument and may be referred to as robotic elongate medical instruments, robotic endoscopes or robotic scopes. These elongate medical instruments may include endoscopes, which may be actuated as described herein by the drive system, including robotic drive systems. Endoscopes may include colonoscopes, bronchoscope, colposcope, cystoscope, esophagoscope, gastroscope, laparoscope, thoracoscope, enteroscope, etc. In particular, the methods and apparatuses described herein may be particularly desirable for use with longer elongate medical instruments (e.g., having a length of greater than 0.7 m, 0.8 m, 0.9 m, 1 m, 1.2 m, 1.4 m, 1.6 m, 2.0 m, 2.1 m, 3 m, etc.).

These apparatuses may work well with flexible tubular members. These apparatuses may work particularly well with elongate medical instruments that include nested (i.e., two or more) components that may extend and retract relative to each other, such as telescoping elongate medical instruments. For example, a telescoping elongate medical instrument may include an inner robotic scope and an outer overtube. For example, a telescoping elongate medical instrument may include an inner robotic scope and an outer robotic scope. Either or both the inner and outer robotic scopes may be steerable, e.g., may include one or more steering member (e.g., steering tendons, etc.) that may mate with a steering interface on the apparatus. Either or both of the inner and outer scopes may include vision systems. The drive system may include a steering interface for the robotic scope, and in some examples for either or both an inner and an outer member of the robotic scope. Because nested systems involve more elements and more DOF (Degrees of Freedom), their storage, loading, deployment, driving, and withdrawal and kinematic control is particularly challenging, and therefore a particularly good fit to robotics, as robotic systems can execute complex kinematic maneuvers in a more facile manner, including through the use of software, algorithms, sensors, and actuators.

The methods and apparatuses described herein may be particularly well suited for controlling rigidizing elongate medical instruments (i.e., Dynamic Rigidization™). Rigidizing elongate medical instruments may include, but are not limited to, elongate medical instruments that are rigidized by multiple methods. One method for rigidization is the application of pressure (e.g., positive pressure and/or negative pressure). For example, the apparatuses and methods described herein may be particularly well suited for telescoping rigidizing elongate medical instruments in which an outer member of the robotic scope is a rigidizable member that may be rigidized by the application of pressure, and an inner member is a rigidizable member that may be rigidized by the application of pressure. The inner and outer members may be controllably rigidized separately and/or independently (or in a coordinated manner) which may be integrated with the drive system (e.g., robotic drive system).

Any of these apparatuses may be configured with components that are single use ('disposable'), multiple or multi-use ('responsible'), sheathed, or a very large number of uses ('reusable'). These elements may be engineered to reduce cost and landfill. They may be engineered for lower effective per-case cost. They may be engineered for ease of use, ease of install, fast procedure set-up, and ease of removal. Any of these apparatuses may be configured to allow reuse of drive system and frame, and other components that are coupled to the drive system, and may include one or more disposable components such as trays, cartridges, or the like to allow use with multiple robotic scopes, which may include sterile versions or sterile boundaries or layers. In any of these examples the apparatus may be configured so that the reusable component (e.g., the vertically-arranged link assembly, mount assembly, etc.) may be configured to be kept separate from the sterile field, e.g., by the use of a drape or cover. Thus, also described herein are drapes that may engage with the apparatuses coupled to or including the drive systems described herein.

For example, described herein are apparatuses (e.g., systems) for deploying a flexible tubular member that includes: a base; a vertically-arranged link assembly connected to the base and include a plurality of links that are vertically adjacent to each other, wherein adjacent pairs of links are each slidably coupled together by one or more mechanical movement coupling, e.g., flexible bands that extend at least partially around a cylindrical surface of a shuttle, wherein pairs of shuttles between adjacent links of adjacent pairs of links are coupled together on a synchronization belt; a driver (e.g., a linear driver) coupled to a first shuttle of the pairs of shuttles; and a first portion of a mount assembly that may be coupled to the vertically-arranged link assembly, wherein the first portion of the mount assembly is configured to couple to the flexible tubular member.

In some examples the apparatuses (e.g., systems) for deploying a flexible tubular member include: a base; a vertically-arranged link assembly connected to the base and comprising: a plurality of links that are vertically adjacent to each other, wherein adjacent pairs of links are each slidably coupled together by a pair of opposing flexible bands that extend around (e.g., bending around) a cylindrical surface of a shuttle in opposite directions, wherein pairs of shuttles between adjacent links of adjacent pairs of links are coupled together on a synchronization belt; a driver (e.g., a linear driver) coupled to a first shuttle of the pairs of shuttles; and a mount assembly including a first portion coupled to the vertically-arranged link assembly, wherein the first portion of the mount assembly is configured to couple to the flexible tubular member.

In some examples the vertically-arranged link assembly is configured to have two, three, or more links (e.g., more than 2, 3 or more links, etc.). For example, an apparatus (e.g., system) for deploying a flexible tubular member may include: a base; and a vertically-arranged link assembly connected to the base and comprising: a first link, a second link and a third link, wherein the first, second and third links are vertically adjacent to each other; a first shuttle between the first and second link and a second shuttle between the second and third link, wherein the first is movably coupled between the first and second links and the second shuttle is movably coupled between the second and third links so that the second and third links may slide distally and proximally relative to the first link, and wherein the first shuttle comprises a first vertical cylindrical surface and the second shuttle comprises a second vertical cylindrical surface; a linear driver coupled to the first shuttle; a first flexible band between the first and second links, the first flexible band extending from a first end region of the first link, around the first vertical cylindrical surface, and extending to a first end region of the second link; a second flexible band between the second and third links, the second flexible band extending from the first end region of the second link, around the second vertical cylindrical surface, and extending to a first end region of the third link, whereby proximal and/or distal movement of the second link relative to the first link by the linear driver causes proximal and/or distal movement of the third link; and a mount assembly including a first portion coupled to the vertically-arranged link assembly, wherein the first portion of a mount assembly is configured to couple to the flexible tubular member.

In any of these apparatuses, the apparatus may include a synchronization belt that may be configured to move the first shuttle in an opposite direction relative to the second shuttle. The synchronization belt may be within the link that is between the two shuttles to which it is connected. The synchronization band may be coupled to a pair of pulleys so that movement of the first shuttle in the distal direction moves the second shuttle in the proximal direction and vice versa.

In general, the bands that extend between the links are coupled to the opposite sides of the links (e.g., to the sides of the links that face each other) at the same ends, e.g., the distal ends or the proximal ends. In some cases, a pair of bands, arranged in an opposing configuration, may connect the ends of facing links of the link assembly after passing around the cylindrical surface (e.g., pulley) at different region of the cylindrical surface. For example, the first end of a first band of the opposing bands may be coupled to a distal end region of a first link of the adjacent pairs of links and to a distal end region of a second link of the adjacent pairs of links. The first end of a second band of the opposing bands may be coupled to a proximal end region of the first link of the adjacent pairs of links and to a proximal end region of the second link of the adjacent pairs of links.

In general, the flexible bands and/or belts may be formed of a flat, relatively thin and flexible material, including a thin flat metal (e.g., stainless steel, etc.). Thus, the flexible bands may comprise flat bands. The width of the flat band may be many times the thickness (e.g., greater than 5×, 10×, 15×, 20×, etc.). For example, the flat band may have a width of 0.5 cm, 1 cm, 1.5 cm, 2 cm, 3 cm, 4 cm, 5 cm, etc.

In any of these apparatuses, the plurality of links may each have a vertical height that is greater than a width and less than a distal to proximal length. In some examples, the plurality of links may each have a vertical height that is less than a distal to proximal length, and at least twice a width. For example, the links may be between about 10 cm and 100 cm (e.g., between 15 cm and 75 cm, between 20 cm and 60 cm, etc.) long, between about 3 cm and 30 cm high (e.g., between 4 cm and 20 cm, between 5 cm and 18 cm, etc.), and between about 0.5 cm and 6 cm wide (e.g., between about 1 cm and 5 cm, between about 0.5 cm and 4 cm, etc.).

As mentioned, the mount assembly for coupling to the flexible tubular member (e.g., the one or more portions of the mount assembly) may be coupled to one of the outer links of the link assembly, such as to an outer link of the plurality of links of the vertically-arranged link assembly. The mount assembly may include one or more drivers for steering and/or otherwise manipulating the flexible tubular member. In examples in which the flexible tubular member is a nested device (e.g., a nested, rigidizing robotic device) having an inner endoscope and an outer overtube, the mount assembly may include a first region (or portion) configured to mount to the outer overtube and a second region (or portion) configured to mount to the inner endoscope. The mount assembly may be configured so that these two regions may move relative to each other to allow relative movement of the inner vs. outer members of the nested device. For example, the first mount region may be configured to couple to a nested robotic device having an overtube within which the endoscope is nested within. In some examples the mount assembly may include an overtube mount (first mount region) and an endoscope mount (second mount region), wherein the endoscope mount is configured to move proximally and/or distally relative to the overtube mount.

Any of these apparatuses may be configured to allow position of the link assembly (and therefore the endoscope) in multiple degrees of freedom. For example, these apparatuses may be configured to allow the device to adjust the height of the link assembly relative to the base (e.g., the floor). Any of these apparatuses may include a vertical lift arm coupling the vertically-arranged link assembly to the base, wherein the vertical lift arm is configured to raise and lower the vertically-arranged link assembly relative to the base. In some examples the apparatus may include a yaw adjust member between the vertically-arranged link assembly and the base, wherein the yaw adjust member is configured to swing the vertically-arranged link assembly pivotally around the base. These adjustments may be controlled and/or driven, e.g., by a drive member and/or a controller controlling a drive member. The apparatus may include one or more locks for locking these devices in a particular configuration. In general, the link assembly may be coupled to the base either directly or through one or more arms.

Any appropriate drive (e.g., drive sub-system, driver, etc.) may be used to drive movement of the shuttle and therefore extension and/or retraction of the link assembly. The drive may be a linear drive (e.g., that converts rotary motion into linear (distal/proximal) movement. For example, the drive may include a ball screw nut assembly. In some examples the liner drive is housed within the first link of the plurality of links (e.g., the link coupled to the base either directly or indirectly). In some examples the drive (e.g., linear drive) for the link assembly may be separate from the link assembly and may be eternal to the links, but may couple to the shuttle (the first shuttle, which may also be referred to as the drive shuttle) through the first link.

Any of the apparatuses described herein may include a controller including one or more processors, and control circuitry for receiving control input, providing output to control and/or coordinate extension/retraction of the link assembly and/or the flexible tubular member driver (e.g., overtube driver and/or endoscope driver in nested configurations). For example, a controller may be configured to control the linear drive to move plates (e.g., links) of the plurality of links distally and proximally relative to the base controlling operation of the linear driver. The controller may include control logic (software, firmware, and/or hardware) for performing any of the methods described herein. The controller may coordinate with the steering and/or, in examples using a rigidizing device, rigidizing of the catheter. The controller may receive user input and may automate some or all of the guidance of the apparatus. The controller may receive and process (or transmit and/or store) inputs from one or more sensors.

Any of the apparatuses described herein may include a flexible tubular member support coupled to the vertically-arranged link assembly and configured to prevent buckling of the flexible tubular member at it extends distally from the vertically-arranged link assembly. The flexible tubular member support (referred to here as an endoscope support or simply a support) may be a strut, beam, rod, pole, etc. that may support the length of the flexible tubular member as it extends distally and/or proximally away from the link assembly. In some examples the flexible tubular member support may include one or more loops or straps for holding (and supporting) a portion of the flexible tubular member.

Any of the apparatuses described herein may include a tool driver for operating or assisting in operating a tool that is inserted into or through a working channel (internal or external working channel) of the flexible tubular member. For example, a tool driver may be coupled to the vertically-arranged link assembly and configured to actuate a tool within a working channel of an endoscope comprising the flexible tubular member.

As mentioned, any of these apparatuses may include one or more sensors configured to detect one or more operating parameters for the system. For example, the apparatus may include one or more load sensors configured to detect a load applied to the vertically-arranged link assembly. The one or more load sensors may be configured as a current sensor that detects current of, e.g., the linear driver.

Any of the apparatuses described herein may be configured to work with a variety of elongate medical instruments (robotic scopes). However, in any of these apparatuses, the elongate medical instruments (e.g., robotic scope) may be included as part of the system.

As mentioned, any of these apparatuses may include the elongate medical instrument (e.g., the robotic scope). For example, the system may include the robotic scope, which may be a colonoscope. In some examples the robotic scope included with the apparatus is a rigidizable flexible tubular member comprising a rigidizable inner member concentrically positioned within a rigidizable outer member. In general, any of these apparatuses may include a pressure input configured to couple the robotic scope to a pressure source to control rigidity of the robotic scope, including either or both an inner member and outer member in variations including inner and outer members.

For example, described herein are systems for deploying a flexible tubular member, the system comprising: a base; a telescoping link assembly connected to the base and comprising: a plurality of links that are adjacent to each other, wherein adjacent pairs of links are each slidably coupled together, wherein the plurality of links are configured to extend from a compact configuration to a length of 0.6 m or longer; a linear driver configured to drive movement of the links of the telescoping link assembly; and a mount assembly coupled to the link assembly, wherein the mount assembly is configured to couple to the flexible tubular member.

In general, the compact configuration may have a significantly smaller length (e.g., extending in a distal to proximal direction) than the extended length of the device. For example, the length of the compact configuration may be 50% or less than the length of the fully extended configuration (e.g., 45% or less, 40% or less, 35% or less, 30% or less, 25% or less, 20% or less, etc.).

As mentioned any of these apparatuses may be bidirectional, so that they may expand distally or proximally from the compact configuration. For example, the telescoping link assembly may be bidirectional, and the compact configuration may be a neutral configuration such that the plurality of links may be extended either distally from the neutral configuration to a length of 0.6 m or longer or proximally from the neutral configuration to a length of 0.6 m or longer. Bidirectional expansion provides many advantages, particularly as compared to systems that expand only in one direction, e.g., from a stable or fixed base. Bidirectional systems may allow a much more compact foot print in the compact configuration, and may allow use of the apparatus in even very narrow or space-constrained regions, including next to a hospital bed or operating table. Bidirectional apparatuses may provide a longer travel distance when moving in the distal to proximal axis.

Any of the apparatuses described herein may include a plurality of links that are vertically adjacent to each other, relative to ground. Thus, the links may be arranged side-by-side, rather than on top of each other.

In general, any of these apparatuses may be configured so that moving any of the individual links causes a coordinated movement of all or some of the other links; for example, driving movement (proximal/distal movement) of the first link may extend the set of links in the same direction of movement. This may advantageously allow control of movement by a single driver (or set of drivers operating on a single link, e.g., coupled to the base). In any of these apparatuses this may be achieved using one or more synchronizing members coupled to each link of the plurality of links configured to coordinate movement of all of the links when force is applied to one of the links. The synchronization member may be mechanical (e.g., belts, bands, etc.) and/or may include software or firmware to coordinate between the different links. For example, each link may be individually driven, and the activity of the drives may be coordinated by one or more processors.

In any of these examples a mount assembly may include an overtube mount and an endoscope mount, wherein the endoscope mount is configured to move proximally and/or distally relative to the overtube mount.

The link assembly may be configured to extend from the compact configuration to any appropriate length. For example, the link assembly may be configured to extend to a length of 1 m or longer (e.g., 1.1 m or longer, 1.2 m or longer, 1.3 m or longer, 1.4 m or longer, 1.5 m or longer 1.6 m or longer, 1.7 m or longer, 1.8 m or longer, 1.9 m or longer, 2 m or longer, etc.).

The apparatuses described herein may have a very small distal clearance height or offset. Thus, the height of the mount assembly relative to the link assembly may be adjustable and/or may be relatively low. For example, a vertical distance from the mount assembly to lowermost surface of the link assembly may be less than 20 cm (e.g., 20 cm or less, 19 cm or less, 18 cm or less, 17 cm or less, 16 cm or less, 15 cm or less, 14 cm or less, 12 cm or less, 10 cm or less, etc.). Thus, the distal end of the mount assembly and link assembly may extend distally to a patient positioned on a bed or table and may be positioned in-line with a patient orifice even when the orifice is relatively close to the bed/table surface (e.g., less than 20 cm) without interference between the bed/table and the distal end of the extended apparatus.

In general, the links may be configured to smoothly slide relative to each other to extend/retract distally and/or proximally. In any of these examples the plurality of links may be configured so that adjacent pairs of links are each slidably coupled together by a pair of opposing flexible bands that extend around one or more surfaces of shuttle in opposite directions. For example, the link assembly may comprise one or more (e.g., a pair) of shuttles between adjacent links of adjacent pairs of links; the shuttles may be coupled together on a synchronization member (e.g., synchronization belt).

Also described herein are systems for deploying a flexible tubular member, the system comprising: a base; a bidirectional telescoping link assembly connected to the base and comprising: a plurality of links that are adjacent to each other, wherein adjacent pairs of links are each slidably coupled together, wherein the plurality of links are configured to extend proximally from a compact neutral configuration to a proximal extended configuration and to extend distally from the compact neutral configuration to a distal extended configuration, wherein the compact neutral configuration has a length that is 50% or less than a length of the proximal extended configuration and 50% or less a length of the distal extended configuration; a linear driver configured to drive movement of the links of the telescoping link assembly; and a mount assembly coupled to the link assembly, wherein the mount assembly is configured to couple to the flexible tubular member.

As mentioned, in any of these apparatuses (e.g., systems) the plurality of links may be vertically adjacent to each other. Alternatively, in some examples the plurality of links may be horizontally adjacent to each other (e.g., stacked). As mentioned, any of these apparatuses may include one or more synchronizing members coupled to each link of the plurality of links configured to coordinate movement of all of the links when force is applied to one of the links. The mount assembly may comprise an overtube mount and an endoscope mount, wherein the endoscope mount is configured to move proximally and/or distally relative to the overtube mount. The link assembly may be configured to extend from the compact configuration to a length of 1 m or longer. The vertical distance from the mount assembly to lowermost surface of the link assembly may be less than 20 cm. The plurality of links may be configured so that adjacent pairs of links are each slidably coupled together by a ball screw nut assembly. The plurality of links may be configured so that adjacent pairs of links are each slidably coupled together by a pair of opposing flexible bands that extend around one or more surfaces of shuttle in opposite directions. Any of these apparatuses may include one or more (e.g., a pairs) of shuttles between adjacent links of adjacent pairs of links that are coupled together on a synchronization belt.

Also described herein are systems for deploying a flexible tubular member, the system comprising: a base; a vertically-arranged link assembly connected to the base and comprising: a plurality of links that are vertically adjacent to each other, wherein adjacent pairs of links are each slidably coupled together by a pair of opposing flexible bands that extend around one or more surfaces of a shuttle in opposite directions, wherein pairs of shuttles between adjacent links of adjacent pairs of links are coupled together on a synchronization belt; a linear driver coupled to a first shuttle of the pairs of shuttles; and a mount assembly coupled to the vertically-arranged link assembly, wherein the mount assembly is configured to couple to the flexible tubular member.

The synchronization belt may be configured to move the first shuttle in an opposite direction relative to the second shuttle. A first end of a first band of the opposing bands may be coupled to a distal end region of a first link of the adjacent pairs of links and to a distal end region of a second link of the adjacent pairs of links, wherein a first end of a second band of the opposing bands may be coupled to a proximal end region of the first link of the adjacent pairs of links and to a proximal end region of the second link of the adjacent pairs of links. The flexible bands may comprise flat bands. For example, the flexible bands may comprise metallic bands. The plurality of links may each have a vertical height that is greater than a width and less than a distal to proximal length. The plurality of links may each have a vertical height that is less than a distal to proximal length, and at least twice a width. The cylindrical surfaces may comprise pulleys.

In any of these apparatuses, the mount assembly may be coupled to an outer link of the plurality of links of the vertically-arranged link assembly.

Any of these apparatuses may include a vertical lift arm having a vertical axis coupling the vertically-arranged link assembly to the base, wherein the vertical lift arm is configured to raise and lower the vertically-arranged link assembly relative to the base.

Any of these apparatuses may include a yaw adjust member between the vertically-arranged link assembly and the base, wherein the yaw adjust member is configured to swing the vertically-arranged link assembly pivotally around the base. The mount assembly may be configured to couple to the flexible tubular member that comprises a nested robotic device having an overtube within which an inner endoscope is nested.

The mount assembly may comprise an overtube mount and an endoscope mount, wherein the endoscope mount is configured to move proximally and/or distally relative to the overtube mount.

In any of these apparatuses, the liner drive may comprise a ball screw nut assembly, or any other appropriate linear driver. The liner drive may be housed within a first link of the plurality of links. Alternatively in some examples the linear driver may be housed external to the first link.

Any of these apparatuses may include a controller configured to control the linear drive to move links of the plurality of links distally and proximally relative to the base controlling operation of the linear driver.

Any of these apparatuses may include a flexible tubular member support coupled to the vertically-arranged link assembly and configured to prevent buckling of the flexible tubular member at it extends distally from the vertically-arranged link assembly.

In some examples, the mount assembly may be below the top of the vertically-arranged link assembly. The apparatuses described herein may include a tool driver coupled to the vertically-arranged link assembly and configured to actuate a tool within a working channel of the flexible tubular member.

In general, any of these apparatuses may include one or more sensors configured to detect one or more operating parameters for the system. For example, these apparatuses may include one or more load sensors configured to detect a load applied between the vertically-arranged link assembly and the patient. The load may be transmitted through the one or more flexible tubular member (e.g., endoscope, etc.). The one or more load sensors may comprise a current sensor configured to detect current of the linear driver.

The mount assembly (e.g., in some example coupled to a vertically-arranged link assembly) may be coupled to the base either directly or through one or more arms.

For example, a system for deploying a flexible tubular member, the system comprising: a base; a vertically-arranged link assembly connected to the base and comprising: a first link, a second link and a third link, wherein the first, second and third links are vertically adjacent to each other; a first shuttle between the first and second link and a second shuttle between the second and third link, wherein the first is movably coupled between the first and second links and the second shuttle is movably coupled between the second and third links so that the second and third links may slide distally and proximally relative to the first link, and wherein the first shuttle comprises a first vertical cylindrical surface and the second shuttle comprises a second vertical cylindrical surface; a linear driver coupled to the first shuttle; a first flexible band between the first and second links, the first flexible band extending from a first end region of the first link, around the first vertical cylindrical surface, and extending to a first end region of the second link; a second flexible band between the second and third links, the second flexible band extending from the first end region of the second link, around the second vertical cylindrical surface, and extending to a first end region of the third link, whereby proximal and/or distal movement of the second link relative to the first link by the linear driver causes proximal and/or distal movement of the third link; and a mount assembly coupled to the vertically-arranged link assembly, wherein the mount assembly is configured to couple to the flexible tubular member. The apparatus may include a third flexible band between the first and second links, the third flexible band extending from a second end region of the first link, around the first vertical cylindrical surface, and extending to a second end region of the second link, and a fourth flexible band between the second and third links, the fourth flexible band extending from the second end region of the second link, around the second vertical cylindrical surface and extending to the second end region of the third link.

Any of these apparatuses may include a synchronization belt coupled to the first shuttle and to the second shuttle, and configured to move the first shuttle relative to the second shuttle.

In any of these apparatuses, the motion of the linear drive may be transmitted to the third link with a 4:1 ratio or greater.

In general, any of the apparatuses described herein may include the link assembly and the mount assembly for use with a telescoping (e.g., nested) elongate member. For example, described herein are systems for deploying a nested robotic device having an inner rigidizing member slidably disposed at least partially within an outer rigidizing member, the system comprising: a base; a vertically-arranged link assembly connected to the base and comprising: a first link, a second link and a third link, wherein the first, second and third links are vertically adjacent to each other; a first shuttle between the first and second link and a second shuttle between the second and third link, wherein the first is movably coupled between the first and second links and the second shuttle is movably coupled between the second and third links so that the second and third links may slide distally and proximally relative to the first link, and wherein the first shuttle comprises a first vertical cylindrical surface and the second shuttle comprises a second vertical cylindrical surface; a linear driver coupled to the first shuttle; a first flexible band between the first and second links, the first flexible band extending from a first end region of the first link, around the first vertical cylindrical surface, and extending to a first end region of the second link; a second flexible band between the second and third links, the second flexible band extending from the first end region of the second link, around the second vertical cylindrical surface, and extending to a first end region of the third link, whereby proximal and/or distal movement of the second link relative to the first link by the linear driver causes proximal and/or distal movement of the third link; and a mount assembly including: a first mount region coupled to the third link of the vertically-arranged link assembly, wherein the first mount region is configured to couple to the outer rigidizing device; and a second mount region that is linearly movable proximally and distally relative to the first mount region and is configured to couple to the inner rigidizing device.

Also described herein are method of operating any of the apparatuses described herein. For example a method of deploying an endoscope nested with an overtube may include: advancing and/or retracting the overtube together with the endoscope by moving a first link of a bidirectional telescoping link assembly, wherein the overtube is coupled to an overtube mount on the first link and wherein the endoscope is coupled to an endoscope mount on the first link, and wherein the bidirectional link assembly comprises a plurality of links, including the first link, that are slidably coupled together and are adjacent to each other, and wherein advancing the overtube comprises extending the plurality of links distally from a compact neutral configuration to a proximal extended configuration and wherein retracting the overtube comprises retracting the plurality of links proximally from the compact neutral configuration to a proximal extended configuration, wherein the compact neutral configuration has a length that is 50% or less than a length of the proximal extended configuration and 50% or less a length of the distal extended configuration; and moving the endoscope distally into or out of the overtube by changing the relative positions of the endoscope mount and the overtube mount on the first link.

Any of these methods may include extending the plurality of links using a linear driver configured to drive movement of the links of the telescoping link assembly. Any of these methods may include coupling the overtube to the overtube mount, and/or coupling the endoscope nested within the overtube to the endoscope mount.

For example, a method of deploying an endoscope nested with an overtube may include: advancing and/or retracting the overtube together with the endoscope by moving a first link of a bidirectional telescoping link assembly, wherein the overtube is coupled to an overtube mount on the first link and wherein the endoscope is coupled to an endoscope mount on the first link, and wherein the bidirectional link assembly comprises a plurality of links, including the first link, that are slidably coupled together and are adjacent to each other, and wherein advancing the overtube comprises extending the plurality of links distally from a compact neutral configuration to a proximal extended configuration and wherein retracting the overtube comprises retracting the plurality of links proximally from the compact neutral configuration to a proximal extended configuration, wherein the compact neutral configuration has a length that is 50% or less than a length of the proximal extended configuration and 50% or less a length of the distal extended configuration; and moving the endoscope distally into or out of the overtube by changing the relative positions of the endoscope mount and the overtube mount on the first link. Extending the plurality of links may include using a linear driver to drive movement of the links of the telescoping link assembly. As mentioned, any of these methods may include coupling the overtube to the overtube mount and/or coupling the endoscope nested within the overtube to the endoscope mount.

Also described herein are apparatuses including one or more supports that are configured to support the nested, telescoping apparatus (e.g., overtube and endoscope) during operation of the apparatus, and methods of using them. For example, an apparatus may include: a telescoping link assembly comprising: a plurality of vertical links that are adjacent to each other, wherein adjacent pairs of vertical links are each slidably coupled together and configured to move relative to each other and relative to a base link; a first mount coupled to a first link of the link assembly, wherein the first mount is configured to engage an overtube; a second mount coupled to the first link and configured engage an endoscope nested with the overtube, wherein the overtube and endoscope are configured to be moved in a distal-to-proximal line by sliding the vertical links of the telescoping link assembly relative to the base link; and a plurality of supports movably coupled to the telescoping link assembly, wherein each support of the plurality of supports comprises a seating region configured to hold the overtube and endoscope in-line with the distal-to-proximal line.

Each support of the plurality of supports may be configured to be deflected so that the seating region of each support is moved out of the distal-to-proximal line as the plurality of the links of the telescoping link assembly are extended distally. At least some of the supports of the plurality of supports may be configured to be deflected down and laterally as the plurality of the links of the telescoping link assembly are extended distally.

As mentioned, any of these apparatuses may include a base. Any of these apparatuses may include a linear driver configured to drive movement of the vertical links of the telescoping link assembly. At least one of the supports of the plurality of supports may be configured to move from a deployed configuration in which the seating regions of the supports are configured to hold the overtube and endoscope in-line with the distal-to-proximal line, to a pre-deployed configuration in which the supports are raised vertically out of a plane of the distal-to-proximal line.

At least one of the supports of the plurality of supports may be coupled to an extender on the link assembly that is configured to extend distally from the link assembly. The first and/or second mount may be configured to move relative to each other on the first link to adjust the relative positions of the endoscope and the overtube.

For example, an apparatus may include: a base; a bidirectional telescoping link assembly connected to the base and comprising: a plurality of vertical links that are adjacent to each other, wherein adjacent pairs of vertical links are each slidably coupled together and configured to move bidirectionally relative to a base link; a linear driver configured to drive movement of the vertical links of the bidirectional telescoping link assembly; a first mount coupled to a first link of the link assembly, wherein the first mount is configured to engage an overtube; a second mount coupled to the first link and configured engage an endoscope nested with the overtube, wherein the overtube and endoscope are configured to be moved in a distal-to-proximal line by sliding the vertical links of the bidirectional telescoping link assembly; and a plurality of supports coupled to the telescoping link assembly, wherein each support of the plurality of supports comprises a seating region configured to move between a first configuration which the seating region holds the overtube and endoscope in-line with the distal-to-proximal line, and a second configuration in which the seating region of each support is configured to move out of the distal-to-proximal line as the plurality of the links of the telescoping link assembly are extended distally.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIGS. 1A-1D illustrate one example of an elongate medical instrument, such as a nested robotic scope device, that may be used with the methods and apparatuses described herein. The elongate medical instrument in this example is an endoscope (e.g., in some examples, a colonoscope) having a nested inner member and an outer member that are both selectively rigidizing.

FIG. 6B shows a top front perspective view, FIG. 6C is a bottom front perspective view, and FIG. 6D is a bottom perspective view.

FIGS. 7F-7H schematically illustrate the bidirectional operation of an assembly of linear links, showing an un-extended configuration (FIG. 7F) in which the inner and intermediate links are aligned with the outer link, a proximally extended configuration (FIG. 7G) in which the inner and intermediate links telescope proximally relative to the outer link, and a distally extended configuration (FIG. 7H) in which the inner and intermediate links telescope distally relative to the outer link.

FIGS. 10A-10C illustrate examples of the relative distances and axes for accessing a patient using a system for deploying a nested robotic device.

FIG. 16A shows a side perspective view and FIG. 16B shows a top view.

FIG. 18A shows the supports fully deployed and configured to support a nested telescoping assembly in an insertion axis. FIG. 18B shows a top view of a link assembly such as the one shown in FIG. 18A with the supports fully deployed and supporting a portion of a nested telescoping assembly in the insertion axis.

FIG. 19A shows the apparatus in a stored configuration, prior to loading the nested telescoping apparatus. FIGS. 19B-19D show setup of the link assembly including supports to receive the nested telescoping apparatus. FIGS. 19E-19H illustrate loading of the nested telescoping apparatus onto the apparatus. FIG. 19H shows the pre-deployed configuration with the nested telescoping apparatus attached and in a stored configuration ready for positioning relative to a patient.

In FIGS. 20A-20I the supports are moved in or out of the insertion axis as needed to support the nested telescoping apparatus.

DETAILED DESCRIPTION

Figure 2:
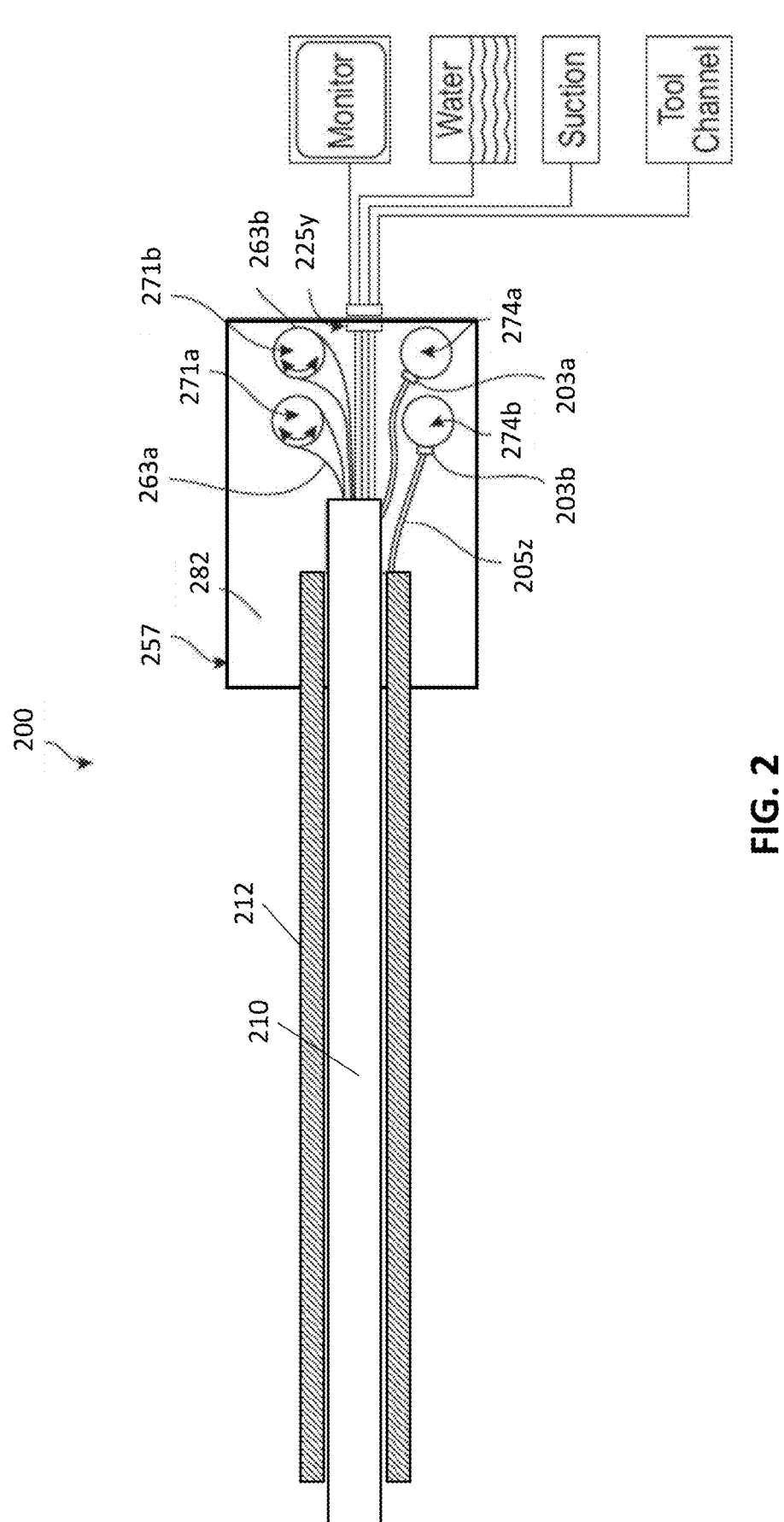
FIG. 2 shows an example of a mechanism for actuating an elongate medical instrument similar to that shown in FIGS. 1A-1D.

Aspects of the present disclosure may be integrated into a robotically-enabled medical system capable of performing a variety of medical procedures, including both minimally invasive procedures—such as laparoscopy- and non-invasive procedures—such as endoscopy. Among endoscopy procedures, the system may be capable of performing colonoscopy, enteroscopy, bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user. An apparatus (e.g., a system, devices, etc.) for operating and/or deploying a robotic scope may be configured extend (distally) and/or retract (proximally) to control operation of the flexible tubular member.

In general, these apparatuses may be used to deliver a flexible tubular member, including in particular, a nested endoscope that include both an outer "overtube" an inner endoscope that may be moved proximally/distally relative to each other and may each be rigidized to guide and/or steer the device through the patient's body. These apparatuses may include a telescoping set of links, and in particular vertically-arranged links. For example, the apparatuses (device, systems, etc.) described herein may be configured as a portion of a robotic system for delivery of a pair of a nested endoscope device, including an inner endoscope and an outer overtube, that are each capable of relatively high and low levels of compliance.

The apparatuses described herein may have a generally linear form factor, and may therefore provide a linear kinematic system for delivery of devices. The primary linear axis that may position the apparatus (e.g., the overtube of the endoscope) into the patient includes a telescoping mechanism formed of a link assembly. The bidirectional telescoping action of this link assembly may allow the relatively long linear axis to be relatively short when its full extension is not needed, which addresses room size limitations in some facilities. In examples including flexible tubular member systems with both inner and outer members, the position of the inner endoscope relative to the outer overtube may be controlled by an independent linear axis. Although these apparatuses may be used with virtually any flexible tubular member, they may be particularly helpful when using a nested, and in particular rigidizing, endoscope, such as a dual rigidizing endoscope.

For example, FIGS. 1A-1D illustrate one example of a robotic scope configured as a dual rigidizing endoscope. In FIGS. 1A-1D, the dual rigidizing endoscope 100 is configured as a nested system including a rigidizable (e.g., rigidizing) outer member 112 and a rigidizable inner member 110. In FIG. 1A, the steerable inner rigidizing member 110 is positioned within the outer rigidizing member 112 such that the distal end of the inner rigidizing member 110 extends outside of the outer rigidizing member. In some cases the inner rigidizing member 110 may be fully retracted into the outer rigidizing member 112. FIG. 1B shows the distal end of the inner rigidizing member 112 is bent slightly in a desired direction/orientation (e.g., via steering cables or other steering mechanism) and then rigidized (e.g., using positive or negative pressure). 112 may also be bent because it was in the flexible state as it followed the curvature of 110, and then was subsequently rigidized. In FIG. 1C, the outer rigidizing member 112 (in the flexible configuration) is advanced over the rigidized inner rigidizing member 110 (including over the bending distal section). Once the distal end of the outer rigidizing member 100 is sufficiently advanced over the distal end of the inner rigidizing member 110, then the outer rigidizing member 112 can be rigidized (e.g., using positive or negative pressure as described herein). In FIG. 1D, the inner rigidizing member 110 can then be transitioned to the flexible state (e.g., by removing the positive or negative pressure in some examples, and by allowing the steering cables to go slack such that tip can move easily) and can be advanced and directed/oriented/ steered as desired. Alternately, in FIG. 1D, the inner rigidizing member 110 can be actively steered (either manually or via computational control) as it emerges such that is minimizes the load on the rigidized outer tube. Minimizing the load on the outer rigidizing member may make it easier for this tube to hold the rigidized shape. Once the inner rigidizing member 110 is rigidized, the outer rigidizing member 112 can be transitioned to the flexible state and advanced thereover. The process can then be repeated to navigate through even more tortious anatomies. However, it may be particularly difficult to coordinate the movement of the inner and outer members, including advancing/retracting and selectively rigidizing either the inner or outer or both, making a robotically controlled system particularly advantageous. The repeated process can result in "shape copying," whereby the inner and outer rigidizing members, while in a flexible configuration, may continuously conform to (or copy) the shape of whichever member is in the rigid configuration.

The example of a robotic scope shown in FIGS. 1A-1D illustrate the operation of just one type of medical instrument that may be used with the methods and apparatuses described herein. Furthermore, these apparatuses may be configured so as to function as endoscopes, including one or more of imaging, irrigation, lighting, steering channels for removing or applying materials, etc. For example, the robotic scope 100 may be a "navigation" device comprising a camera, lighting and a distal steering section. The navigation device (scope or portion of a scope) may be well sealed such that it is easy to clean between procedures. In some examples it does not need to be cleaned because it is fully sheathed, including both on the outside and through the working channels. In some examples a second inner device may then be placed inside the rigidized outer member and advanced past the distal end of the outer member. The second inner member may be a "therapeutic" tube comprising such elements as a camera, lights, water, suction and various tools. The "therapeutic" device may not have a steering section or the ability to rigidize, thereby giving additional room in the body of the therapeutic tube for the inclusion of other features, for example, tools for performing therapies. Once in place, the tools on the "therapeutic" tube may be used to perform a therapy in the body, such as, for example, a mucosal resection or dissection in the human GI tract.

In some examples, the rigidizing members described herein can transition from a flexible configuration to a rigid configuration and the stiffness may be considered "variable stiffness" as it may be selected by the user or system. For example, each rigidizing member may be rigidized by applying a positive or negative pressure to the wall of the rigidizing member or within the wall of the rigidizing member. With the positive or negative pressure removed (or reversed), the layers can easily shear or move relative to each other; the release of the positive or negative pressure may allow the layers to transition to a condition in which they exhibit a substantially enhanced ability to resist shear, movement, bending, torque and buckling, thereby providing system rigidization. Although the examples shown above in the described apparatuses that rigidize by the application of pressure (e.g., positive or negative pressure), the methods and apparatuses described herein may be used with any appropriate rigidizable member(s), not limited to positive or negative pressure rigidizing apparatuses. For example, the rigidizable members described herein may refer to any appropriate rigidizing device, including members that may be rigidized by jamming particles, by phase change and/or shape memory alloys, by interlocking components (e.g., cables with discs or cones, etc.), EAP (electro-active polymers) or any other rigidizing mechanism.

Any of the rigidizable apparatuses described herein may include rigidizing layers or regions that engage with a compression layer (which may be or may include a bladder) that applies force to the rigidizing layer to rigidize the rigidizing layer or in some cases to de-rigidize (e.g., release from rigidization) the rigidizing layer. In some examples, these rigidizable apparatuses may include a rigidizing layer that could include a braid, knit, woven, chopped segments, randomly distributed or randomly oriented filaments or strands, engagers, links, scales, plates, segments, particles, granules, crossing filaments, or other materials forming the rigidizing layer. For example, the rigidizing layer may comprise multiple strand lengths or strand segments that cross over each other (e.g., as part of a braid, knit, woven, etc.); the compression layer may apply force to drive the crossing strand lengths or strand segments against each other. Although many of the examples shown herein are braids, any of these apparatuses may instead or in addition include a general rigidizing layer comprising crossing strand lengths or strand segments. The examples of rigidizing apparatuses described herein may use pressure (positive pressure) and/or negative pressure to selectively and controllable rigidize. In some examples the method described herein may be used with any appropriate rigidizing apparatus.

A sequence identical to or similar to that illustrated in FIGS. 1A-1D may be performed by the apparatuses described herein, including in particular, the rotational systems described herein.

In general, the robotic scopes may be actively steered automatically or manually, including by a user operating the apparatus, so that the robotic scope is steered into known, assumed, or measured shapes, when advanced into the anatomy. This may be particularly useful and important when navigating a dual rigidizing endoscope such as (but not limited to) that shown in FIGS. 1A-1D. For example, a distal tip of the inner rigidizing member can be steered (including steering to set or match a shape of the section of the outer rigidizing member). Typically, a region of the inner and/or outer members of the scope may be steered at a region immediately proximal to the distal tip.

Thus, generally, the apparatuses described herein may include effectors for controlling operation of the scope operated by the device, including for steering, rigidizing, navigation, imaging, lighting, etc. For example, the effectors (e.g., end effectors) of some variations of the system's robotic arms may include an instrument driver that may incorporate electro-mechanical means for actuating (e.g., steering) the medical instrument and may include a mount assembly for detachably coupling to the scope or portion of the scope (e.g., inner member, outer member, etc.). For example, PCT application PCT/US2023/064999, filed Mar. 27, 2023, and titled "METHODS AND APPARATUSES FOR NAVIGATING USING A PAIR OF RIGIDIZING DEVICES," describes examples of apparatuses including nested apparatus that may be used with any of the methods and apparatuses described herein. Other examples of apparatuses that may be used with the methods and apparatuses described herein may include nested catheters such as those described, for example, in U.S. patent application Ser. No. 17/902,770, titled "NESTED RIGIDIZING DEVICES," filed on Sep. 8, 2022, U.S. patent application Ser. No. 18/000,062, titled "RIGIDIZING DEVICES," filed on May 26, 2021, patent application no. PCT/US2022/014497, titled, "DEVICES AND METHODS TO PREVENT INADVERTENT MOTION OF DYNAMICALLY RIGIDIZING DEVICES," filed on Jan. 31, 2022, patent application no. PCT/US2022/082300, titled "METHODS AND APPARATUSES FOR REDUCING CURVATURE OF A COLON," filed on Dec. 22, 2022, patent application no. PCT/US2023/062206, titled "DYNAMICALLY RIGIDIZING COMPOSITE MEDICAL STRUCTURES," filed on Feb. 8, 2023. Each of these applications are herein incorporated by reference in their entirety.

In some examples, the robotic scope, such as a dual rigidizing apparatus shown in FIGS. 1A-1D may be robotically controlled. For example, the proximate end(s) of the robotic scope may include connection for connecting the robotic scope to a frame. In the example shown in FIGS. 1A-1D, the outer rigidizing member 112 and the inner rigidizing member 110 may each include controls and/or connections for coupling to steering inputs, air lines (e.g., suction), water lines, video lines (e.g., monitors, et.), and/or one or more tool channels. In some examples the robotic scope proximal end (or in the case of a dual rigidizing scope, each of the inner and outer members) may include a connector region, such as a cassette 257, shown schematically in FIG. 2. Each of the inner and outer members may include a separate cassette.

For example, the cassette may include connections for controlling steering, e.g., by one or more steering tendons, within the inner and/or outer members. For example, the cassette 257 can include disks 271a, 271b that may connect to cables 263a,b respectively, to steer (e.g., bend or deflect) the tip of the inner rigidizing member 210. Other steering mechanisms (e.g., pneumatics, hydraulics, shape memory alloys, EAP (electro-active polymers), or motors) are also possible. Again, in examples with different steering mechanisms, one or more disks in the cassette 257 (e.g., disks 271a, 271b) may be used to actuate the steering.

The cassette 257 can further include pressurization connections 203a, 203b that may connect to a pressure source for rigidizing the inner and/or outer members, respectively. Pressure (positive or negative, depending on the robotic scope, may pass through pressure lines 205z, causing the pressure in a pressure gap of the inner rigidizing member 210 to change (e.g., increase under positive pressure or decrease under negative pressure, i.e. vacuum), causing the rigidizing devices 210, 212 to become rigid. Activation of the pressure (positive or negative) may be applied sequentially and/or simultaneously, as illustrated in FIGS. 1A-1D. In some examples the cassette 257 can include pressure connectors 274a,b to sealingly couple to the one or more pressure sources. Other mechanisms causing rigidization of the robotic scope (e.g., inner and outer rigidizing members) are also possible.

The cassette 257 can include a connector for connecting to additional lumens and/or wiring in the outer or inner rigidizing device(s). For example, in FIG. 2 the cartridge 257 is coupled to the inner rigidizing member 110 and the connector 225y may include a connection for the delivery of both suction and water to the tip of the inner rigidizing device. The connector 225y may include an electrical connector to connect to a camera mounted to the tip of inner rigidizing device 110 to an external monitor and/or video processing unit. The connector 225y may include a mechanical connector that connects to a hollow tube (e.g., working channel) leading all the way to the tip of the inner rigidizing device 210. By including the connector 225y, the control of all components of the system 200 can be performed through the cassette 257 and may be manually or automatically controlled by the apparatuses described herein.

In some examples the control connections (e.g., disks 289, 271a, 271b, etc.) may be accessible from a bottom of the cassette 257. The control connectors may have features, such as splines, pins or teeth, to transmit torque. These features can allow them to be manipulated (e.g., by a drive system/sub-system). The drive system may be part of the link assembly described herein or it may be integrated with the link assembly. The same controller may operate the drive assembly and the other components of the apparatus (e.g., linear drive for the link assembly, height adjustment, pitch, etc.), including the rigidizing/derigidizing control.

Figure 3A:
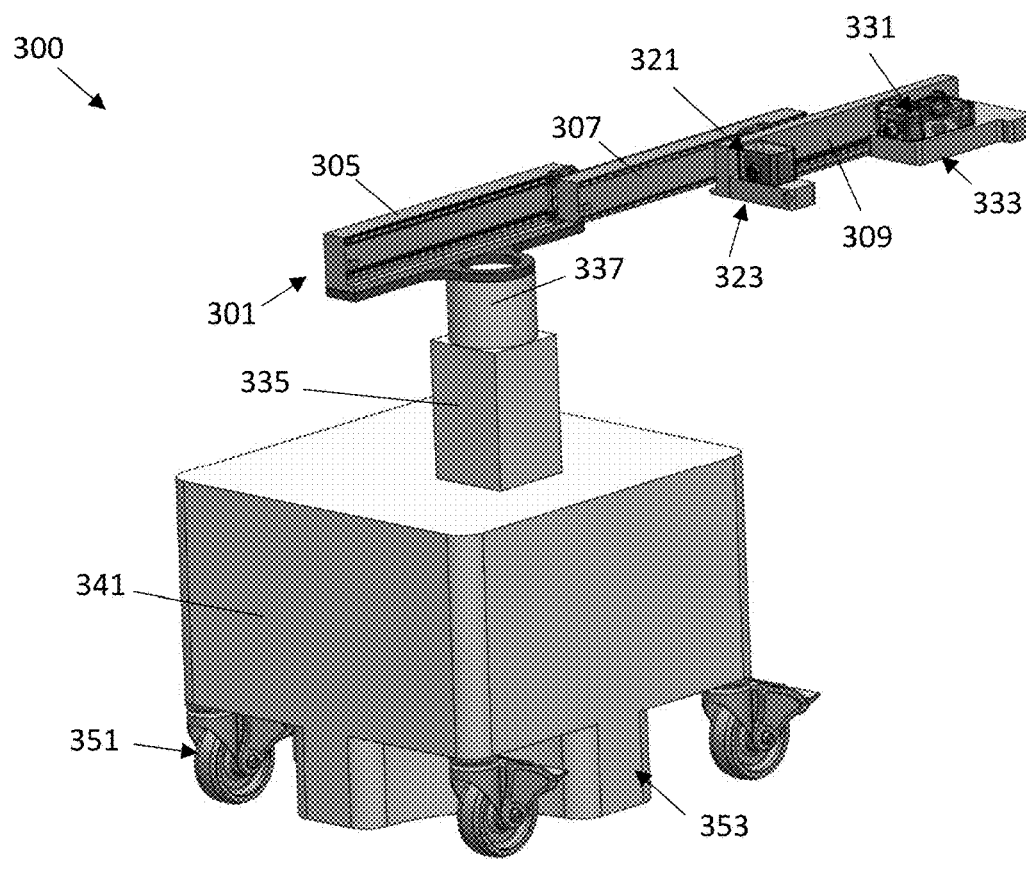
FIG. 3A shows an example of a system for dispensing (e.g., deploying) and controlling a nested robotic device in a first configuration.
Figure 3B:
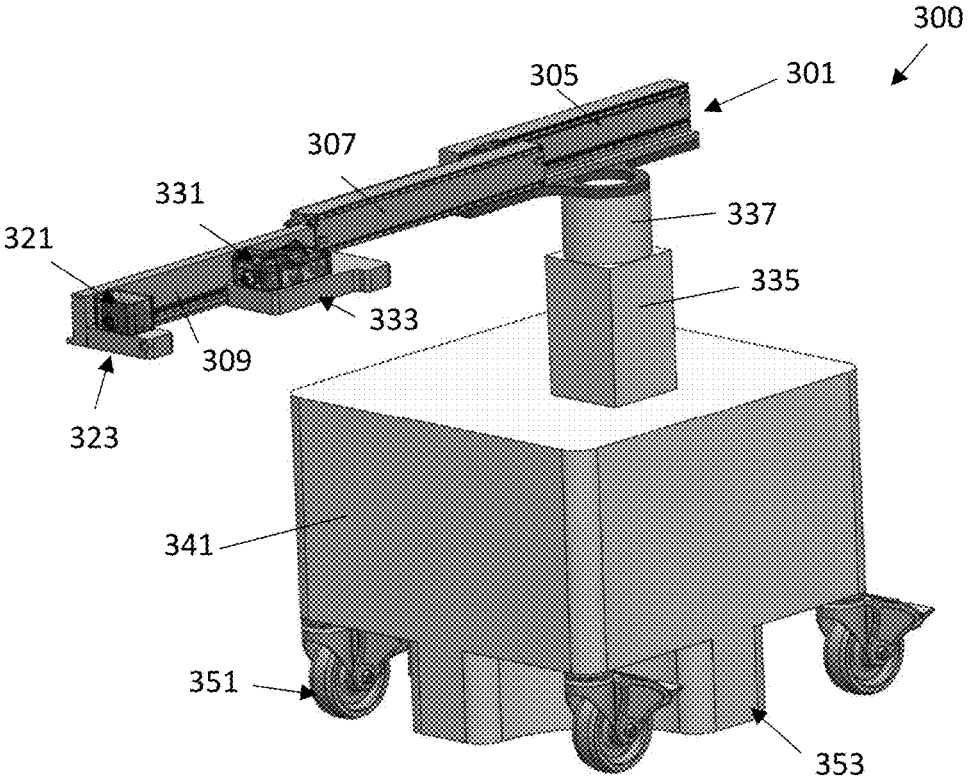
FIG. 3B shows the system for deploying and controlling a nested robotic device of FIG. 3A in a second configuration.

FIGS. 3A and 3B schematically illustrate a first example of an apparatus (e.g., system) for deploying and/or controlling a flexible tubular member. In many of the figures described herein, including in FIGS. 3A-3B, the apparatus is shown to be configured for use with a flexible tubular member configured as a nested endoscope that includes both an outer "overtube" an inner endoscope that may be moved proximally/distally relative to each other and may each be rigidized to guide and/or steer the device through the patient's body (as described above). However, it should be understood that these apparatuses may be used with any flexible tubular member, including those that are not nested and that do not rigidize (e.g., single-body endoscopes).

In FIG. 3A, the system 300 shown includes a base that my support the weight of the rest of the system, including any flexible tubular member attached to the system. The base 341 may be weighted so as to allow the telescoping link assembly and any attached flexible tubular member to cantilever distally or proximally away from the base, while remaining stable. The base may house one or more additional components, including power source, power conditioners, motors, pressure source/pressure supplies, controllers, control circuitry, etc. The base 341 may include wheels 351 to allow the apparatus to be moved and positioned relative to a patient's bed. In some examples the base 341 may include an anchoring region 353 that may be lowered and/or raised to allow or prevent movement. The wheels may be locking or lockable.

FIG. 3A shows the link assembly 301 configured as a vertically arranged link assembly including three links: a first link 305 (e.g., outer link or base link which may be coupled to the base), a second link 307 (e.g., an intermediate link) and a third link 309 (e.g., inner link). The first link is coupled to the yaw adjust arm 337 that is also configured as (or may be coupled to) a vertical lift arm 335 connecting the link assembly 301 to the baes 341. The system 300 shown in FIG. 3A also includes a mount assembly comprising a pair of mount regions 323, 333 that are coupled to the third link. In this example the first mount region 323 is configured as an overtube mount for coupling with an overtube of an endoscope. The overtube mount is located at or near the distal end region of the third link and includes an overtube drive assembly (e.g., driver) 321 that may interface with the overtube of the endoscope. In some examples, the overtube drive assembly may include drive components for controlling roll, for steering (optionally, in examples in which the overtube may be steered at the distal end), and/or pressure inputs/outputs for rigidizing/de-rigidizing. The overtube mount 323 may be configured to secure to the overtube portion separately from the inner endoscope. In some examples the overtube mount 323 may secure by including a securing mechanism such as a clamp, clasp, latch, lock, etc.

The second mount region 333 is configured as an inner endoscope mount and may also include an inner endoscope drive assembly 331, as shown. The inner endoscope drive assembly (driver) may interface with the inner endoscope member and may include the drive components described above in reference to FIG. 2, including steering components (e.g., for steering the distal end/tip region), roll control, pressure input/output (e.g., for rigidizing/de-rigidizing, etc.). The inner endoscope mount 331 may be configured to secure to the inner endoscope separately from the overtube, e.g., by including a securing mechanism such as a clamp, clasp, latch, lock, etc.

Figure 3C:
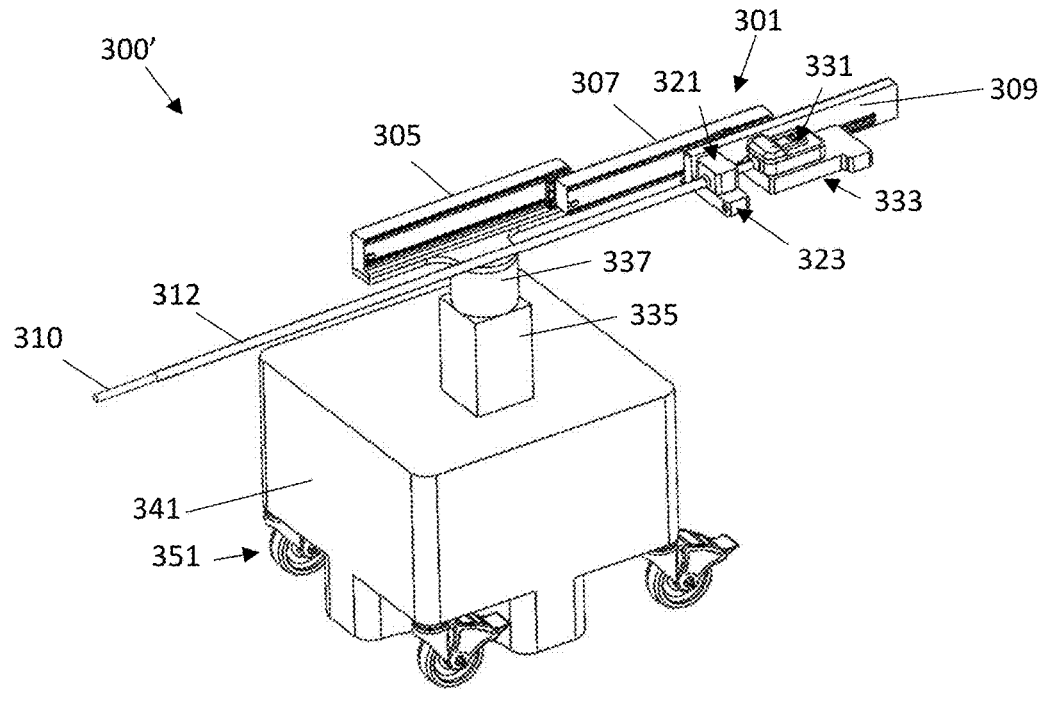
FIGS. 3C-3D show an example of a system similar to that shown in FIGS. 3A-3B including a flexible tubular member (e.g., a rigidizing nested overtube and inner endoscope).

FIG. 3C shows another example of a robotic system 300' including a telescoping link assembly 301 and base 341 similar to that shown in FIGS. 3A-3B. This example also includes a flexible tubular member attached to the system. The flexible tubular member in this example is configured as a nested pair of rigidizing devices similar to those shown in FIGS. 1A and 1B, including an outer overtube 312 and an inner endoscope 310. In this example the base 341 supports the telescoping link assembly 301 and the attached endoscope, so that the link assembly may smoothly move from a relatively low footprint centered neutral configuration to either a partially or fully extended configuration (as shown in FIG. 3B) or a partially or fully retracted configuration, as shown in FIG. 3C. The flexible tubular member may extend distally. In some examples, as shown and described in greater detail below, the apparatus may include one or more supports to prevent buckling or collapse of the flexible tubular member.

Figure 3D:
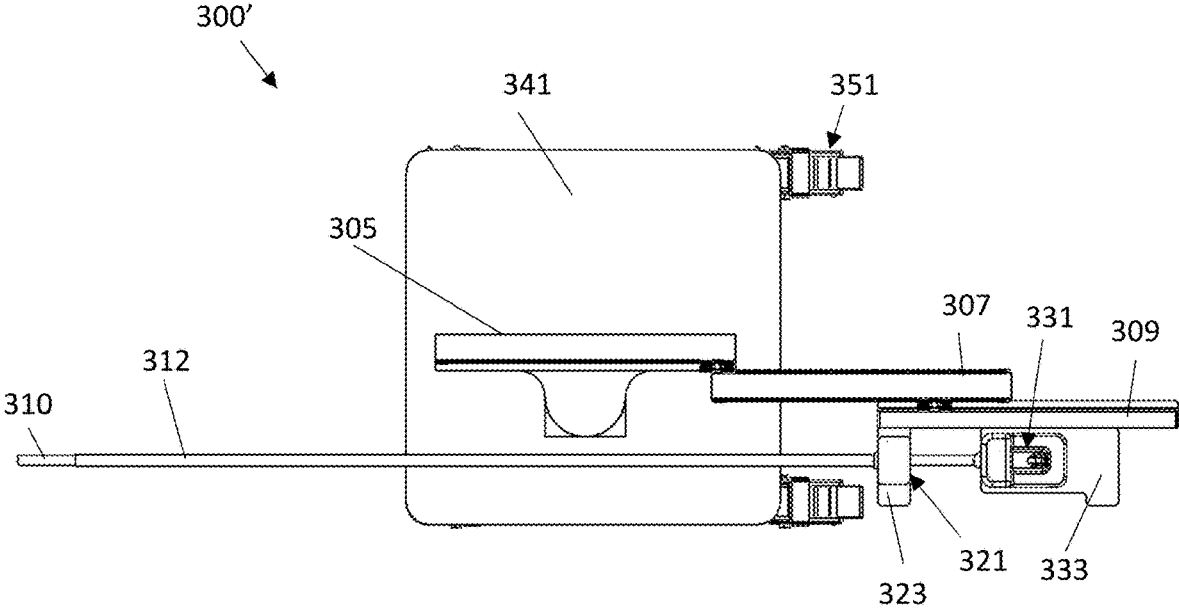

In FIGS. 3C and 3D, the link assembly 301 is configured as a vertically arranged link assembly, although any orientation of links may be used (e.g., horizontally-arranged, angled, hybrid horizontal/vertical/angled, etc.). Although three links 305, 307, 309 are shown, any number of links may be included. The flexible tubular member is coupled to the mount assembly coupled to the inner-most (third) link 309. The mount assembly includes a first mount region 323 to which the proximal end region of the overtube 312 is coupled. The first mount region may include a drive assembly 321 including one or more actuators for actuating movement of the elongate flexible member (e.g., overtube). For example, the first mount region 323 may include one or more roll actuators for rolling the overtube relative to the inner endoscope. In some examples the overtube may be steerable, e.g., by including one or more steering members (e.g., pull wires, tendons, etc.). The first mount region may include actuators for actuating the steering of the overtube. The overtube may be connected to a source of pressure (e.g. positive and/or negative pressure) for rigidizing/derigidizing the overtube. Thus, the first mount assembly may include a pressure port and may be configured to couple the overtube to the source of pressure. In some examples the source of pressure may be included with the system, or the system may be configured to couple to the source of positive and/or negative pressure.

The inner endoscope of the flexible tubular member is also connected to the mount assembly, by connection to the second mount region 333. The second mount region may include a second drive assembly 331 including one or more actuators for actuating the flexible tubular member (e.g., inner endoscope). For example, the second mount region 333 may include one or more roll actuators for rolling the inner endoscope relative to the overtube. The inner endoscope may be steerable, e.g., by including one or more steering members (e.g., pull wires, tendons, etc.). The second mount region may include actuators for actuating the steering of the inner endoscope. The inner endoscope may also be connected to a source of pressure (e.g. positive and/or negative pressure) for rigidizing/derigidizing the inner endoscope. Thus, the second mount assembly may include a pressure port and may be configured to couple the inner endoscope to the source of pressure.

The mount assembly may generally be configured to move the first mount region and the second mount region relative to each other, and therefore move the overtube and the inner endoscope relative to each other. Thus, the inner endoscope may be withdrawn partially or fully into the overtube may extend some distance out of the overtube (as shown in FIGS. 3C and 3D). FIG. 3D shows a top view of the system 300' of FIG. 3C.

As mentioned, the mount assembly (e.g., in some examples a first mount region and a second mount region) may be configured to secure to the flexible tubular member generally. The mount assembly may be configured to releasably couple to the flexible tubular member by one or more securing mechanisms such as clamps, clasps, latches, locks, etc. In the example shown in FIGS. 3C-3D, the mount assembly may be configured to separately couple the first mount region of the mount assembly to the overtube, and the second mount region may be configured to separately couple to the inner endoscope.

Figure 5A:
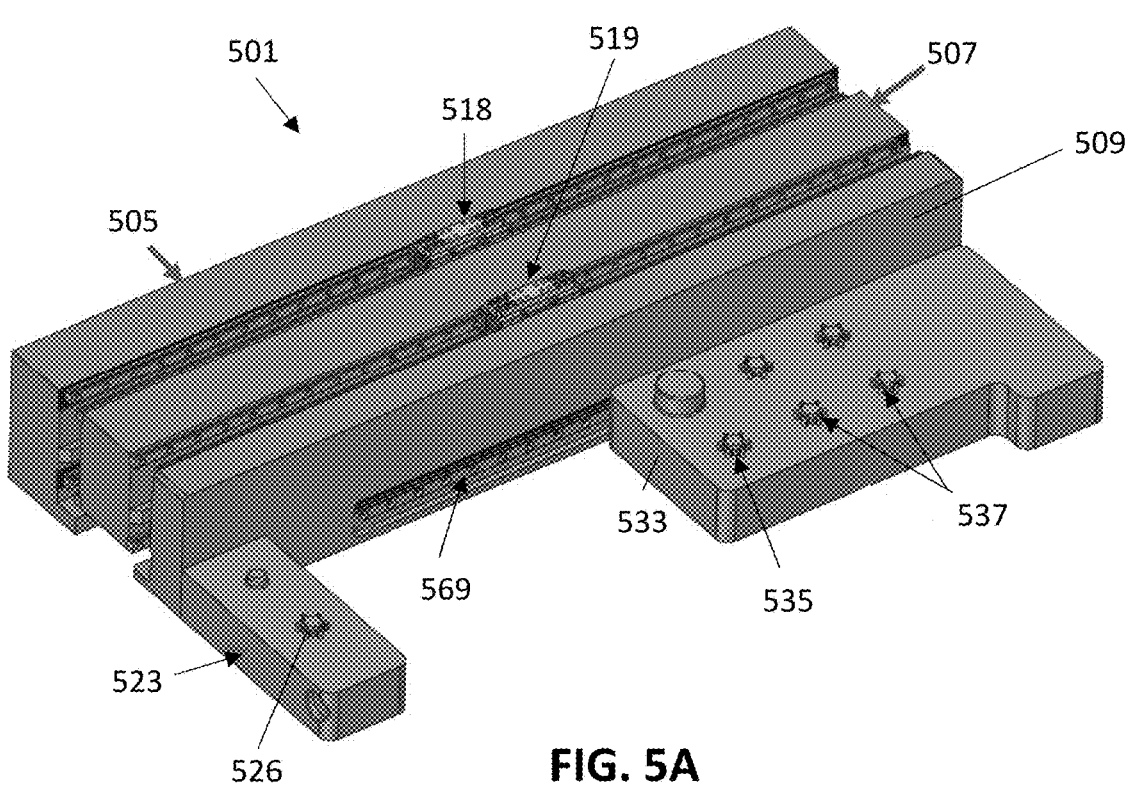
FIG. 5A shows an example of a set of vertically arranged linear links for use with a system for deploying a nested robotic device, including a first (e.g., overtube) linear driver and a second (e.g., endoscope) linear driver on an inner linear link.
Figure 5B:
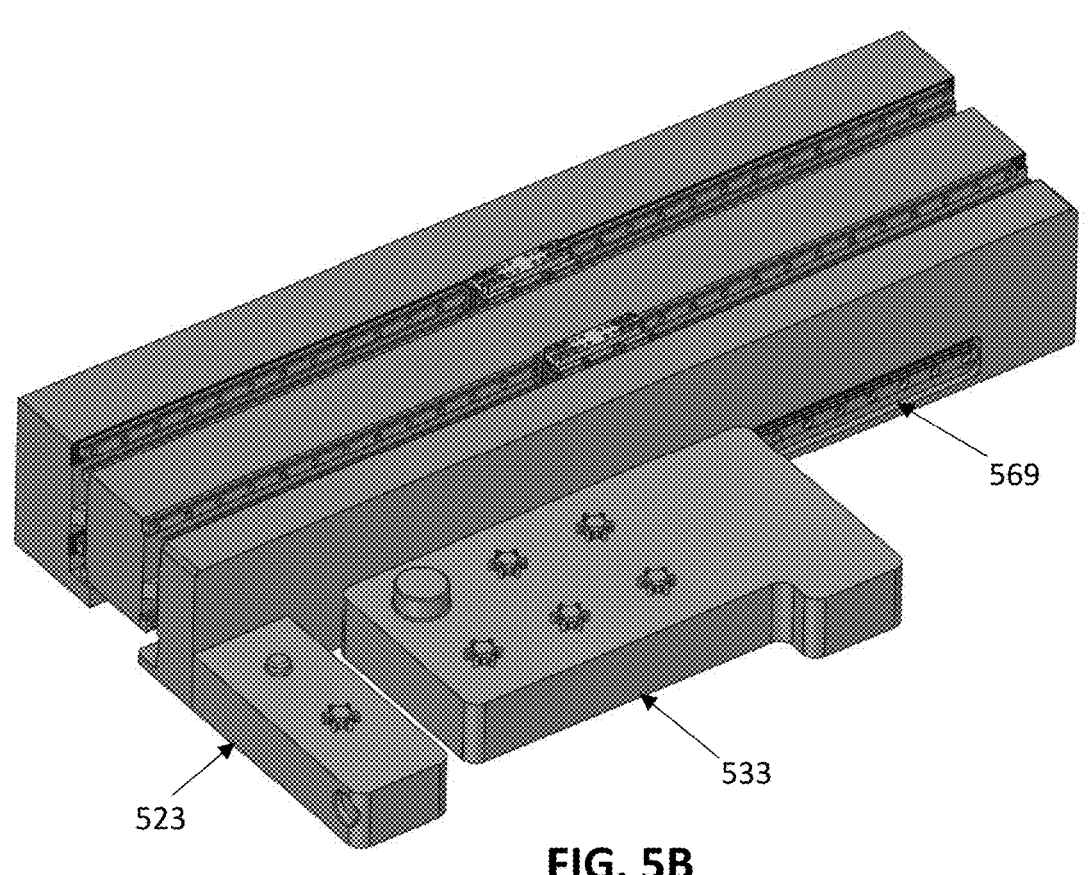
FIG. 5B shows the vertically arranged linear links of FIG. 5A with the second linear driver in a proximal position on the inner link.

FIG. 5A shows the link assembly of the apparatus in a fully proximal, retracted configuration. FIG. 5B shows the link assembly of the apparatus in a fully distal, extended configuration. As the link assembly moved proximally and distally (e.g., extends and retracts), the overtube mount moves as the link assembly moves, telescoping in and out. The inner endoscope mount 333 may be configured to move distally or proximally relative to the overtube mount (and the link assembly). In some examples the inner endoscope mount 333 may move relative to the outer overtube mount 323, as will be described in FIGS. 5A-5B, below.

Figure 4:
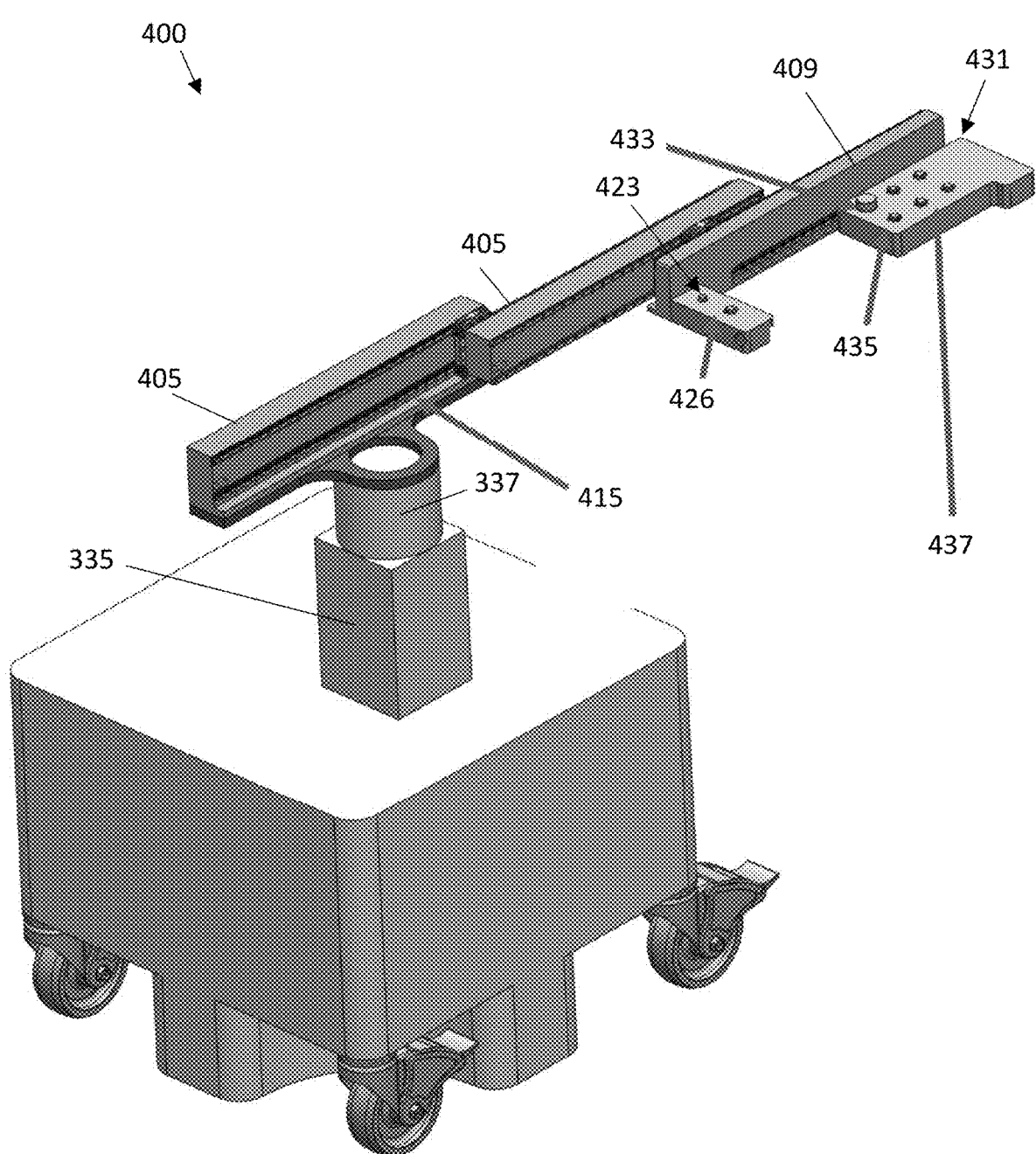
FIG. 4 shows an example of a system for deploying and controlling a nested robotic device, illustrating eight degrees of freedom.

In general, these apparatuses may include multiple (e.g., eight or more) degrees of freedom for the mount assembly and therefore the flexible tubular member. For example, FIG. 4 shows an example of a system 400 similar to that shown in FIGS. 3A-3B, in which the link assembly (including first 405, second 407 and third 409 links) moved in a proximal to distal direction when extending and retracting. Insertion and retraction may be driven by an overtube insertion motor 415 (e.g., a linear drive, such as a ball screw/nut assembly). The overtube mount 423 also includes an overtube roll motor 426. The inner endoscope mount 433 includes an endoscope driver 431 including an endoscope roll motor 435 and multiple steering motors 437. The link assembly is pivotally attached to a yaw adjustment arm 337 (which may be coupled to the base link 305 either directly or indirectly) and a vertical lift arm 335.

As mentioned above, in some examples the mount assembly for the flexible tubular member may include one or more separated drives for driving relative movement of an outer (e.g., overtube) and inner (e.g., inner endoscope) member of the flexible tubular member. FIGS. 5A-5B illustrate one example of a vertically-arranged link assembly that includes a mount assembly including an overtube mount 523 and a separately actuating inner endoscope mount 533. These regions of the mount assembly are configured to operate together, to provide relative motion between the first and second regions. The regions may be directly or indirectly coupled together. For example, in FIGS. 5A and 5B both the first mount region (the overtube mount 523) and the second mount region (endoscope mount 533) forming the mount assembly are coupled to the third link 590.

Thus, in this example of the vertically-arranged link assembly 501 includes a first link 505 (e.g., a base link), a second link 507 and a third link 509 that are vertically arranged relative to each other and are separated by shuttles (e.g., first shuttle 519 and second shuttle 518), that may be coupled to one or more bands and/or belts to permit them to coordinate extending and retracting. As mentioned, the mount assembly, e.g., first mount region and second mount region, are coupled to the third link. The first mount region 523 for the overtube is rigidly (e.g., fixed) coupled to the third link 509 and also includes an overtube driver (e.g., overtube roll motor 526) to drive roll of the overtube in the clockwise and/or counterclockwise direction. The second mount region 533 for the inner endoscope is proximal to the first mount and is configured to moved distally/proximally along an endoscope inserting track 569, and includes one or more drivers for operating the inner endoscope, such as an inner endoscope roll motor 535 and/or inner endoscope steering motors 537. In some examples the third link may include a drive for driving the second mount region. For example, in FIG. 5A the second mount region is shown fully distally relative to the first mount region; in FIG. 5B the second mount region is shown fully proximally relative to the first mount region.

Figure 6A:
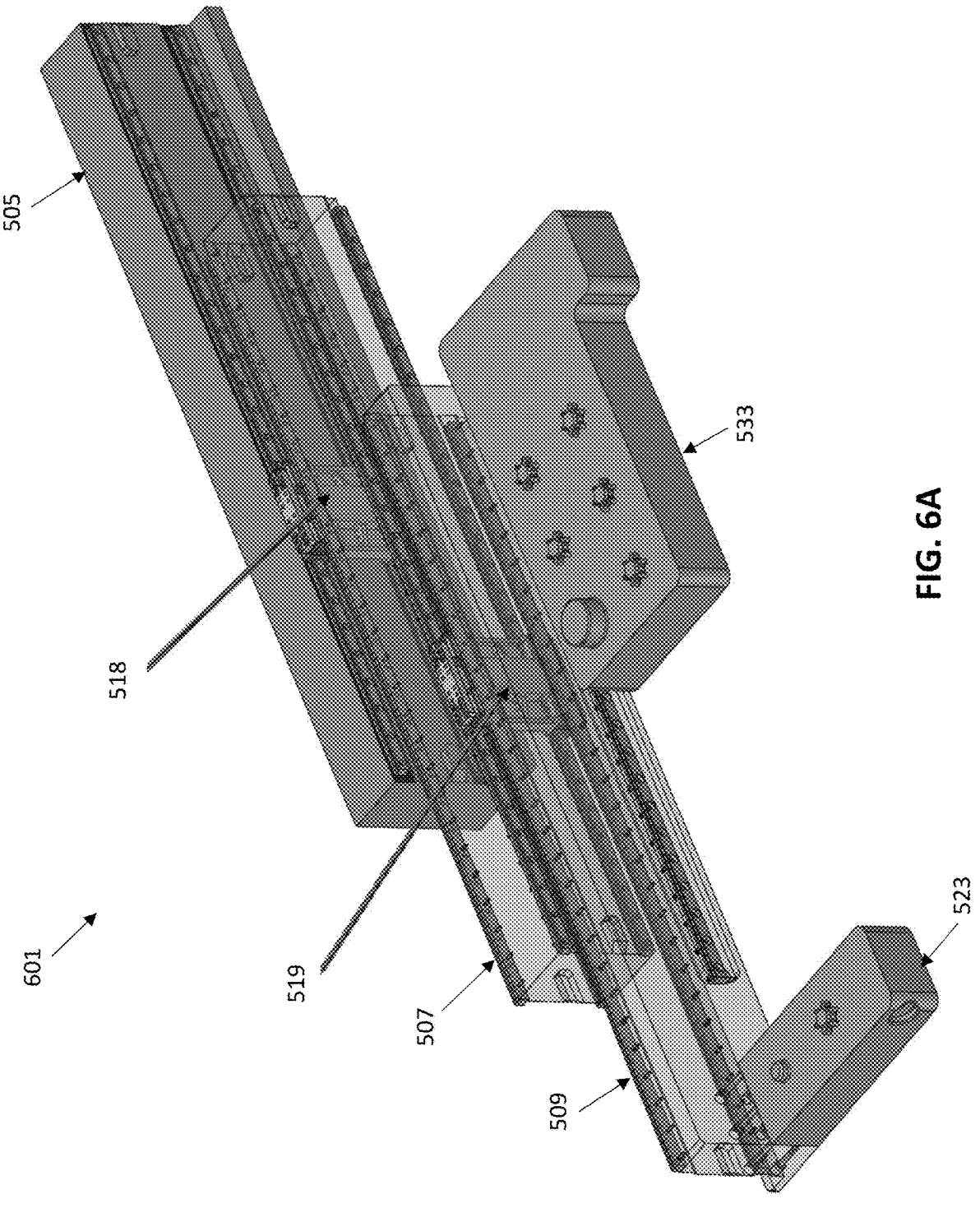
FIG. 6A shows an example of a set of vertically arranged assembly of linear links for use with a system for deploying and controlling a nested robotic device in a telescoping configuration.

FIGS. 6A-6D shows another example of a vertically-arranged link assembly 601 similar to that shown in FIGS. 5A-5B, illustrating an intermediate configuration of the set of vertically-arranged links. In general, any of the apparatuses described herein may include more than three links; for example, these apparatuses may include four links, five links, six links, etc. The additional links may be configured and controlled as shown here for three links. The outer link may be coupled to the base (directly or indirectly) and the inner link may be coupled to the mount assembly (including one or more mount regions). In FIG. 6A, the second and third links are shown as partially transparent. In general, the motion of the telescoping assembly may be achieved with a single drive (e.g. single motor) in any of these examples. The motion of the links may be coordinated using bands and/or synchronization belt(s). For example, the bands (and/or belts) may be steel bands. This is also illustrated schematically in FIG. 7A, illustrating the use of two shuttle links (proximal and distal).

Figure 6B:
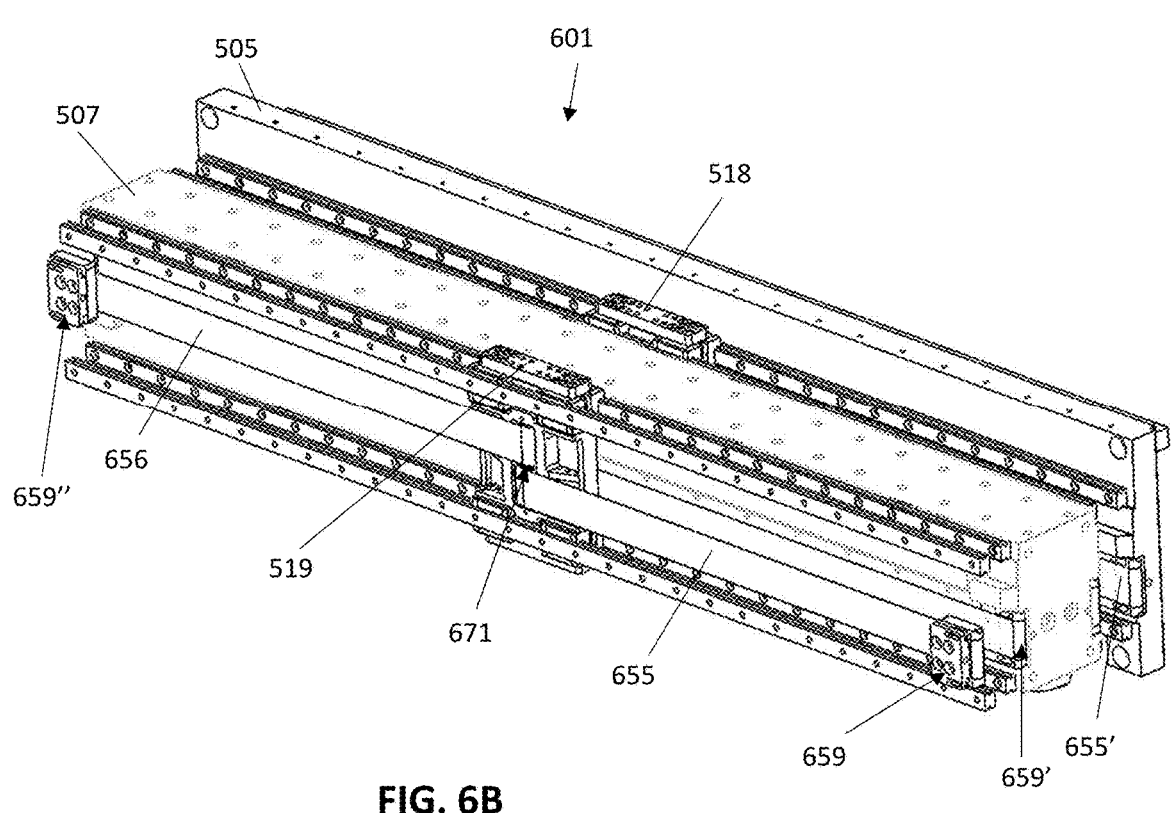
FIGS. 6B-6D illustrate views of an example of a portion of an assembly of linear links for controlling a flexible tubular member.
Figure 6C:
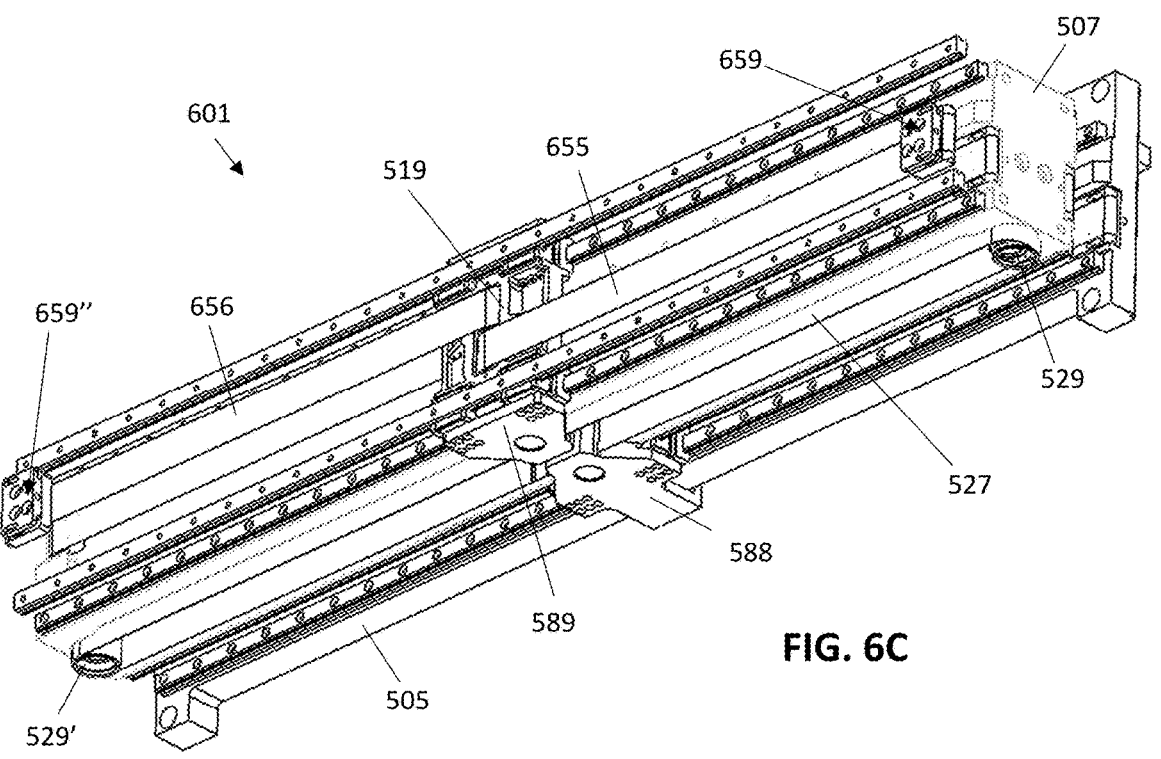
Figure 6D:
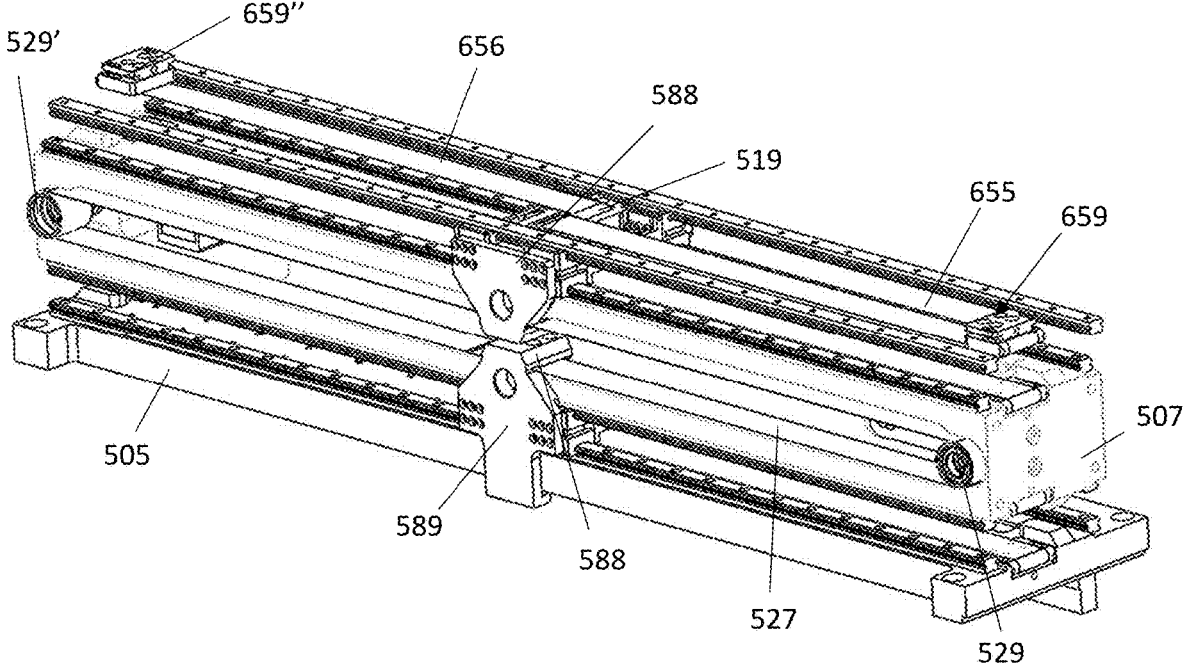

FIGS. 6B-6D illustrate additional detail of a portion of the vertically-arranged link assembly 601 of FIG. 6A, showing the first link 505 and second link 507 as well as the first shuttle 518 and the second shuttle 519. In FIGS. 6B-6D a pair of thin, flexible bands 655, 656 are shown coupled to the second shuttle 519, which will be positioned between the second link 507 and the third link (not shown). A similar arrangement of flexible bands 655' are connected between the first link and the second link. The bands 655, 656 are each coupled to the same respective ends of the second 507 and third links via attachment 659, 659', 659", and the bands wrap around a pulley surface (e.g., a cylindrical surface 671) in the shuttle 519. The bands may wrap around the pulley surface or different pulley surfaces that may be adjacent to each other.

FIGS. 6C and 6D also illustrate one example of a synchronization belt 527 that is shown coupled to the bottom of the second line 507, and to which both the first 618 and second 619 shuttles are coupled. The first shuttle is coupled to the synchronization belt by a bottom attachment 588 that wraps under the second link. The second shuttle is also coupled to the synchronization belt by a bottom attachment 589 that wraps under the second link. The synchronization belt may move (driving coordinated, but opposite movement of the attached shuttles) by rolling about a pair of synchronization pulleys 529, 529'.

Figure 7A:
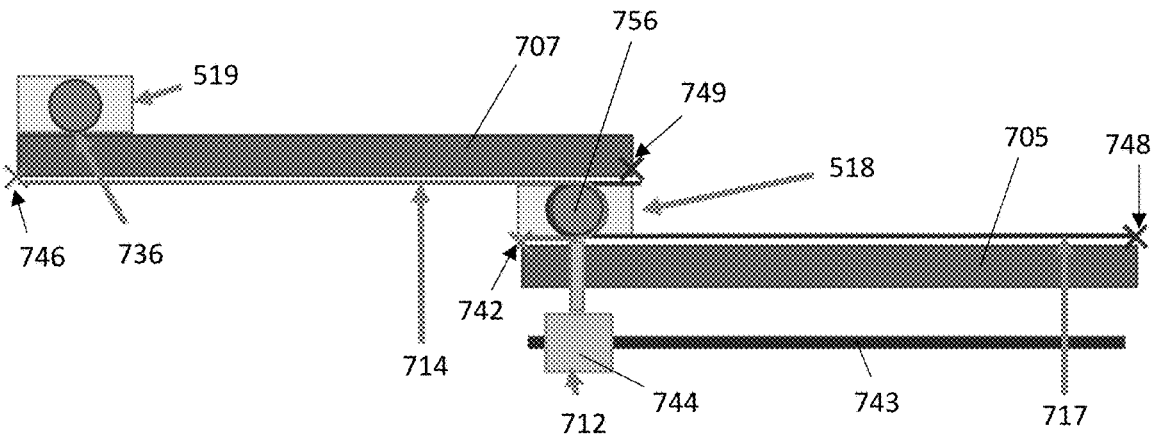
FIG. 7A schematically illustrates an example of a vertically-arranged assembly of linear links for use with a system for deploying a nested robotic device.
Figure 7B:
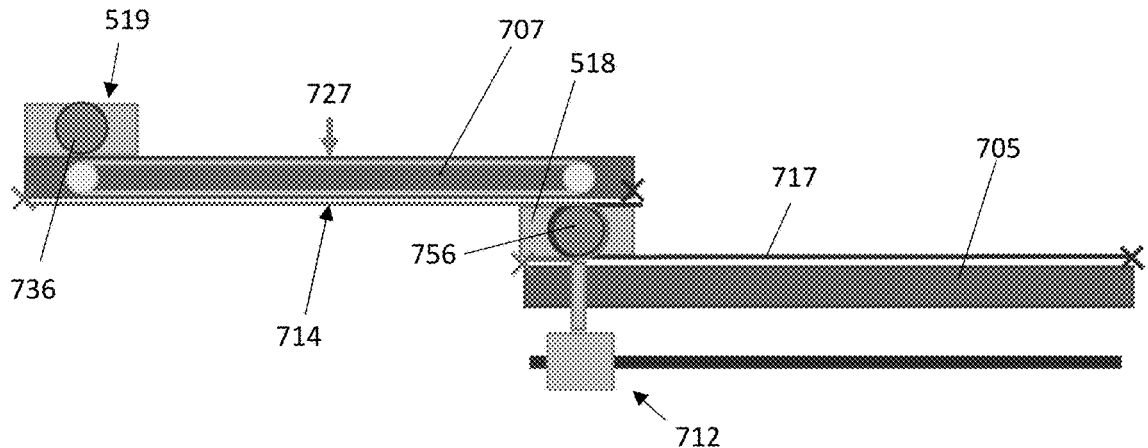
FIG. 7B schematically illustrates an example of a vertically-arranged assembly of linear links for use with a system for deploying and controlling a nested robotic device similar to that shown in FIG. 7A, further including a synchronization band to synchronize movement of the links coordinating movement of the shuttles between the links.

In FIGS. 7A-7B, a third (or more) link is not shown, for simplicity. In this example, the first link 705 may support and/or may contain a linear drive 712, shown in this example as a ball screw nut assembly. Rotation of the ball screw 743 drives the linear movement of the ball nut 744. The drive is coupled to the first shuttle 518, which may be coupled through the first link. Thus, the first shuttle may be driven proximally and distally by rotating the ball screw clockwise or counterclockwise. In FIG. 7A the first shuttle is configured to slide between the first link 705 (e.g., a base link) and the second link 707, however a pair of opposing flexible bands 717, 714 are attached to both the first link and the second link and wrap around a cylindrical surface (e.g., a pulley) within the first shuttle 518. For example in FIG. 7A, a first distal band 717 is attached at a first end 748 to a distal end region of the first link, e.g., on the inside surface facing the second link. The second end 749 of the first distal band 717 is attached to a distal end region of the second link. The first distal band extends between the first and second links and around the cylindrical (e.g., pulley) surface 756 of the first shuttle.

The first proximal band 714 is configured similarly, but is oriented in the opposite direction. For example, the first end of the first proximal band, which is also a flat ribbon (e.g., a flat metallic ribbon) is attached to the first link at the proximal end region 742, and passes around the cylindrical (e.g., pulley) surface 756 of the first shuttle, where it then connect to the proximal end region 746 of the second link (e.g. on the side facing the first link). Thus, the shuttle and the bands are configured to act as a pinon and rack interface between the first and second links. Moving the shuttle to the right (e.g., by action of the linear drive 712) moves the second link 707 to the right (retracting), while moving the shuttle to the left moves the second link 707 to the left (extending it distally). A similar configuration may be used between the second and third link for the second shuttle 519 (not shown). Alternatively, in some configurations the link assembly may include just a first and second link.

In some examples, in which more than two links are used, a synchronization belt may be used to synchronize the movement of a pair of shuttles. This is illustrated schematically in FIG. 7B (and FIGS. 7C-7E). FIG. 7B is otherwise similar to FIG. 7A, but includes a synchronization band 727 within the second link 707 that is coupled to both the first shuttle 518 and the second shuttle 519. The synchronization belt 727 may roll about pulleys at either end of the belt and is configured so that movement of the first shuttle 518 proximally result in movement of the second shuttle 519 distally and vice versa. Thus, the motion of the first shuttle is synchronized to the middle (second) link via the flexible bands, and to the motion of the second shuttle via the synchronization belt.

In some examples the motion may be transmitted from the driver (e.g., balls screw) to the flexible tubular member attached to the third link with a ratio of ball screw motion to tip motion that is 4:1, although other configurations having different ratio could be used.

In an of these examples the bands may also serve as a substrate and/or support for one or more electrical and/or electronic lines (wires, traces, etc.), allowing transmission of control and/or power through the link assembly (e.g., from the first link to the third, or more, links), even as the links move and telescope. The ribbon-shaped flexible bands may therefore provide a relatively constant path length between the links.

Note that although FIGS. 7A-7E illustrate an example in which both a first distal band 717 and a first proximal band 714 are used, in some examples only a first distal band or a first proximal band may be used. For example, the shuttle may include a channel in which the band is threaded to provide both a proximal and a distal reaction surface for the band; as the shuttle is driven either proximally and distally the band may be driven and slide against either reaction surface to move the second link.

Figures 7C, 7D, 7E:
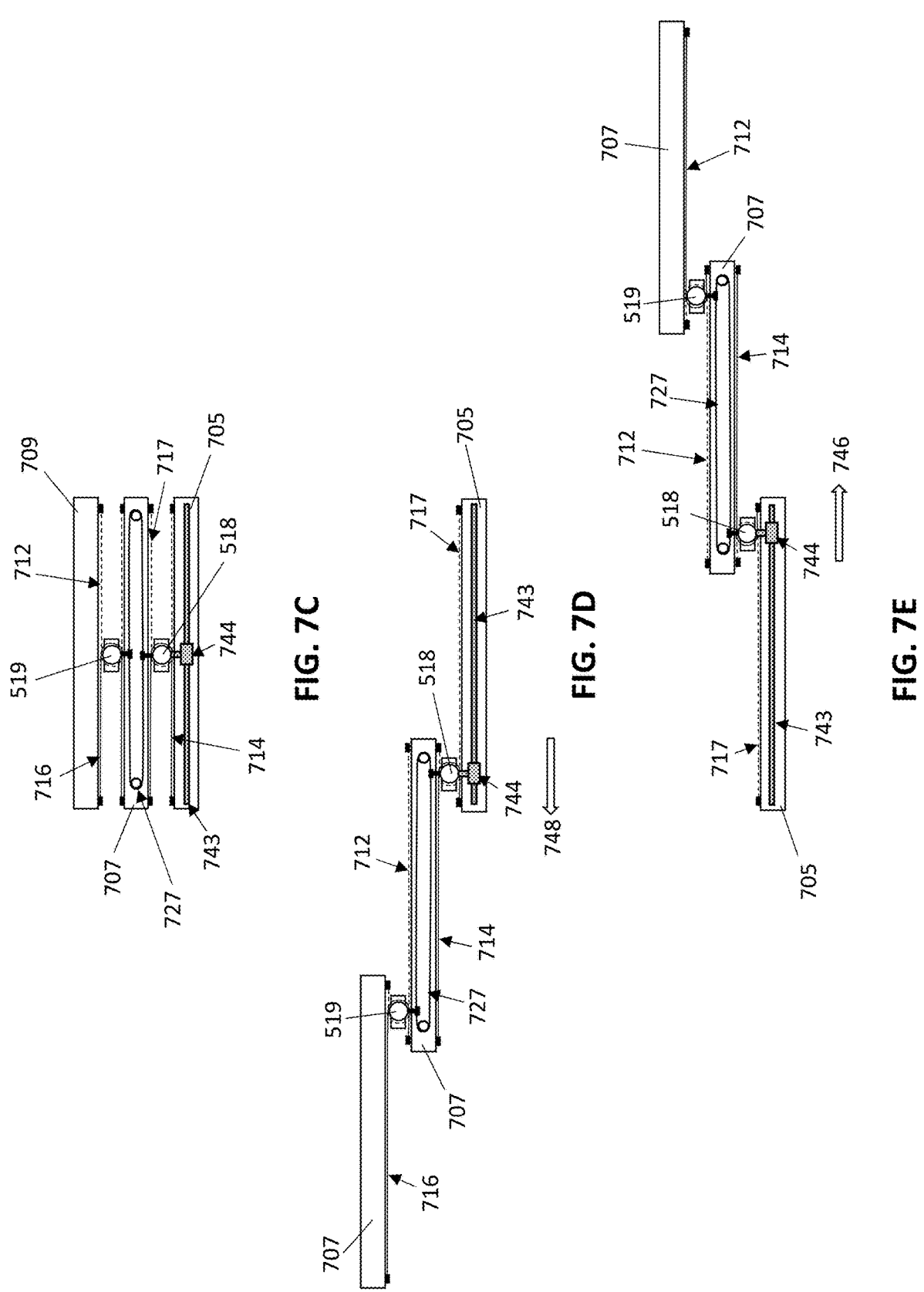
FIGS. 7C-7E schematically illustrate the bidirectional operation of a vertically-arranged assembly of linear links, showing an un-extended configuration (FIG. 7C) in which the inner and intermediate links are aligned with the outer link, a proximally extended configuration (FIG. 7D) in which the inner and intermediate links telescope proximally relative to the outer link, and a distally extended configuration (FIG. 7E) in which the inner and intermediate links telescope distally relative to the outer link.

FIGS. 7C-7E illustrate an example showing the operation of a set of three links of a vertically-arranged link assembly. In this example, the first link 705 includes (e.g., at least partially houses) the drive, e.g., the ball nut 744 and the ball screw 743, moving the first shuttle 518. A first distal band 717 and a first proximal band 714 extend between the first link 705 and the second link 707 and around the cylindrical surface of the first shuttle in opposite directions. The third link 709 is similarly connected to the second link 707 via a second distal band 712 and a second proximal band 716 that curves around a cylindrical surface (e.g., pulley) of the second shuttle 519. In addition, the first shuttle and the second shuttle are both coupled to a synchronization belt 727 within or coupled to the second link. Thus, as shown in FIG. 7D, when the linear drive drives the first shuttle proximally 748, the second and third links are each driven proximally, as shown. Similarly, as shown in FIG. 7E, when the linear drive drives the first shuttle distally 746, the second and third links are each driven distally in a coordinated telescoping movement.

FIGS. 7C-7E show a top view (looking down) of the vertically-arranged link assembly, and are not necessarily drawn to scale. FIG. 7C shows the vertically-arranged link assembly in a neutral position, having a relatively compact footprint, while FIGS. 7D and 7E show the fully telescoping configurations (either proximally or distally, respectively).

Although the examples described in FIGS. 6A-6D and 7A-7B show the shuttles slidably coupled to the links via a plurality of bands and/or belts, any appropriate movement coupling may be used. For example, the shuttles may be moved by a rack and pinion arrangement.

Figures 7F, 7H:
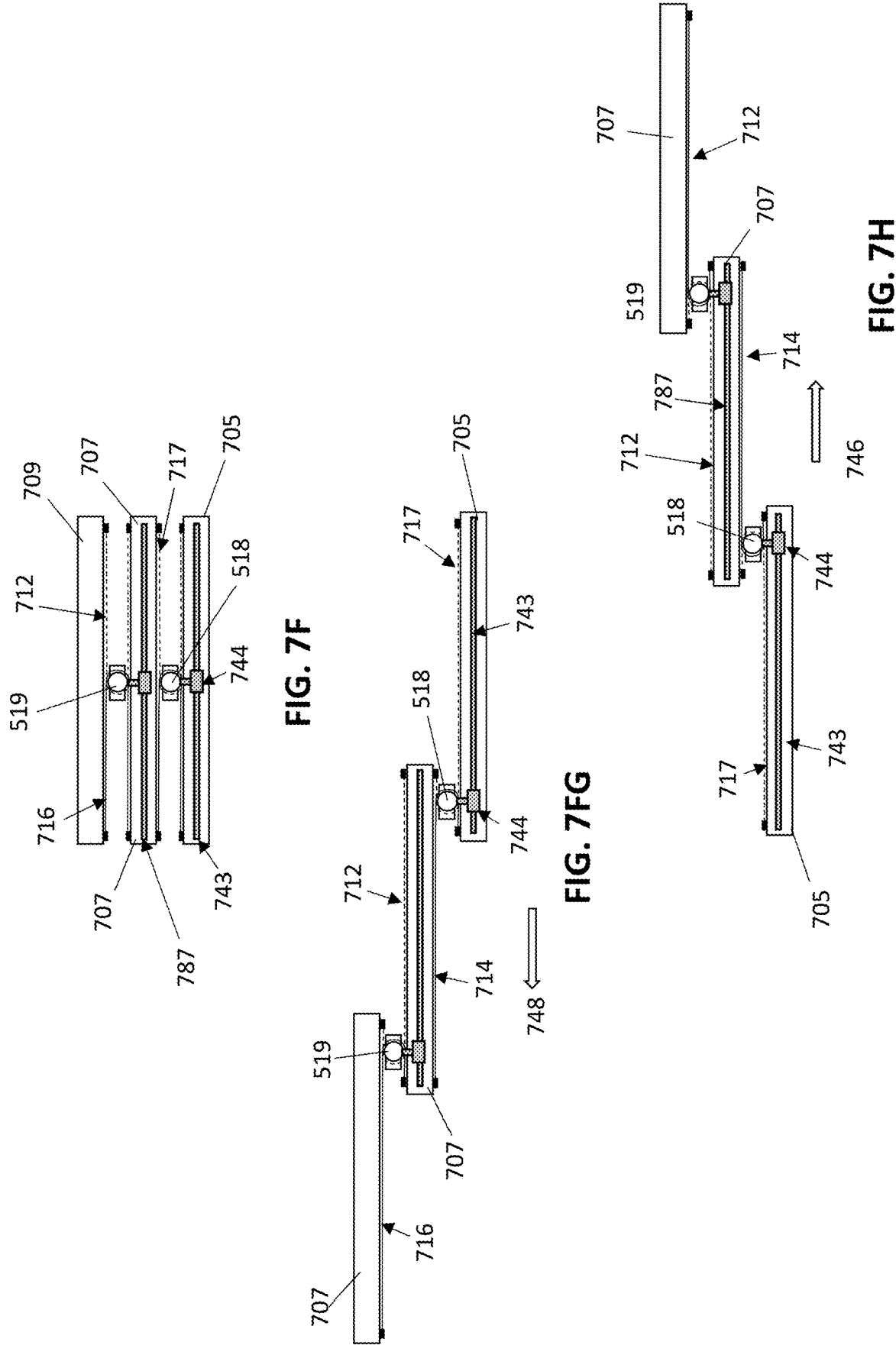

FIGS. 7F-7H illustrate another example showing the operation of a set of three links of a vertically-arranged link assembly similar to that shown in FIGS. 7C-7E, however the link movement is synchronized using a ball screw actuator rather than a synchronization band. In general, the telescoping movement of the links may be synchronized using any appropriate movement-synchronizing mechanism, including a band, ball-screw, etc. In this example, the first link 705 includes (e.g., and may at least partially house) the drive, e.g., a ball nut 744 and the ball screw 743, moving the first shuttle 518. A first distal band 717 and a first proximal band 714 extend between the first link 705 and the second link 707 and around the cylindrical surface of the first shuttle in opposite directions. The third link 709 is similarly connected to the second link 707 via a second distal band 712 and a second proximal band 716 that curves around a cylindrical surface (e.g., pulley) of the second shuttle 519. In addition, the first shuttle and the second shuttle are both coupled to a ball screw actuator 787 within or coupled to the second link. Thus, as shown in FIG. 7G, when the linear drive drives the first shuttle proximally 748, the second and third links are each driven proximally, as shown. Similarly, as shown in FIG. 7E, when the linear drive drives the first shuttle distally 746, the second and third links are each driven distally in a coordinated telescoping movement.

FIGS. 7F-7H show a top view (looking down) of the vertically-arranged link assembly, and are not necessarily drawn to scale. FIG. 7F shows the vertically-arranged link assembly in a neutral position, having a relatively compact footprint, while FIGS. 7G and 7H show the fully telescoping configurations (either proximally or distally, respectively).

FIGS. 7F-7H illustrate another example showing the operation of a set of three links of a vertically-arranged link assembly similar to that shown in FIGS. 7C-7E, however the link movement is synchronized using a ball screw actuator rather than a synchronization band. In general, the telescoping movement of the links may be synchronized using any appropriate movement-synchronizing mechanism, including a band, ball-screw, etc. In this example, the first link 705 includes (e.g., and may at least partially house) the drive, e.g., a ball nut 744 and the ball screw 743, moving the first shuttle 518. A first distal band 717 and a first proximal band 714 extend between the first link 705 and the second link 707 and around the cylindrical surface of the first shuttle in opposite directions. The third link 709 is similarly connected to the second link 707 via a second distal band 712 and a second proximal band 716 that curves around a cylindrical surface (e.g., pulley) of the second shuttle 519. In addition, the first shuttle and the second shuttle are both coupled to a ball screw actuator 787 within or coupled to the second link. Thus, as shown in FIG. 7G, when the linear drive drives the first shuttle proximally 748, the second and third links are each driven proximally, as shown. Similarly, as shown in FIG. 7E, when the linear drive drives the first shuttle distally 746, the second and third links are each driven distally in a coordinated telescoping movement. This actuation scheme may be repeated two or more times in series to achieve the movement.

FIGS. 7F-7H show a top view (looking down) of the vertically-arranged link assembly, and are not necessarily drawn to scale. FIG. 7F shows the vertically-arranged link assembly in a neutral position, having a relatively compact footprint, while FIGS. 7G and 7H show the fully telescoping configurations (either proximally or distally, respectively).

Figures 7I, 7J, 7K:
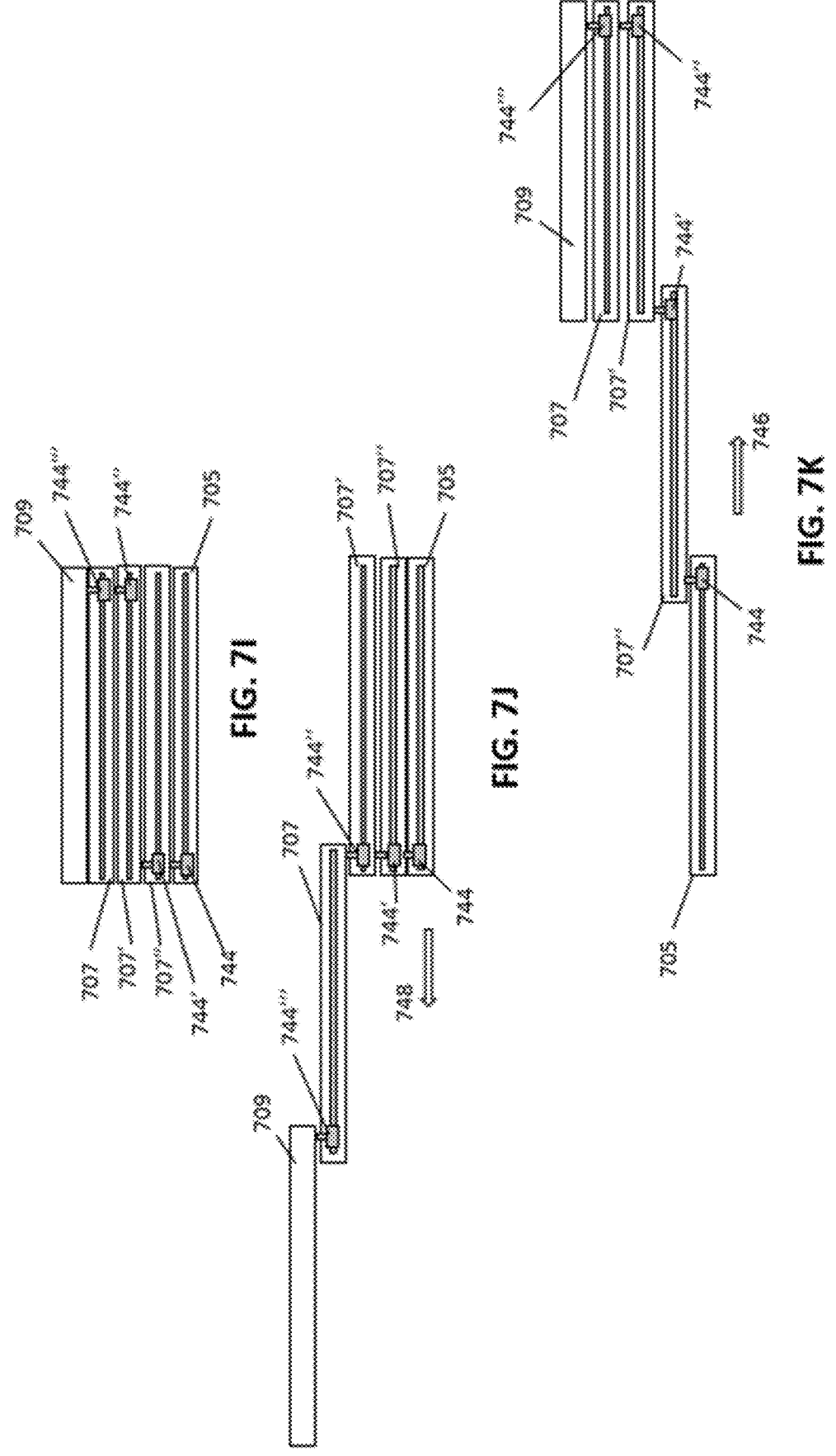
FIGS. 7I-7K schematically illustrate the bidirectional operation of an assembly of linear links, showing an un-extended configuration (FIG. 7I) in which the inner and the three intermediate links are aligned with the outer link, a proximally extended configuration (FIG. 7J), and a distally extended configuration (FIG. 7K).

FIGS. 7I-7K illustrate another example showing the operation of a link assembly also configured for bidirectional telescoping movement of a set of links of a link assembly similar to that shown in FIGS. 7C-7E and 7F-7H, however the link movement is synchronized using plurality of mechanical movement coupling members, comprising a ball screw actuator in this example. This configuration does not include a separate synchronization band. In general, the telescoping movement of the links may be synchronized by operation of the ball screws to which each stage is coupled to the adjacent stage. Thus, compared to the examples shown in FIGS. 7C-7K, all of the bands have been replaced with ball-screw actuators and the shuttles are instead additional intermediate links. This may accommodate the stroke of the ball screws. The ball screws/nuts may be biased to the ends of the links in the nominal (centered) position, as shown in FIG. 7I. For example, the first link 705 includes (e.g., and may at least partially house or is coupled to) the drive, e.g., a ball nut 744 and the ball screw 743, moving the first intermediate link 707" that also houses or is otherwise coupled to a ball nut 744' and ball screw. This pattern may be repeated for the second 707' and third 707 intermediate links. Thus, as shown in FIG. 7J, when the linear drive drives the first shuttle proximally 748, the top links are each driven proximally, as shown; the links may be arranged so they extend over the top of the bed/table but by a minimal amount to allow maneuvering near the patient. Similarly, as shown in FIG. 7K, when the linear drive drives the first shuttle distally away from the patient 746, the top links (third link 709 and intermediate link 707) are each driven distally in a coordinated telescoping movement.

Figure 7L:
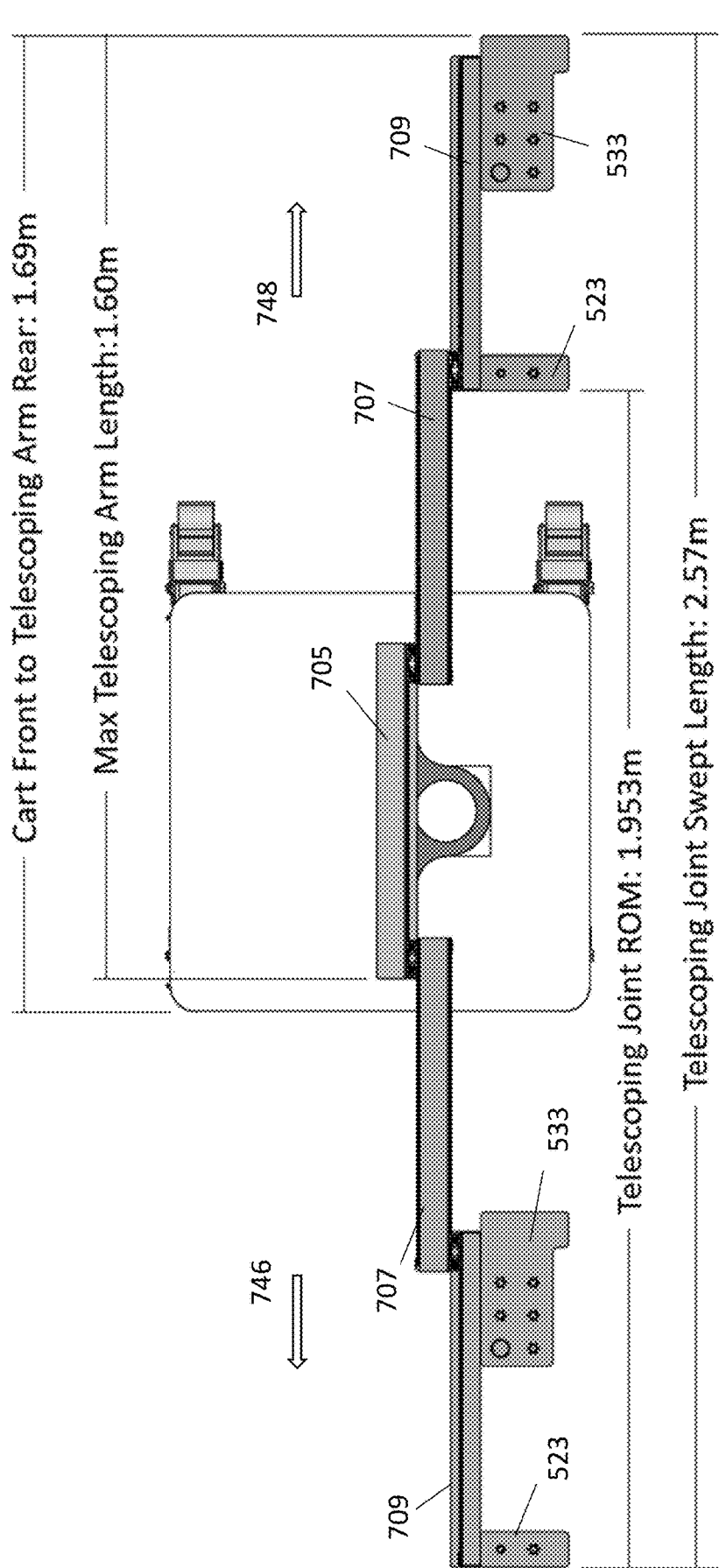
FIG. 7L shows another example of a top view of an assembly of linear links of a robotic apparatus, showing maximum telescoping length in both a proximal and distal direction.

The assembly of liner links may be any appropriate size and may be configured to give a working range of movement during operation. As mentioned, in some configuration the apparatus may be configured to sweep the overtube (outer member of the telescoping assembly) over a length of between about 0.2 m and 3 m, e.g., between about 0.5 m and 2.2 m, etc., in variations in which the overtube mount 523 is fixed to the first link (this range may be larger if the overtube mount may move relative to the link assembly). Because the inner endoscope mount 533 is linearly translating relative to the first link 709 of the link assembly, the sweep length of the endoscope mount may be larger than the sweep length of the overtube mount 523, e.g., between about 0.2 m and 3.5 m, e.g., between about 0.5 m and 2.6 m, etc. FIG. 7L shows a top view of an example of an assembly of linear links of a robotic apparatus, including exemplary dimensions. In FIG. 7L, both extension to the right 746 (e.g., distal extension) and extension to the left 748 (e.g., proximal extension) are shown. For example, in FIG. 7L the distance between the cart (base) front and the proximal end of the first link 709 may be, e.g., between 0.25 and 2 meters; in the specific, non-limiting example shown in FIG. 7L, the distance is shown as about 1.69 m, thus the maximum proximal extension is about 1.6 m. In the same non-limiting example, the maximum range of motion (ROM) of the overtube mount, and therefore the proximal end of the overtube, is shown as about 1.953 m, thus the sweet length of the inner member (e.g., the inner endoscope mount 533) is about 2.57 m.

Other mechanical movement coupling elements may be used, including software or firmware; in some cases each link may be moved by a driver (e.g., motor, etc.) that may be integrated (e.g., coupled, contained within, etc.) to the link.

Figure 8:
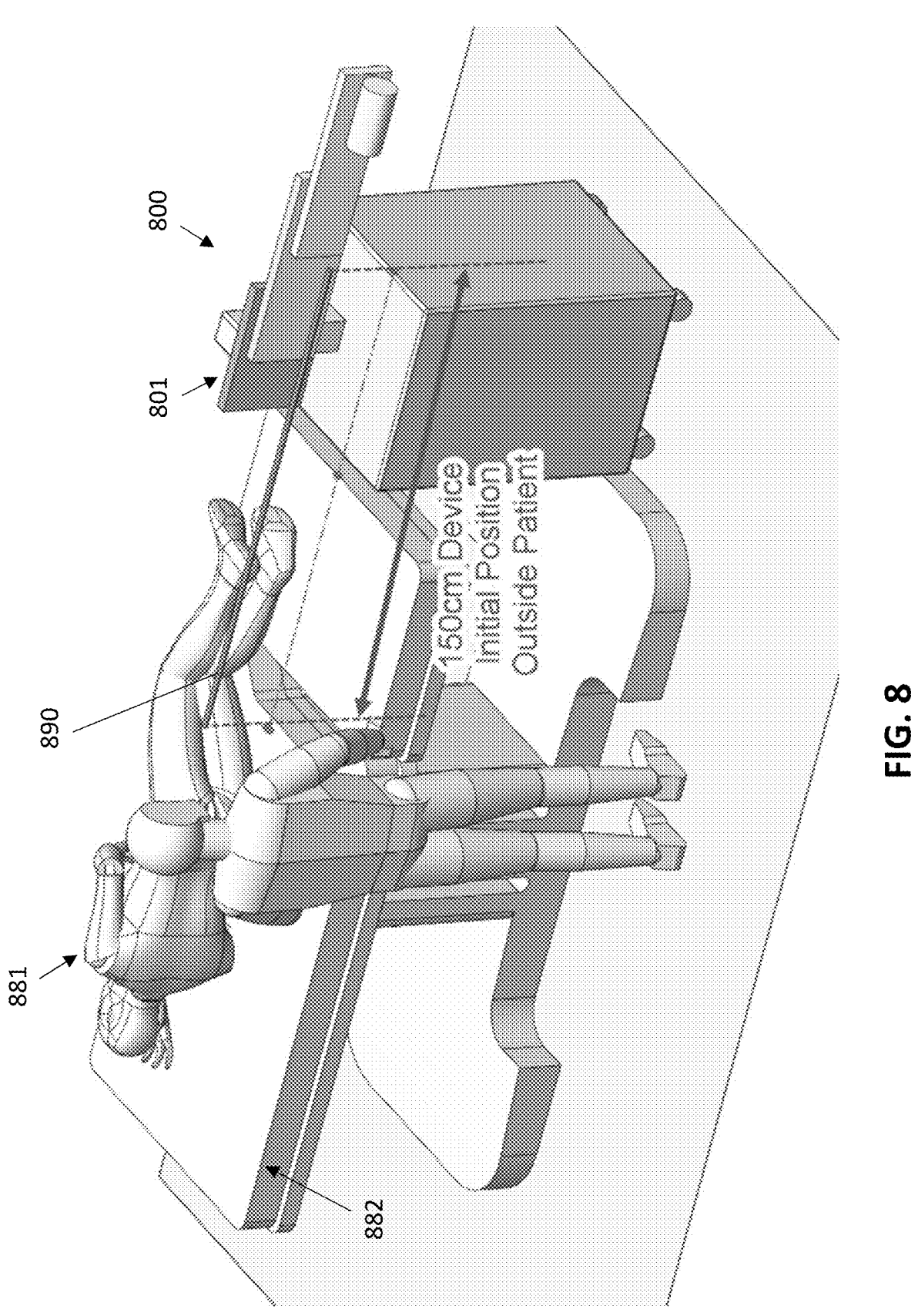
FIG. 8 illustrates one example of an arrangement between a patient, patient bed (e.g., table, cart, etc.), a nested robotic device, and a system for deploying a nested robotic device as described herein.

FIG. 8 illustrates one example of a method of using a system 800 for deploying and/or controlling a flexible tubular member as described herein, including a vertically-arranged link assembly 801 that is schematically shown engaged with an endoscope 890 to deploy and control the endoscope as it is inserted into a patient 881. The patient is shown lying on his side on a table 882. In this example the device is initially positioned at the foot of the bed, and the system must hold the endoscope, which has a length of about 1.5 meters, initially outside of the patient's body before being inserted into the patient's rectum, to perform a colonoscopy. The links of the vertically-arranged link assembly 801 are arranged perpendicular to the ground, and may telescope distally initially (as shown) to provide sufficient clearance outside of the body, while still allowing the system to be placed adjacent to the edge of the table/bed 882. In addition, the vertical arrangement of the links allows the endoscope device to be positioned in-line with the patient at the height of the insertion point. Thus, this configuration may have a minimal distance from the device axis (e.g., endoscope axis) to the top of the bed mattress.

Figure 9:
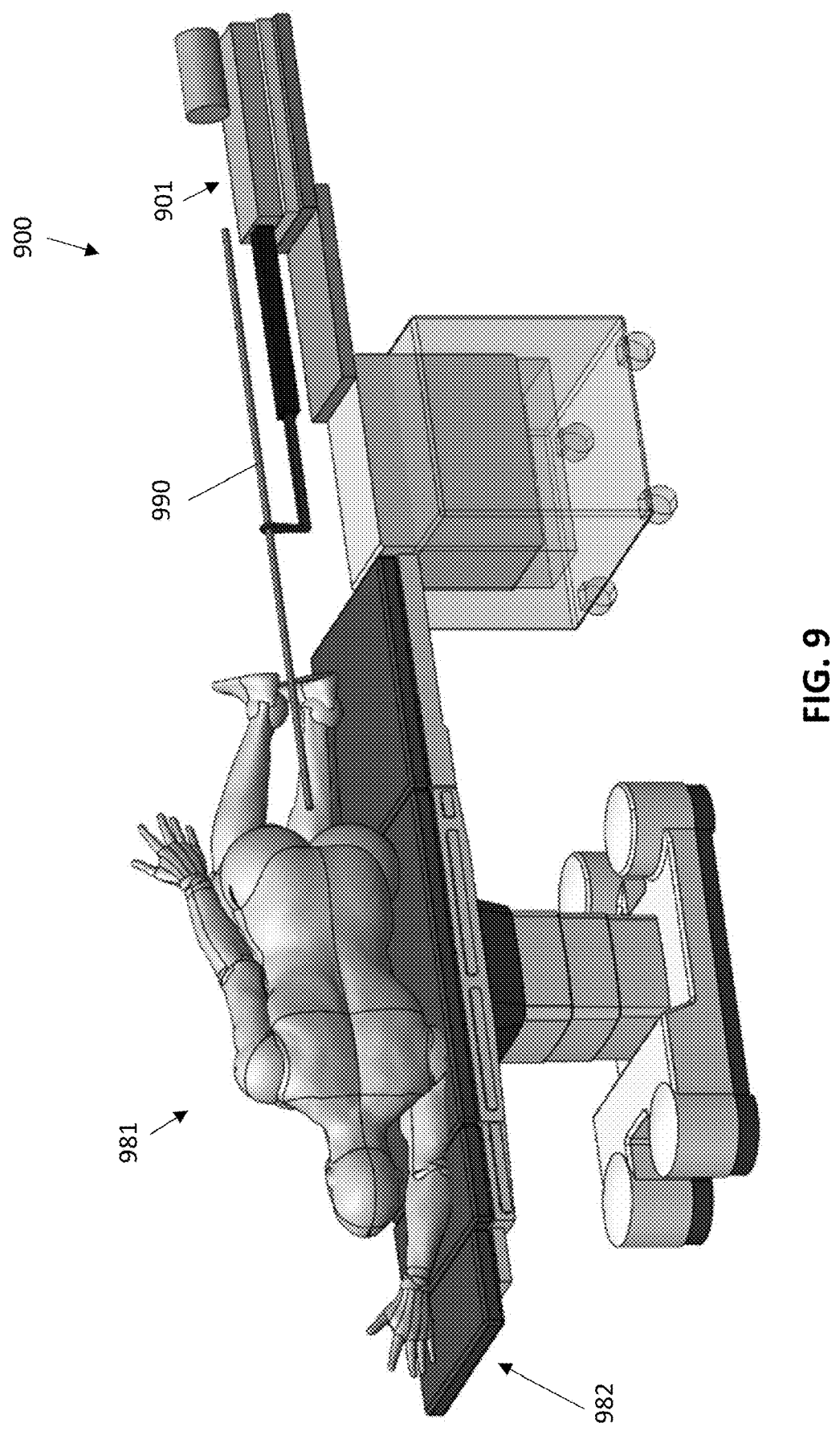
FIG. 9 schematically illustrates an example of a system for deploying a nested robotic device in which the linear link assembly is horizontally (rather than vertically) arranged.

As an alternative, the configurations described herein may instead by used with the links arranged horizontally (e.g., in parallel with the ground), as shown in FIG. 9. In FIG. 9, the system 900 includes a set of horizontally arranged linear links 901 that may engage with the proximal end of an endoscope 990 (e.g., robotic, rigidizing endoscope, as described herein). In FIG. 9, the device may be retracted and extended, as described above for the vertically-arranged link assembly, but proximal advancement of the device may receive interference from the bed 982 (e.g., mattress), limiting the approach angle when inserting into the patient 981.

For example, FIGS. 10A-10C illustrate representative distance between the device axis (e.g., long axis of the endoscope) and the top of the table or mattress (e.g., bed) relative to the patient anatomy. FIG. 10A illustrate the patient and bed position and dimensions for a lower GI, left lateral approach. In this example the patient is shown on their side on the bed 982, in a patient longitudinal position 1075. The device axis 1078 needed for insertion into the rectum from this position requires a height above the bed as shown 1076, which may be within an average range. This height may be significantly higher than the height for a lower GI, supine approach, as shown in FIG. 10B. In this example, the patient is lying in a longitudinal position 1075' on their back, and the height of the device axis 1078' above the bed 1076' is lower than in 10A.

FIG. 10C illustrates an example of an upper GI procedure using this system, in which the patient is in a left lateral position (prone and supine, with their head turned approximately 90 degrees). In this example, the device axis 1078" for accessing the patient's mouth is typically about the height of the patient's head above the mattress 1076".

Figure 11:
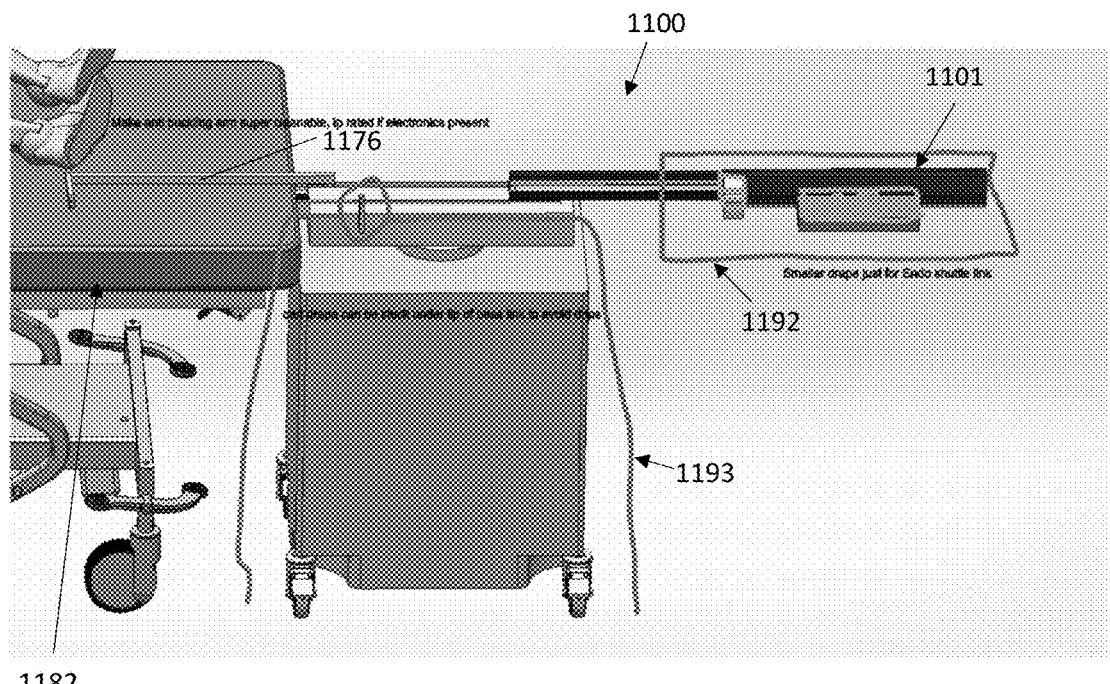
FIG. 11 schematically illustrates an example of a draping system for protecting a system for deploying a nested robotic device during use.

In general, any of these systems and apparatuses may be configured for use with a drape, shield or screen to prevent contamination or soiling of the apparatus, For example, FIG. 11 schematically illustrates an example of draping a system as described herein to limit soiling of the device by patient fluids, which may help minimize cross-contamination between patients. In some examples these systems may be draped as shown to from a non-sterile barrier to minimize soiling or excessive soiling of the robotic system. In some examples the draping 1193 may be configured to provide a sanitary but not sterile cover for the system, including the base and/or the link assembly 1101 (e.g., the vertically-arranged link assembly). The draping may be two or more parts, as shown, including a first part that covers the base and a second part that covers the link assembly. Alternatively, in some examples, the system, or at least the vertically-arranged link assembly, may be covered with a sterile drape. As mentioned above, any of these apparatuses and methods may include sterilizing and/or wrapping in a sterile outer cover.

Figure 12:
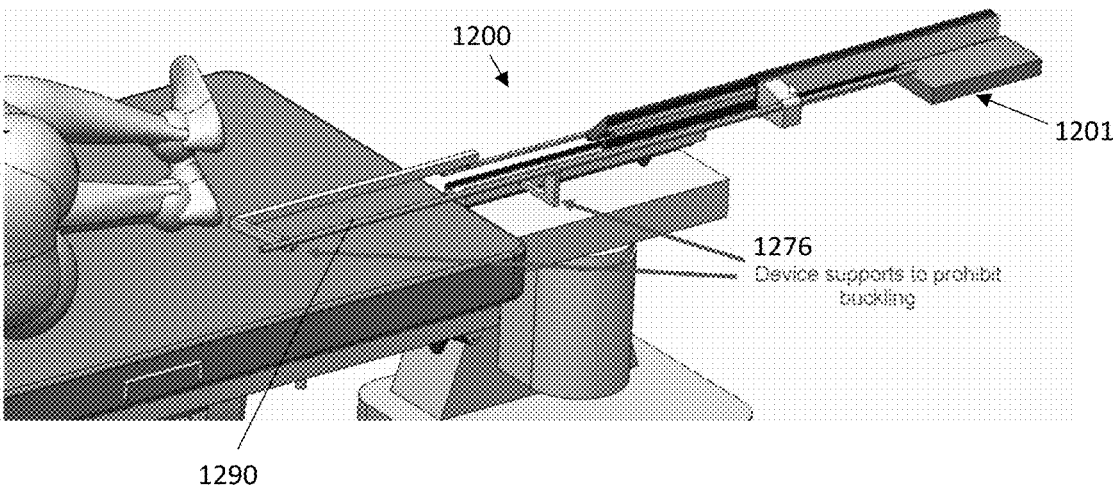
FIG. 12 schematically illustrates an example of a support (e.g., support arm(s)) for use with a system for deploying a nested robotic device.

Any of these apparatuses may include a support arm 1176 that may extend from the vertically-arranged link assembly 1176, as shown in FIG. 11 and in FIG. 12. The endoscopes described herein may prevent or limit the buckling of the endoscope under compressive loads. For example, in FIG. 12 the system 1200 includes a vertically-arranged link assembly 1201 from which an elongate support arm 1276 may extend and may engage with an endoscope 1290 as just discussed, to prevent or inhibit buckling. In some examples the support arm 1276 may include multiple supports for the devices along their length to provide parallel paths to mechanical ground. These supports could be passive (sliding/rotating) or motorized. A laser pointer can be attached to an anti-buckling support, or another distal part of the machine.

Figure 13:
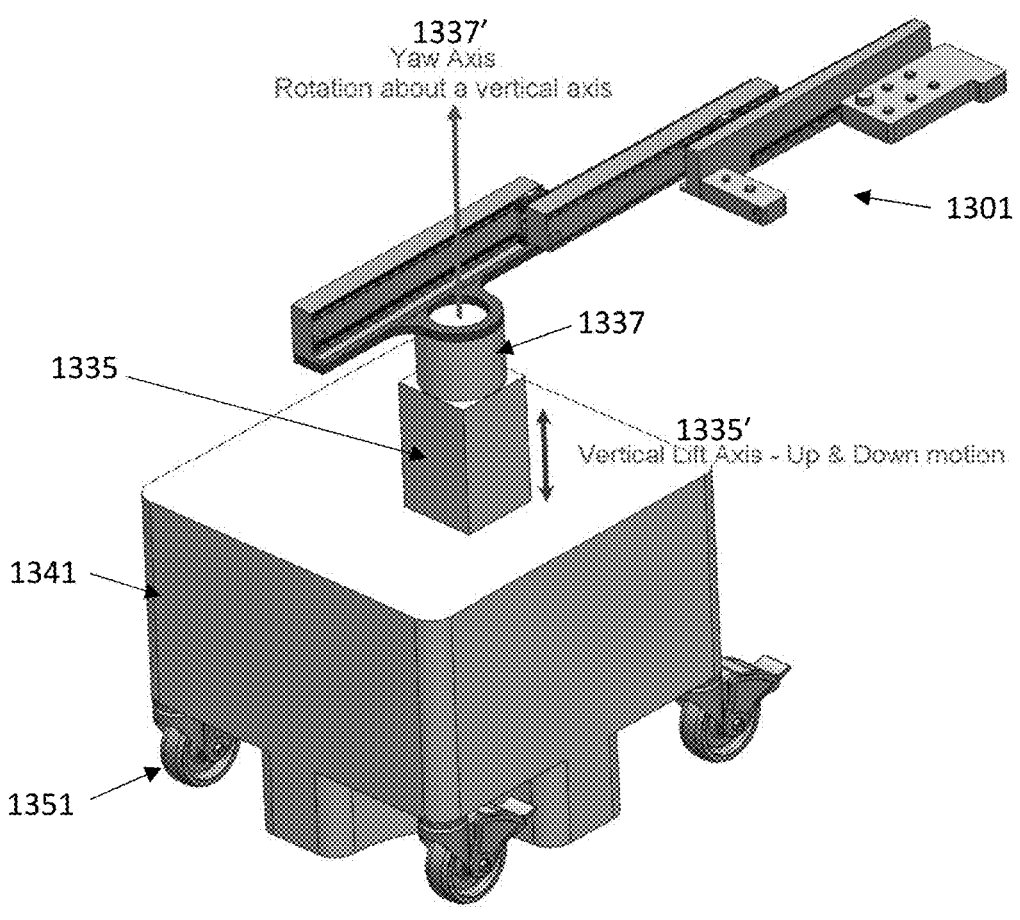
FIG. 13 illustrates vertical and yaw adjustment of a system for deploying a nested robotic device similar to that shown in FIGS. 3A-3B and 4.

As mentioned above, in general these apparatuses and methods be configured to allow adjustment and/or readjustment of the link assembly 1301 relative to the patient or bed. FIG. 13 illustrates different movement and adjustment axes for a device similar to that shown in FIGS. 3A-3B and 4, above. In FIG. 13, the system includes a base 1341, and wheels 1351, that support the arm (e.g., column, shaft, etc.) 1335 and may change the relative position of the linear link assembly to the base. For example the height of the link assembly may be adjusted in the vertical axis 1335', e.g., using a vertical lift 1335 as shown. Alternatively or additionally, the angle of the vertically-arranged link assembly relative to the bed or patient may be adjusted, e.g., by rotating the vertically-arranged link assembly about the yaw axis 1337'. The position of the link assembly may be adjusted prior to performing the procedure with the system. For example, the position the telescoping robot relative to the cart may be adjusted for ether yaw and/or vertical. These axes can be locked out intraoperatively. In some example, these axes can also be put into a floating state to enable intraoperative patient repositioning. In any of these apparatuses the cart wheels can be unlocked and/or locked, to allow planar positioning of the robot relative to the patient.

In general, one or more additional tools (actuators, drivers, etc.) may be included and/or mounted to the system, including to the link assembly 1401 (e.g., vertically oriented link assembly) to assist in manipulating multiple different end effectors that may be used with the endoscope, including inserting and or operating though a working channel of the endoscope. In some examples the endoscope may include an entry point in the Endoscope Handle for a tool that goes into an Internal Working Channel (IWC) of the endoscope. In one example a 9th robot axis that controls the insertion depth of this tool may be used. The use of such additional tools may create additional degrees of freedoms (DOFs) to control more axes of the tools in the IWC.

Figure 14:
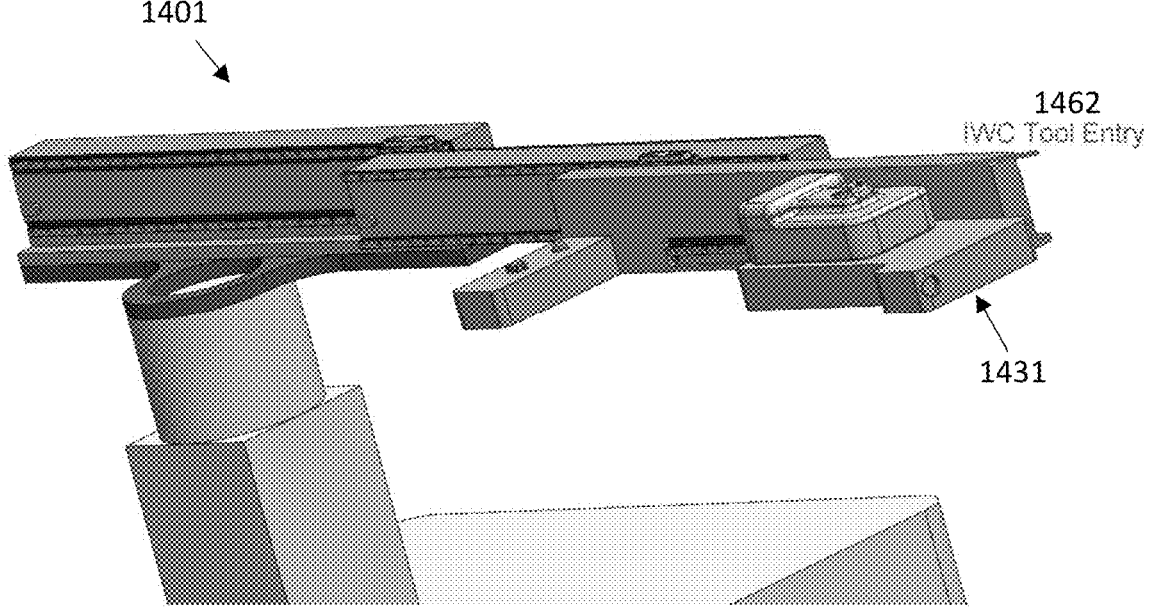
FIG. 14 shows an example of a tool manipulator (e.g., insertion tool) that may be used with any of the systems described herein.

For example, FIG. 14 shows a schematic of a generic internal working channel (IWC) tool 1462 for entry into a working channel. The device 1462 may be coupled to the mount assembly on the link assembly 1401, as shown and may engage with the mount assembly (on in some case the second mount region and/or first mount region) for operation.

Figure 15A:
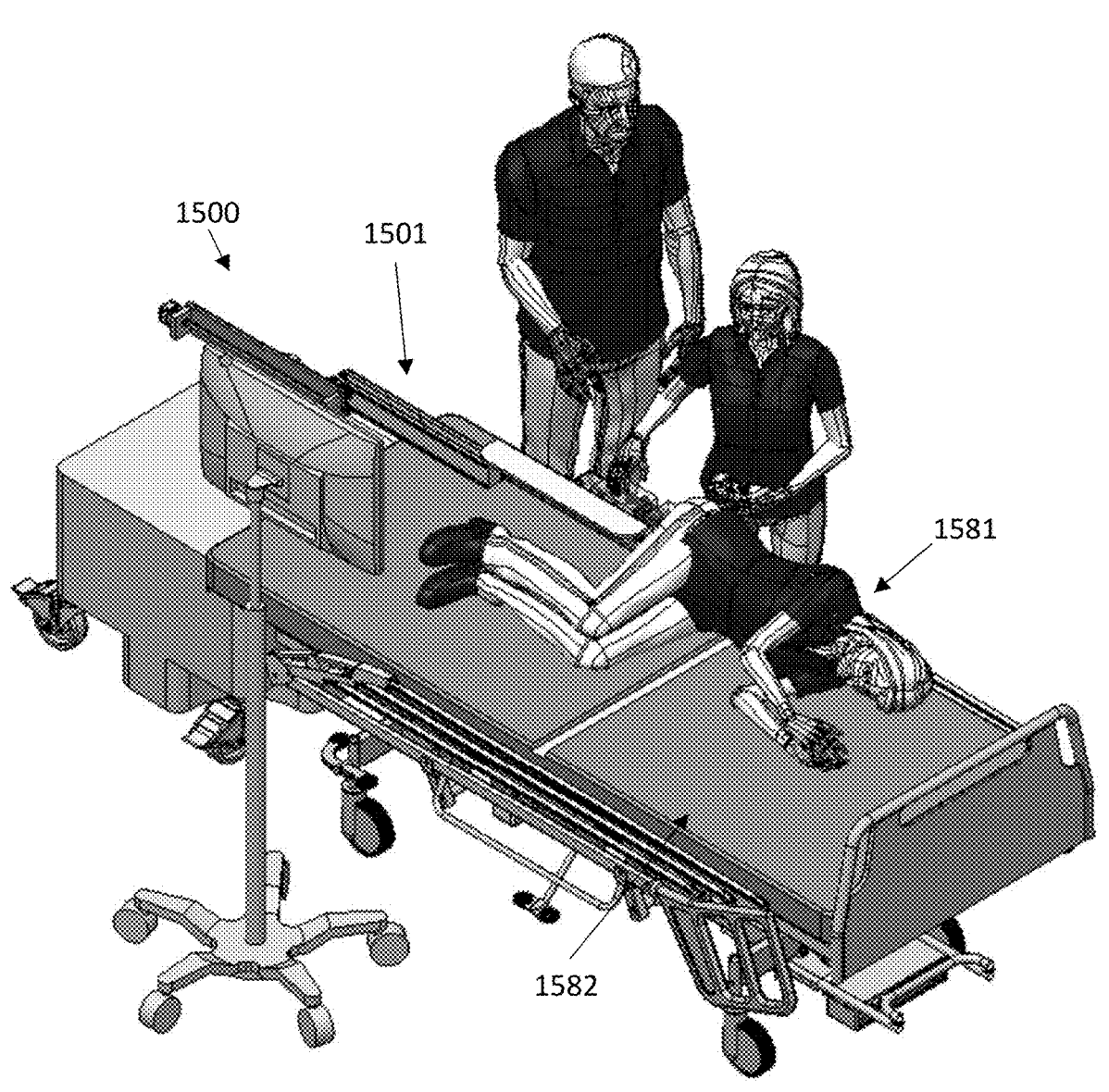
FIGS. 15A-C show an example of a system as described herein to perform a lower-GI procedure.
Figure 15B:
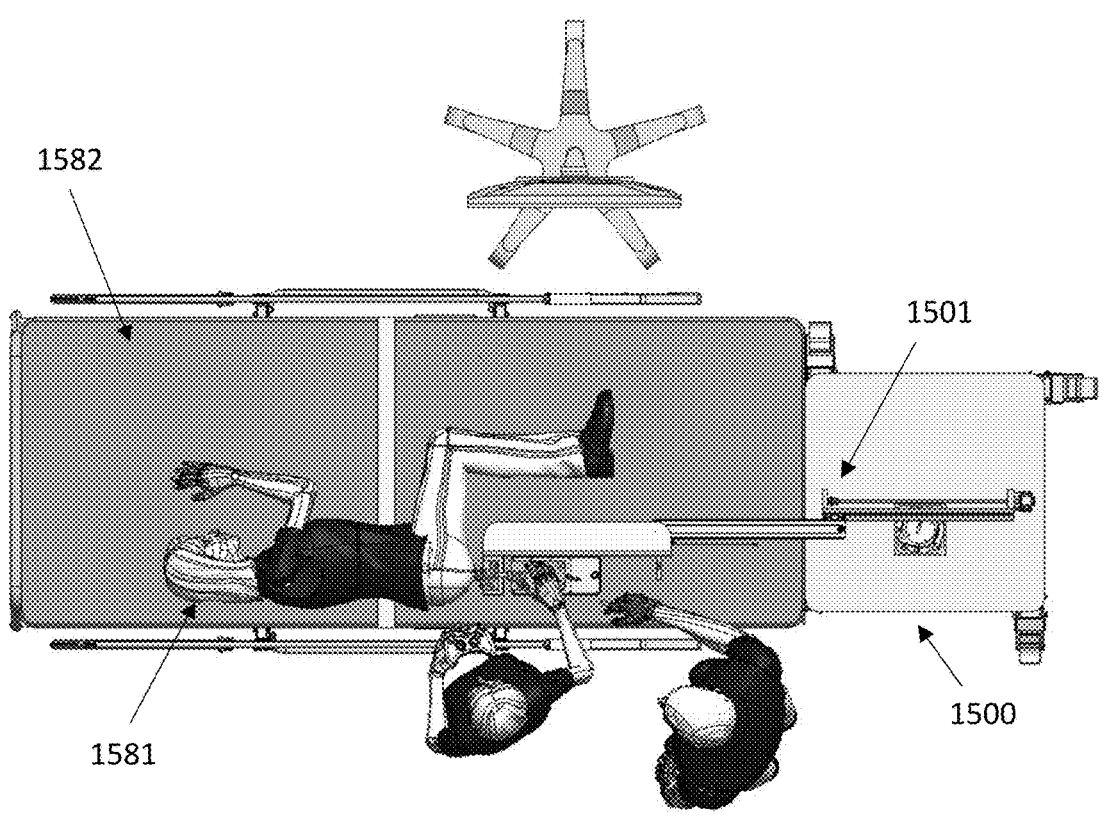
Figure 15C:
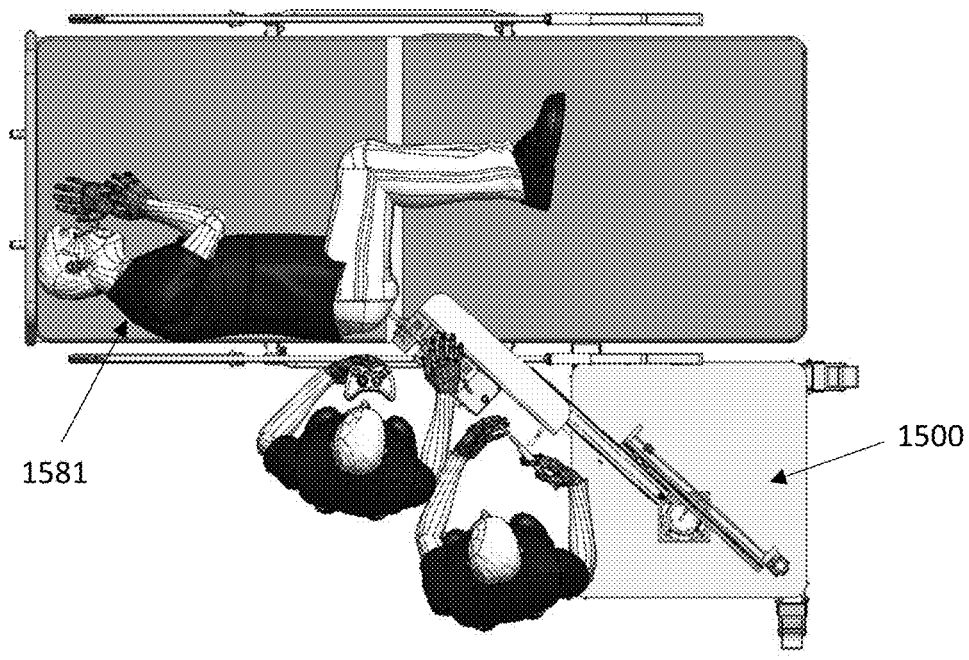

As mentioned, these apparatuses may be used with a variety of procedures. For example, these systems 1500 may be used as part of a lower GI procedure, as shown in FIGS. 15A-15C. In these examples, the system 1500 including a vertically arranged linear link assembly 1501 may be used with a patient 1581 virtually any orientation on the bed/cart 1582. The system may be positioned on the foot of the patient's bed. FIG. 15A shows the patient in a side-facing position. FIG. 15B shows a top view of a colonoscopy procedure as described above. The flexible tubular member is part of a system 1500 and is inserted and manipulated using a vertically arranged linear link assembly 1501. In FIG. 15C the patent 1581 remains approximately the same, and the angle of approach may be adjusted, as shown.

Figure 16A:
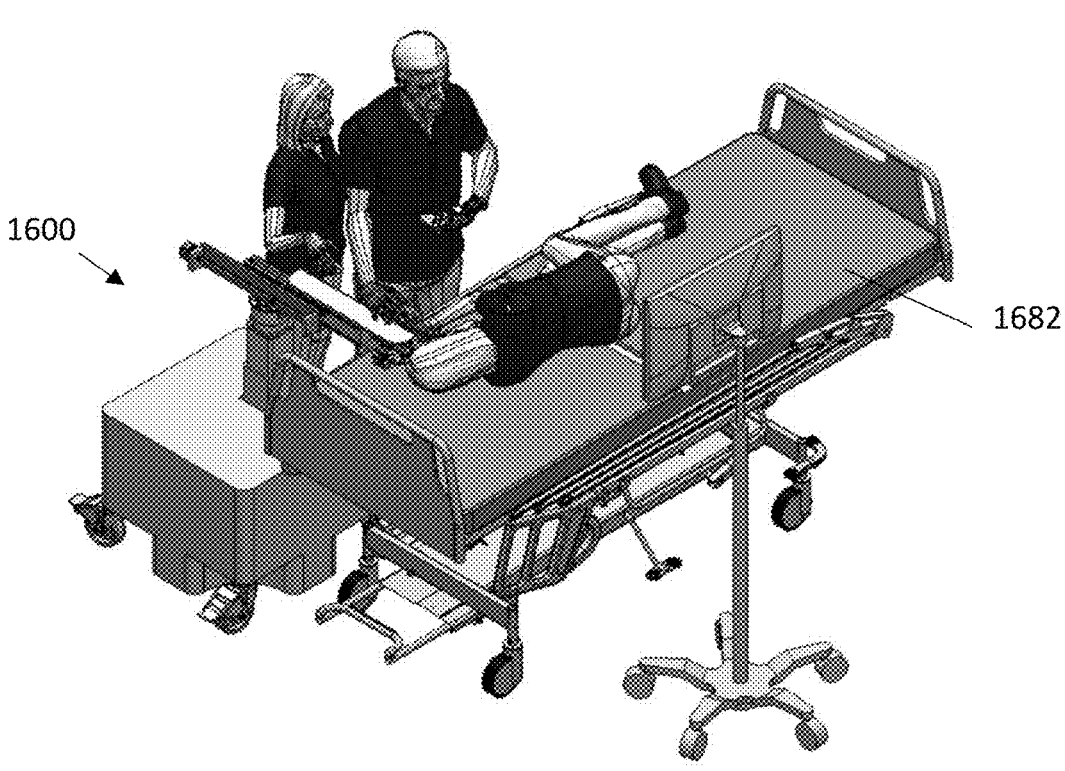
FIGS. 16A and 16B schematically illustrate an example of a robotically-enabled system as described herein.
Figure 16B:
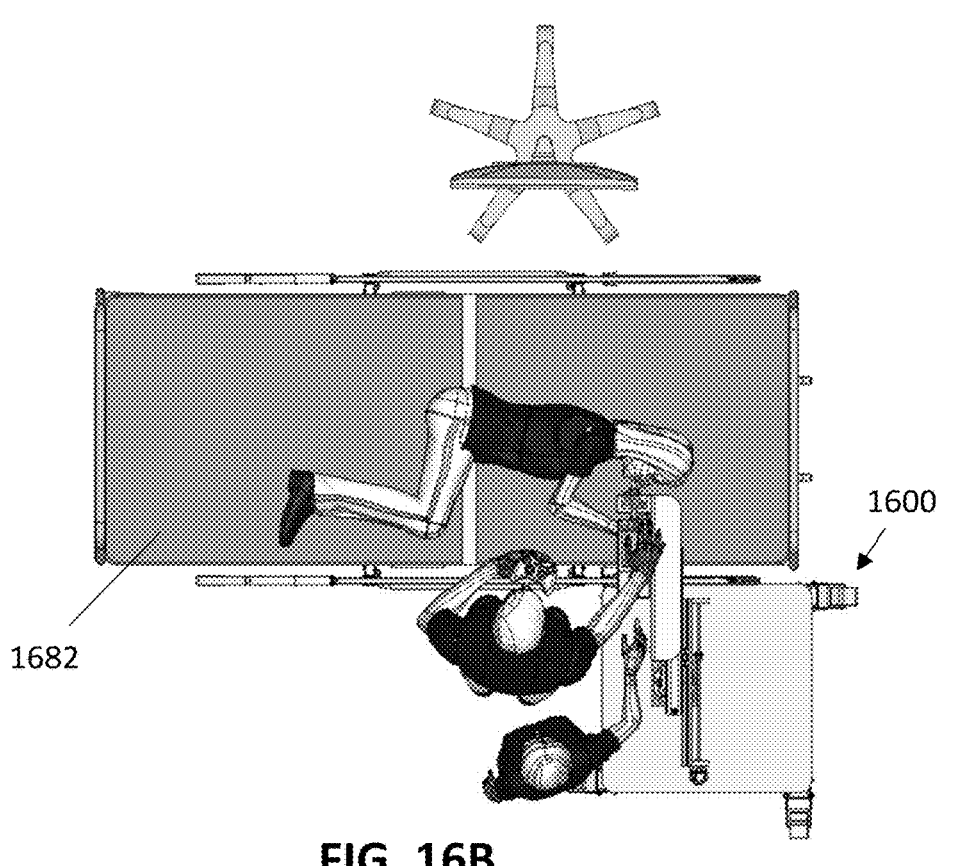

Any of these apparatuses may also or alternatively be used as part of an upper GI procedure, as shown in FIGS. 16A-16B. In this example the cart for the system 1600 is positioned at a side the bed 1682 so that the flexible tubular member held by the link assembly may be used to insert, manipulate and retract the flexible tubular member into the patient's body.

Anti-Buckling Supports

Any of the apparatuses described herein may include one or more supports to prevent collapse or other unintended movement of the flexible tubular member during dispensing/deploying (insertion and/or retraction), including in particular during deploying of a nested telescoping apparatus, which may include an overtube nested with an endoscope. In general, one or more supports ("supports," "endoscope supports" or "anti-buckling supports") may be coupled to the link assembly and may be configured to prevent buckling of the flexible tubular member at it extends distally from the link assembly. The flexible tubular member support may be a strut, beam, rod, pole, etc. that may support the length of the flexible tubular member as it extends distally and/or proximally away from the link assembly. In some examples the flexible tubular member support may include one or more loops or straps for holding (and supporting) a portion of the flexible tubular member.

The supports (e.g., the anti-buckling supports) are configured to support the nested apparatus (e.g., endoscope and overtube) during setup and throughout the procedure. This may be accomplished through the use of one or more (e.g., 2, 3, 4, 5, etc.) anti-buckling supports, that may be positioned off the distal side of the robotic assembly, and may be part of or coupled to the link assembly. In some cases, when the support(s) is/are not needed to support the nested apparatus, e.g., due to insertion depth, the supports may be configured to move away from the path of the scope and any moving portions of the robot, and/or the bed/table (e.g., gurney) or patient. For example, the supports may move away either under or 'behind' the robot cart. The one or more supports may then automatically return upon device retraction to provide support to the nested system. Supports may be part of the overall robotic apparatus and may be configured to be cleanable in the same manner as the rest of the apparatus.

In some cases a flexible tubular member support may include a beam or arm that is coupled to and extend from a link of the link assembly. The support may be deflectable so that it may be deflected out of the way when not needed, or in order to prevent interference with another link or portion of the system. Thus, the support may be coupled to the link in a movable joint, such as a hinge pivot, ball joint, etc. The movable joint may be biased so that it may return to a predetermined position after it has been deflected and the interfering portion of the system has moved out of the interfering region. For example the movable joint may be biased to assume a supporting position by a spring or other bias.

The portion of the support configure to hold the flexible tubular member may be referred to herein as a seat or seating region. The seat may be configured as a loop, ring, etc., though which the flexible tubular member may be passed. Alternatively the seat may be open, e.g., on a top region, so that the flexible tubular member may be inserted and removed along its length. In some examples the seat may be opened/closed to insert/remove the flexible tubular member. The seat may be configured to allow the flexible tubular member to slide or move therein. For example, the seat may include a lubricious (e.g., slippery) surface to allow sliding of the flexible tubular member relative to the seat. In some example the seat may include a rolling or moving surface (e.g., roller, wheel, ball bearing, etc.) to allow movement of the flexible tubular member relative to the seat.

Figures 17A, 17B:
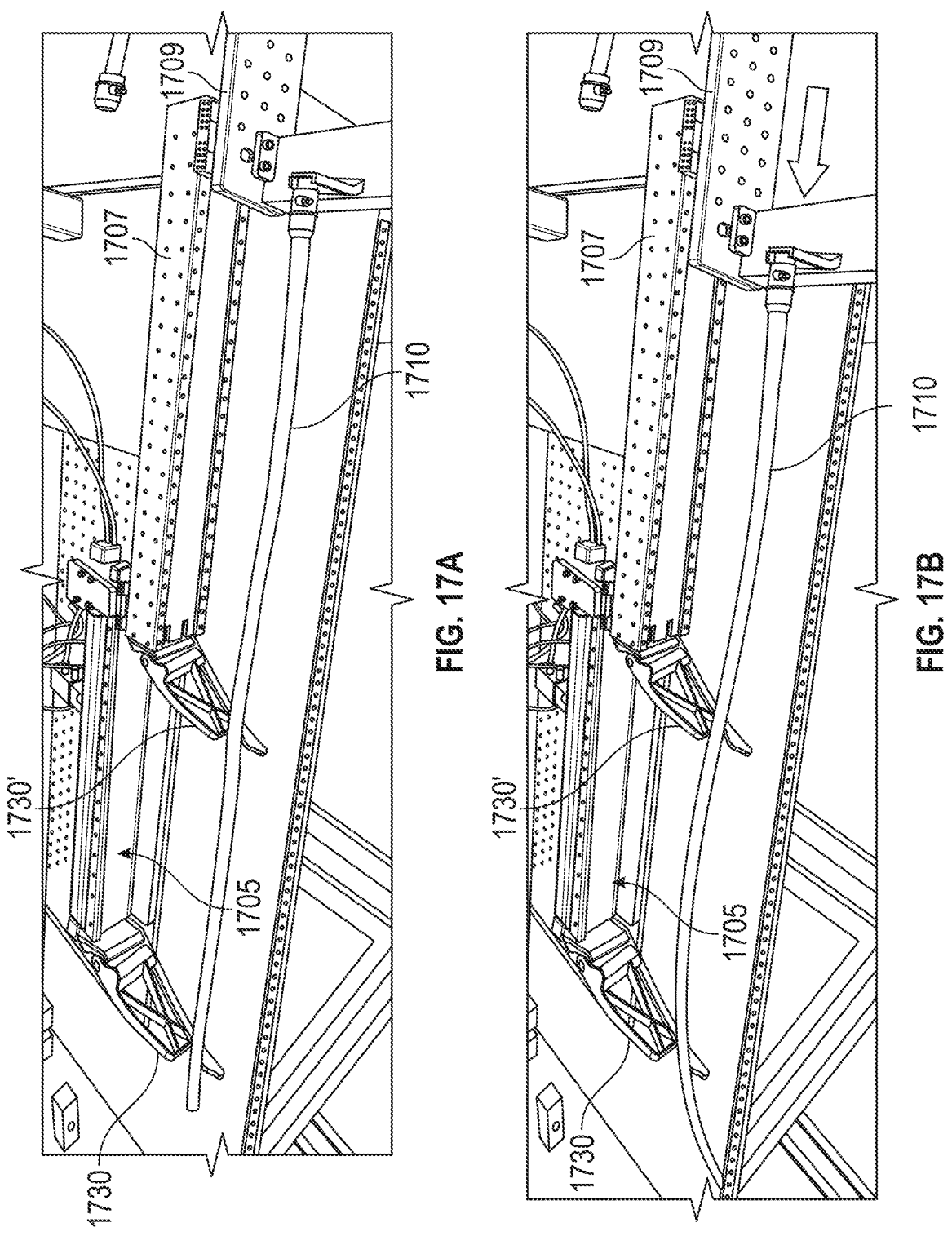
FIGS. 17A-17H illustrate the operation of a flexible tubular member support when extending and retracting a set of linear links of a system as described herein.
Figures 17C, 17D:
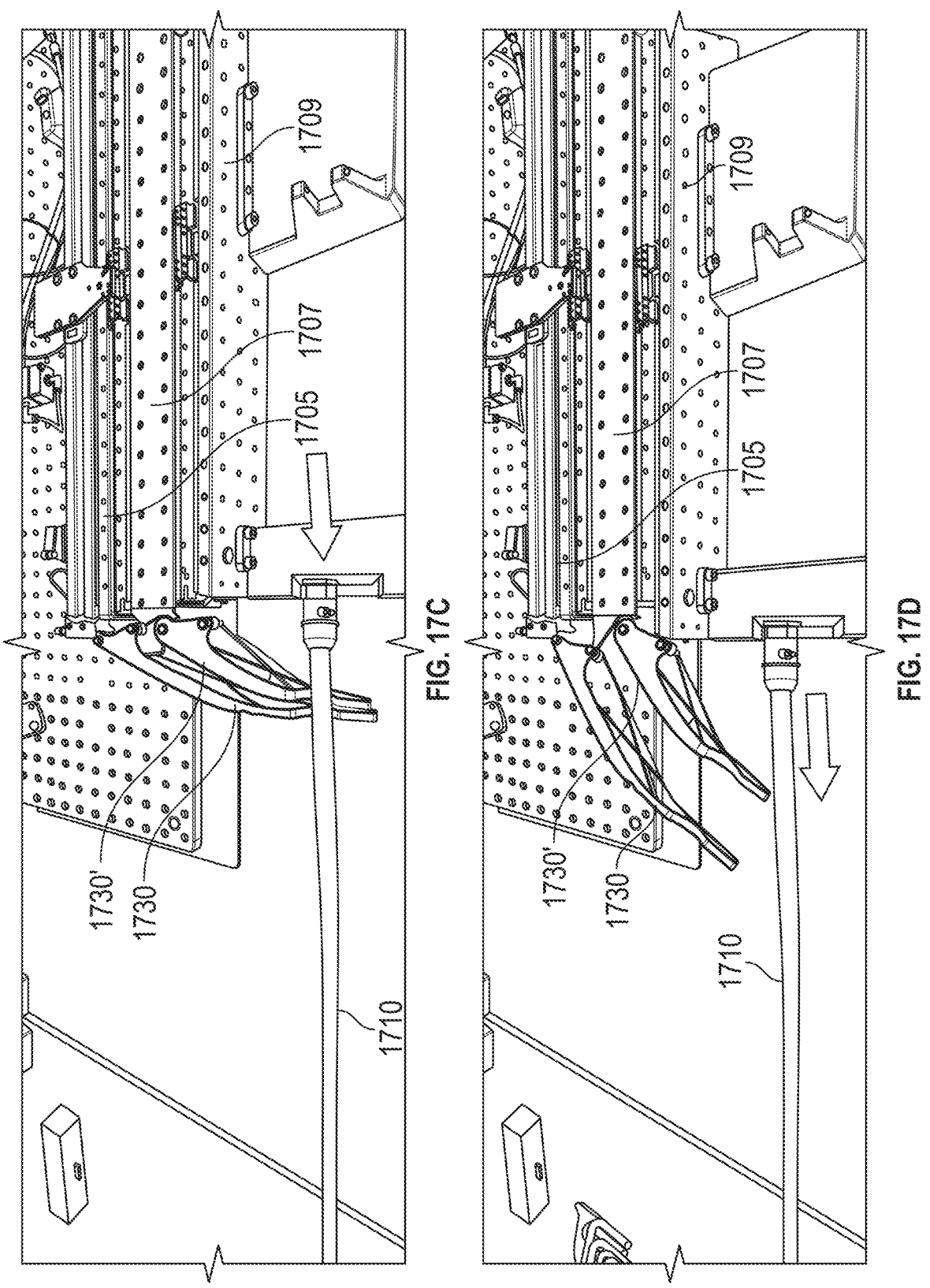

FIGS. 17A-17H illustrate operation of one example of a pair of supports coupled to a link assembly. In this example the first support 1730 is coupled to a distal end region the first link 1705. The second support 1730' is coupled to a distal end region of the second link (e.g. intermediate link). The third link 1709 includes the mount assembly to which the flexible tubular member is attached. In this example, for simplicity in demonstrating the operation of the supports, the flexible tubular member includes just an outer overtube 1710. As shown in FIG. 17A when the link assembly is fully retracted proximally, the first 1730 and second 1730' supports extend outwards (perpendicular to the anterior/posterior axis) to provide support for the flexible tubular member 1710 that is held in the seats of each support. In FIG. 17B the third stage, to which the mount assembly holding the proximal end of the flexible tubular member is connected, is advanced distally, e.g., to insert the flexible tubular member into the body. As it is advanced, the flexible tubular member may slide relative to the supports. In this example, once the links are in approximately the neutral position, as shown in FIGS. 17C and 17D, the supports 1730,1730' may pivot out of the way of the adjacent links, and no longer engage with the flexible tubular member. As the flexible tubular member is closer to the patient insertion site, they may no longer be necessary. Alternatively, in some examples the supports may extend proximally and/or over (or in some cases under) the links to avoid interference and may continue to support the flexible tubular member in more distal configurations.

Figures 17E, 17F:
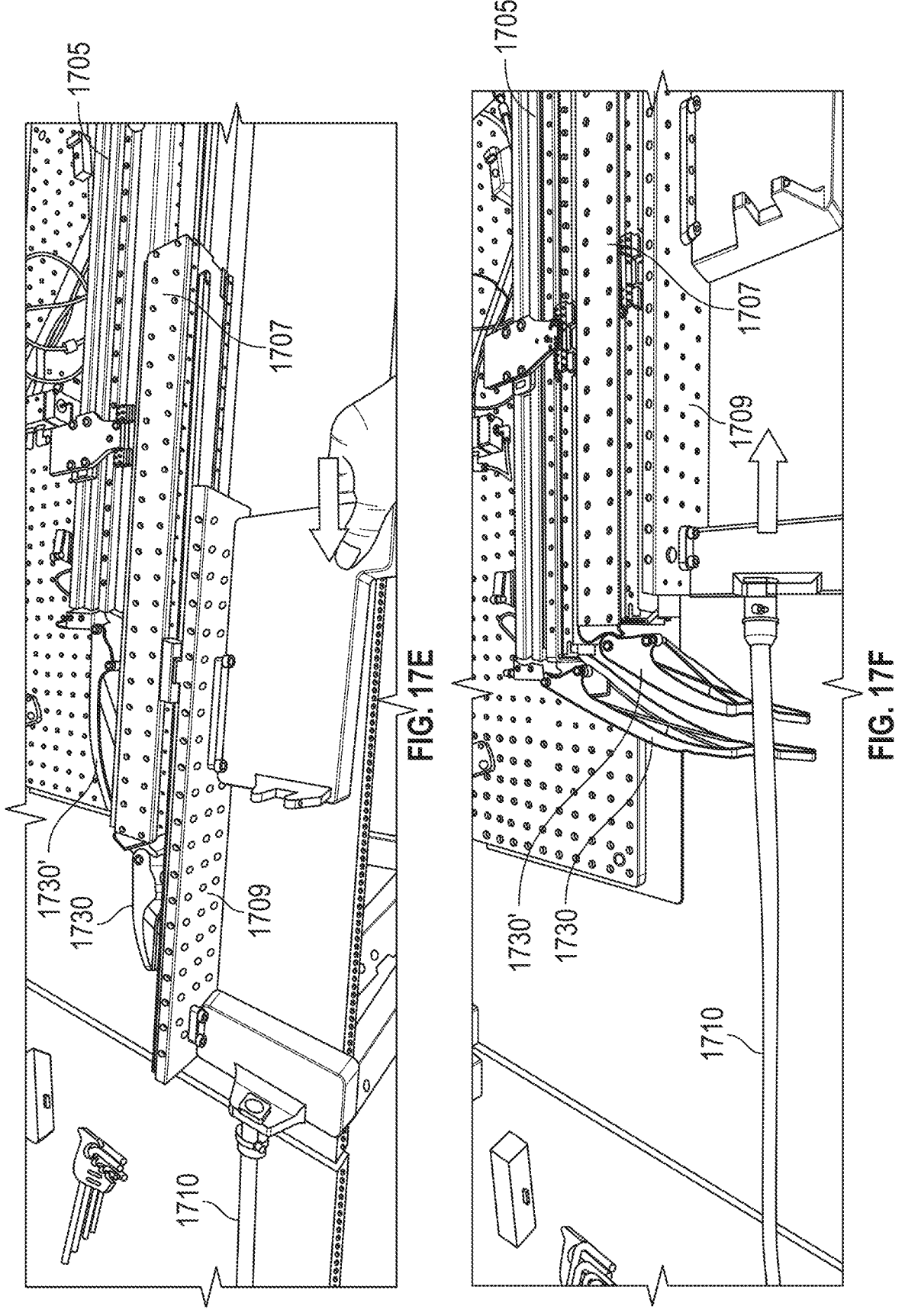
Figures 17G, 17H:
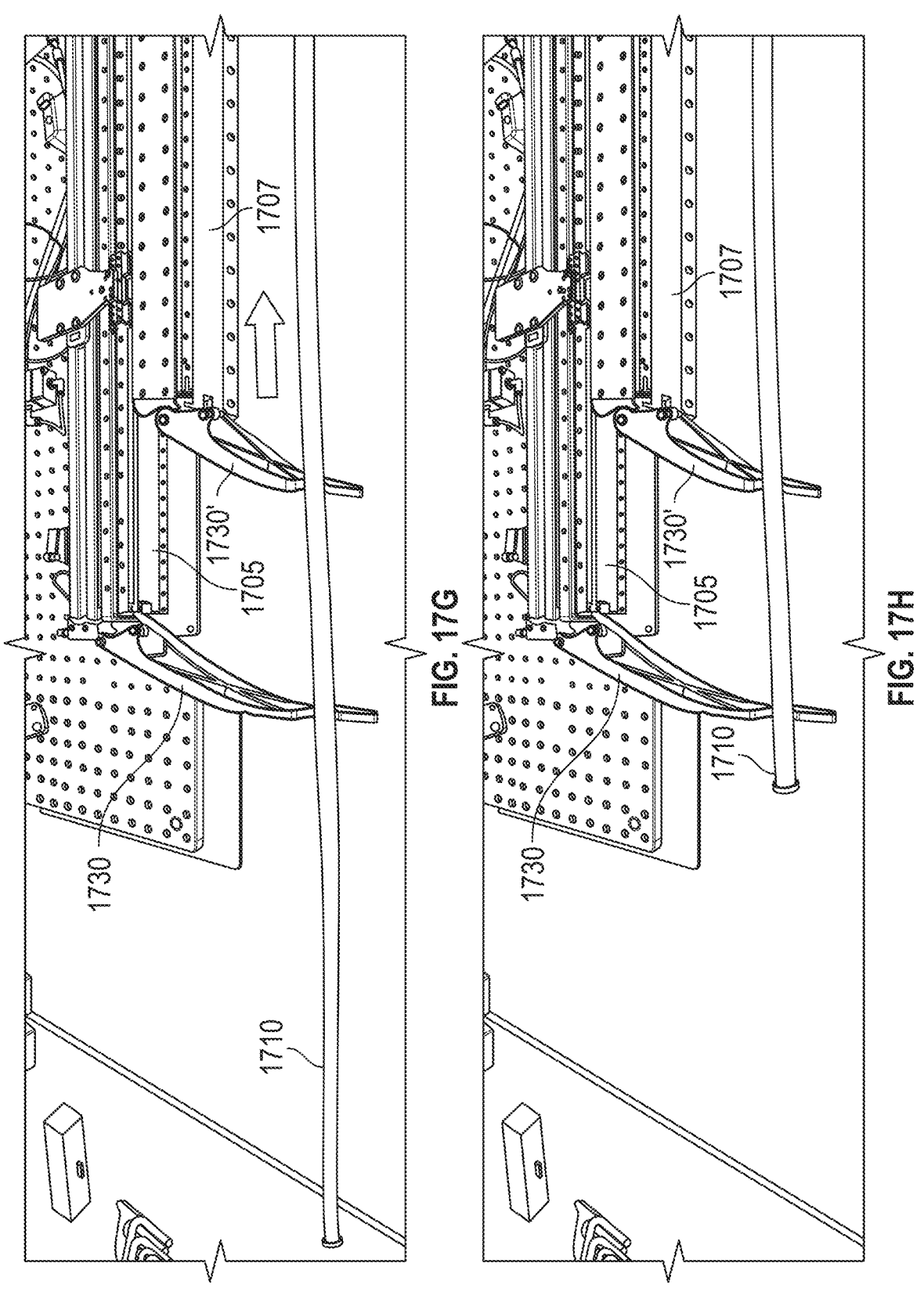

FIG. 17E shows the link assembly distally extended, with the seats displaced out of the way of the distally-advanced links. FIGS. 17F-17H illustrate the link assembly moving proximally, so that, as shown in FIG. 17F, the supports may be biased to return back to the extended positions to support the flexible tubular member. In this example the supports may be biased, by a spring, back to a position in which they underly the flexible tubular member as the link assembly is moved proximally, e.g., to retract.

As mentioned, in some examples the support(s) may extend distally from a link in order to support the flexible tubular member even when the links, including supporting the links when the link assembly is in the neutral (centered) configuration and/or extended distally (e.g., inserted into the patient). For example, the support may include a distally-extending arm segment that may be a fixed length or may be telescoping as the link assembly telescopes.

In general, any of the apparatuses described herein may include one or more supports that are configured to support the telescoping apparatus (e.g., the overtube portion of the apparatus) outside of the patient's body. These supports may be configured to move out of the way of the link assembly as it drives the telescoping apparatus proximally and distally, as just described. In some cases these supports may be configured to be moved in such a manner that they do not interfere with the bed or table on which the patient is positioned. Any of these supports may be configured to be moved to a stored position having a minimal footprint, particularly in the plane of motion of the link assembly. The supports may be configured to have a pre-deployment configuration, in which one or more of the supports may be moved away from the plane of motion of the link assembly, a deployed configuration, in which the supports may be positioned and may be held in the plane of movement to support a portion of the telescoping apparatus outside the patient body, and a post-deployment configuration, in which the one or more supports is moved out of the way of the links as they are moved towards the patient to avoid interference with the operation of the telescoping apparatus.

Any appropriate number of supports may be included. In some cases the supports may be coupled to the links and/or the shuttles. The number of supports may be based on the length of the endoscope to be extended. The supports may be arranged so that they provide a minimum support between every 0.15 m and 0.7 m (e.g., between about 0.2 m and 0.5 m, between about 0.25 m and 0.5 m, etc.). This separation distance between the supports may be adjusted based on the properties of the telescoping apparatus (e.g., based on its size, flexibility, etc., and therefore how much support it may need). The distance between the supports may change with operation of the apparatus, e.g., as the telescoping apparatus is inserted/removed.

Figures 18A, 18B:
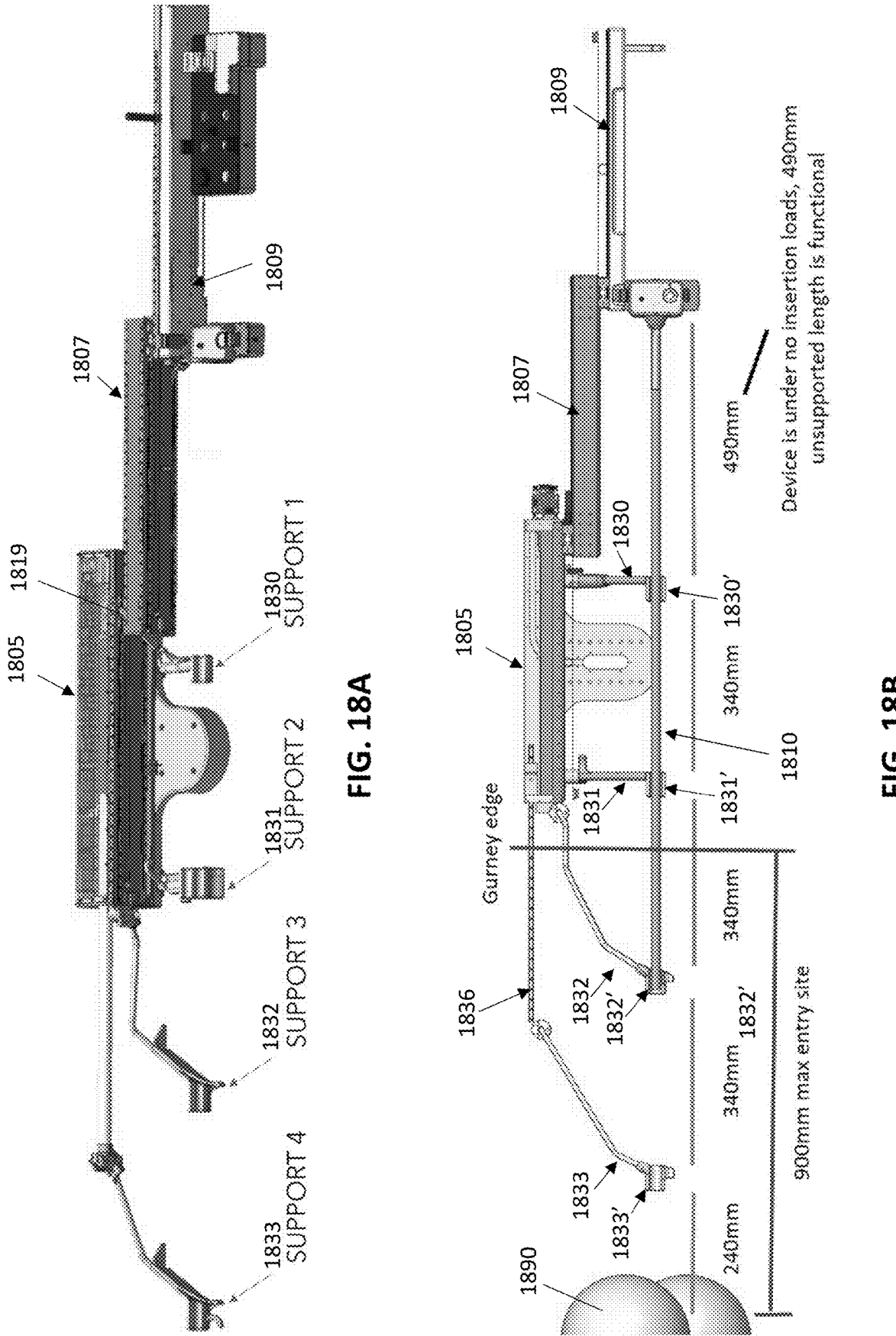
FIGS. 18A and 18B schematically illustrate an example of a link assembly including a plurality of supports configured to support a nested telescoping assembly (e.g., a rigidizing overtube/endoscope).

FIG. 18A shows one example of an apparatus including a plurality of supports that may deploy during movement of the links to support a telescoping apparatus (not shown). In FIG. 18A the apparatus includes four supports 1830, 1831, 1832, 1833 that are shown in the deployed configuration. The first support (support 1 1830) is coupled to the shuttle 1819 between the first link 1805 and the second link 1807. This support may be deployed when the second 1807 and third 1809 links are extended proximally, as shown in FIG. 18A. In the deployed configuration the seating region of the first link is in-line with the direction of insertion and/or movement of the link assembly. Otherwise, the support, which include an arm coupled to a seating region, may be rotated down and out of the plane of movement of the links. A bias mechanism, e.g., spring, elastic, etc., may drive the support up and into the plane of movement once the second and third links are extended proximally. In some cases the first support may be coupled to the shuttle by a pivoting joint that is biased, and one or more cam surfaces may be used to drive the support out of the plane of movement (e.g., so that it rotates down and away from links and mounts holding the telescoping apparatus). Thus, the first support 1830 includes a pre-deployed configuration in which the arm region rotates the seating region down and away from the link assembly and mount(s). As mentioned, the first support may be driven by a bias the drives the seating region into the plane of movement when the link assembly is fully (or in some cases partially) retracted proximally, e.g., from the pre-deployed configuration to the deployed configuration.

The second support 1831 in FIG. 18A is coupled to the second link 1807 on an underside region of a distal end of the second link. This second support also includes an arm region or portion coupled to a seating region. The second support may be coupled to the second link at a first end; the seating region may be at and/or may extend from the second end of the arm region. The arm region of the second support 1831 extends laterally from the second link to position the seating region in the plane of movement (and in-line with the direction of insertion/movement of the link assembly). In FIG. 18A, the second support 1831 is also pivotally connected to the link assembly, e.g., to the second link 1807, so that it has a first (e.g., pre-deployed) configuration in which it is rotated down and out of the plane of movement of the link assembly, and a second (e.g., deployed) configuration, in which the second support is rotated up so that the seating region is in the plane of movement of the link assembly, as shown in FIG. 18A. In some cases the apparatus may include a bias tending to drive the second support from the pre-deployed configuration to the deployed configuration. The bias may be a spring and/or elastomeric material.

In FIG. 18A the third support 1832 also includes an arm region that is coupled to the second end of the third arm. The arm of the third support includes an elongate length and is configured to extend some distance (e.g., between about 0.1 and 0.5 m, 0.2 and 4 m, etc.) from the proximal end of the first link 1805. The third support may be movably coupled to the first link 1808 of the link assembly so that that it may be moved out into and out of the plane of movement of the link assembly. In FIG. 18A the third support is shown with the seating region of the third support 1832 in the plane of movement of the link assembly and in-line with the other supports' seating regions so that these seating regions may all support the telescoping apparatus in a line extending from the mounts as the telescoping device is inserted or retracted. The elongate length (e.g., elongate body) of the support may have curved or bent shape. For example in FIG. 18A, the elongate length of the third support 1832 has a bend so that in the post-deployed configuration it is moved both slightly downward (e.g., between 3 and 20 cm, e.g., between 3-12 cm, between 3-10 cm, less than 10 cm, etc.) and laterally clockwise away from the plane of movement of the link assembly, so that it does not interfere with either the link assembly or the bed/table (e.g., gurney) on which the patient is positioned. The attachment between the elongate body of the third support and the first link of the link assembly may be configured with one or more cam surfaces that direct the movement of the support between the deployed and post-deployed configuration. In some cases a bias may be arranged to drive the third support into the deployed configuration (or from the deployed configuration into the post-deployed configuration). The third support may also have a pre-deployment configuration in which the arm of the third support is moved up and out of the plane of movement of the link assembly, as will be described in greater detail below.

FIG. 18A also includes a fourth support 1833 that also extends from the first link. In some cases, the fourth support may extend from the first link on an extendable arm 1836 that can be extended distally or withdrawn proximally from the first link. The extendable arm may be extended and/or retracted manually or automatically. A distal end of the extendable arm may couple to the first end of the fourth support 1833, and may include a pivoting or bending joint similar to that used for the third support. The fourth support also includes a bent or curved arm region and a seating region on the second end of the arm (e.g., arm region). In FIG. 18A the fourth support arm is bent so that the seating region is in line with the seating regions of the first, second, and third supports when they are in the deployed region. The fourth support art is also configured so that as the link assembly advances the second and/or third link distally the fourth support may also be deflected down and laterally. For example, the fourth support may be deflected slightly downward (e.g., between 3 and 20 cm, e.g., between 3-12 cm, between 3-10 cm, less than 10 cm, etc.) and laterally clockwise away from the plane of movement of the link assembly, so that it does not interfere with either the link assembly or the bed/table (e.g., gurney) on which the patient is positioned. The downward deflection may be limited so as not to collide with the bed/table surface (e.g. gurney). The fourth support may also be configured to have a pre-deployment configuration in which the arm of the fourth support is moved up (e.g., vertically or approximately vertically) and out of the plane of movement of the link assembly, as will be described in greater detail below.

Thus, as described above, in general the apparatus may include one or more supports that are movably coupled to the link assembly, so that the support(s) may be moved in—or out—of the plane of movement of the link assembly based the position of the link assembly. Each support may be operably coupled to the link assembly (e.g., a link or shuttle) so that they may be moved into and out of position depending on the configuration of the link assembly.

FIG. 18B shows another example of a link assembly including a plurality of supports similar to those shown in FIG. 18A. FIG. 18B also shows examples of spacing dimensions between support, for illustration only. These dimensions are not intended to be limiting and may be different based on the configuration of the link assembly and/or the telescoping apparatus, as mentioned above. A portion of a telescoping apparatus 1810 is shown in FIG. 18B; in practice the telescoping apparatus may extend all the way to and into the body 1890 (e.g., the anus).

In general the supports shown in FIGS. 17A-17H and FIGS. 18A-18B may include an arm region or portion coupled to a seating region. In FIG. 18B the supports 1830, 1831, 1832, 1833 may each include an elongate and rigid the arm region that is coupled at a second end to a seating region 1830', 1831', 1832', 1833'. The seating region may be flat or may include sides that may retain the telescoping apparatus (e.g., overtube and endoscope), as shown in FIG. 18B. For example, the seating region may form a channel (e.g., an open channel) having sidewalls. In any of these apparatuses the seating region may be configured to allow the telescoping apparatus to slide relative to the seating region. In some cases the channel may be lubricious and/or may include one or more moving surfaces (e.g., rollers, bearings, treads, etc.).

As mentioned, the seating region may be configured to accommodate sliding as the telescoping apparatus (e.g., overtube) is driven distally and/or proximally by the link assembly (including by the mounts). Thus, as used herein 'seating' refers to the ability to retain the telescoping assembly in a dynamic (e.g., sliding) manner.

The seating region may alternatively be referred to herein as a channel. In general, the seating region may be configured to support the telescoping apparatus even under lateral forces, so that the seating region may prevent the telescoping apparatus from falling out of the seating region. As mentioned, in some cases the seating region includes sidewall regions. In some cases the seating region may include a cover or retainer that wraps at least partially over the telescoping apparatus while still allowing it to slide in/out (distal/proximal) and vice versa. Thus in some examples the sealing region may be configured to include sides that extend approximately 140 degrees or more (e.g., 150, 160, 170, 180, etc.) around the sides of a telescoping apparatus when seated therein. In some cases, the seating region sidewall has a height that is between 0.4× and 3× the radius of the telescoping apparatus, such as between about 0.5× and 2×, between about 0.6× and 1.5×, etc. The inner surface (e.g., seating surface) of the seating region may be cylindrical, e.g., in some cases having an inner radius that is greater than the outer radius of the telescoping apparatus (e.g., between 1.1× and 3×, between 1.1× and 2×, etc.). In some cases the seating region may have a length that is between 1 mm and 10 cm, e.g., between 0.5 cm and 5 cm, between 0.5 cm and 4 cm, etc.

Figure 19A:
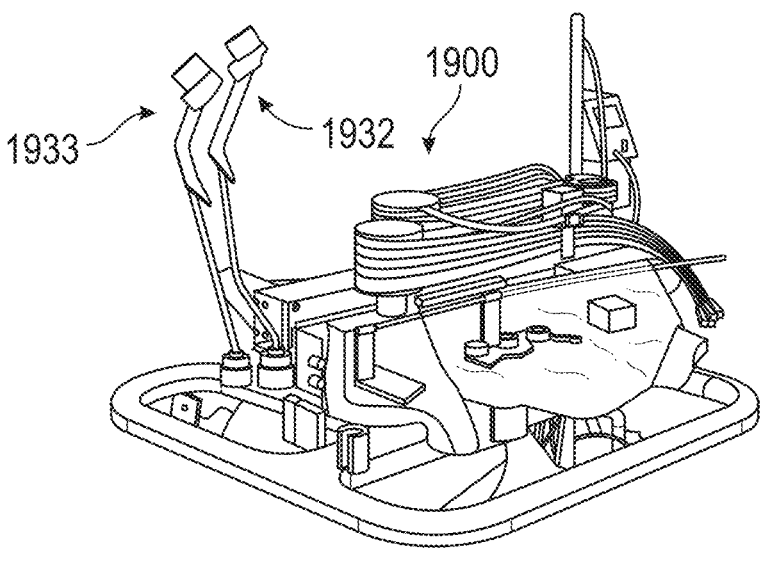
FIGS. 19A-19H illustrate one example of the preparation of an apparatus including a link assembly and supports (e.g., flexible tubular member supports) for use with a nested telescoping apparatus (e.g., a flexible tubular member).

FIGS. 19A-19H illustrate one example of an apparatus including supports being prepared for use with a telescoping apparatus. In FIG. 19A, the apparatus 1900 is shown in an initial, e.g., stored configuration, prior to deployment and prior to attaching the telescoping apparatus. The apparatus includes a link assembly, to which a plurality of fluid lines have been attached, as well as four supports, similar to the examples shown in FIGS. 18A-18B. In FIG. 19A the third 1932 and fourth 1933 supports are shown in a pre-deployment configuration, in which they are arranged vertically up and out of the plane of movement of the link assembly, providing a more compact configuration. In addition, the link assembly is shown in the un-extended configuration in which the inner and intermediate links are aligned with the outer link. In some cases the apparatus may include a release catch to release and lower the fourth and/or third support, which may pull past a spring detent to lower arm.

Figure 19B:
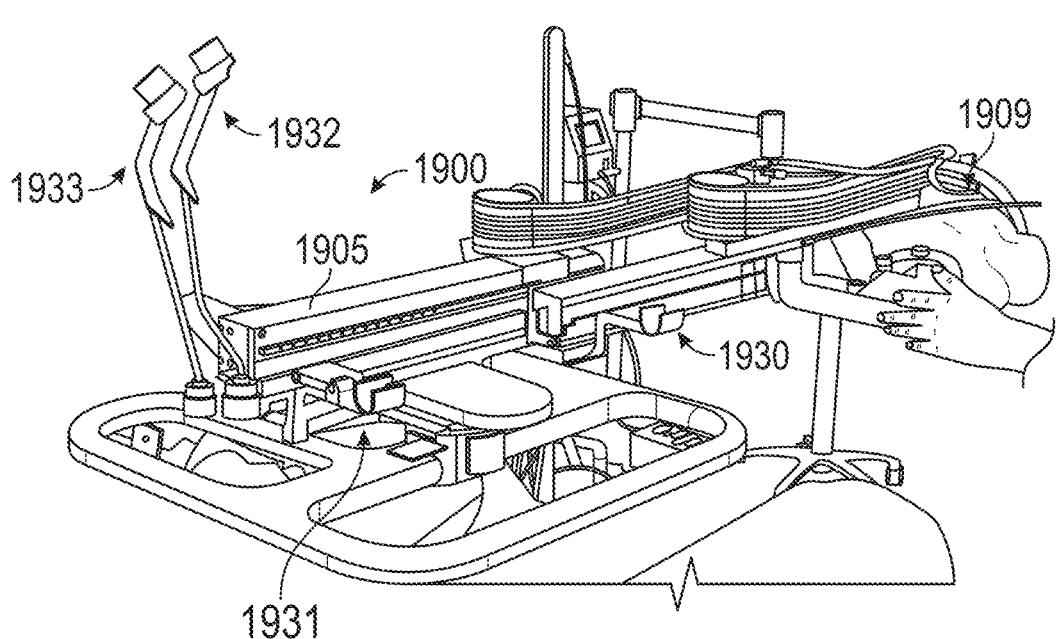
Figures 19C, 19D:
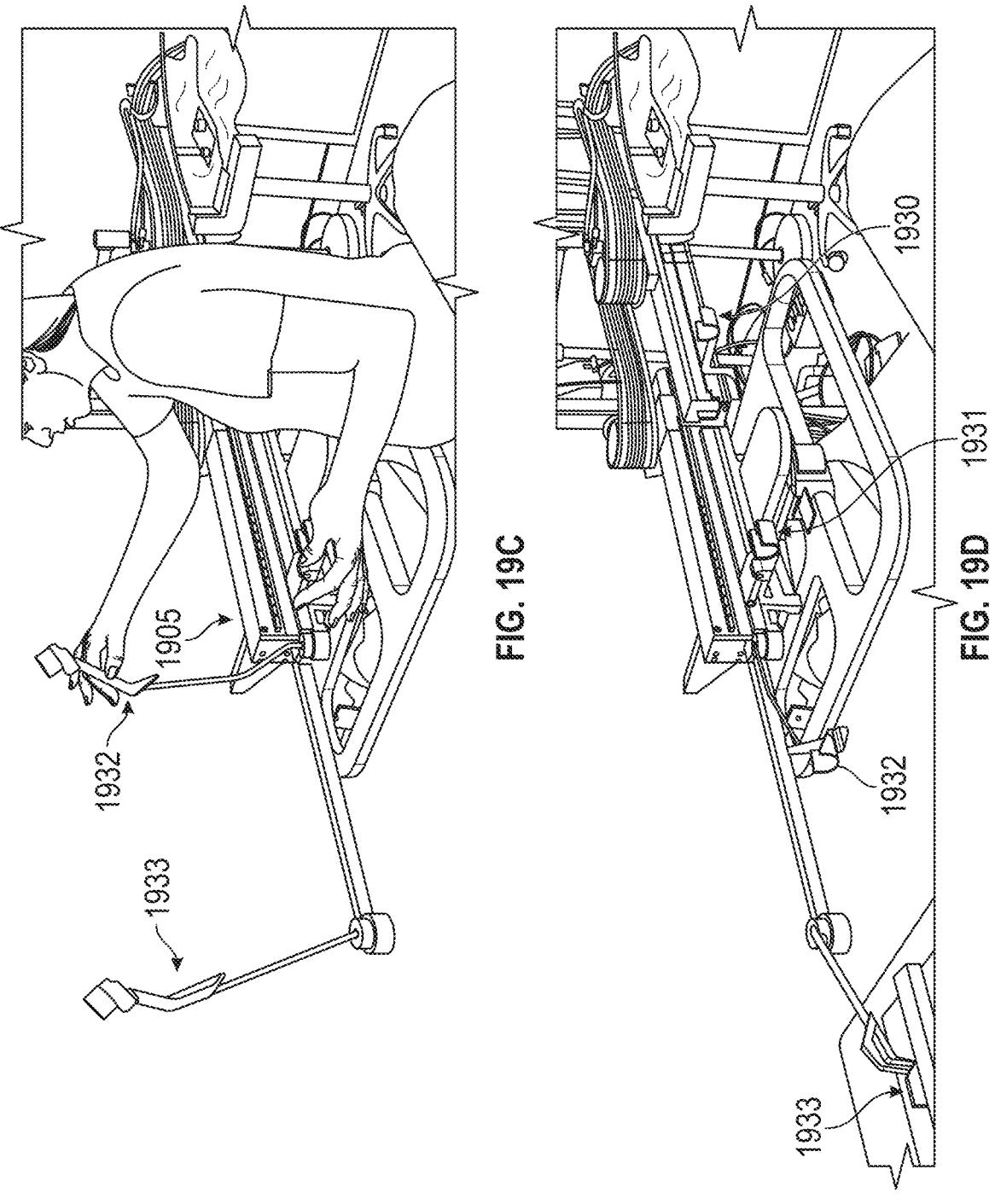
Figures 19E, 19F:
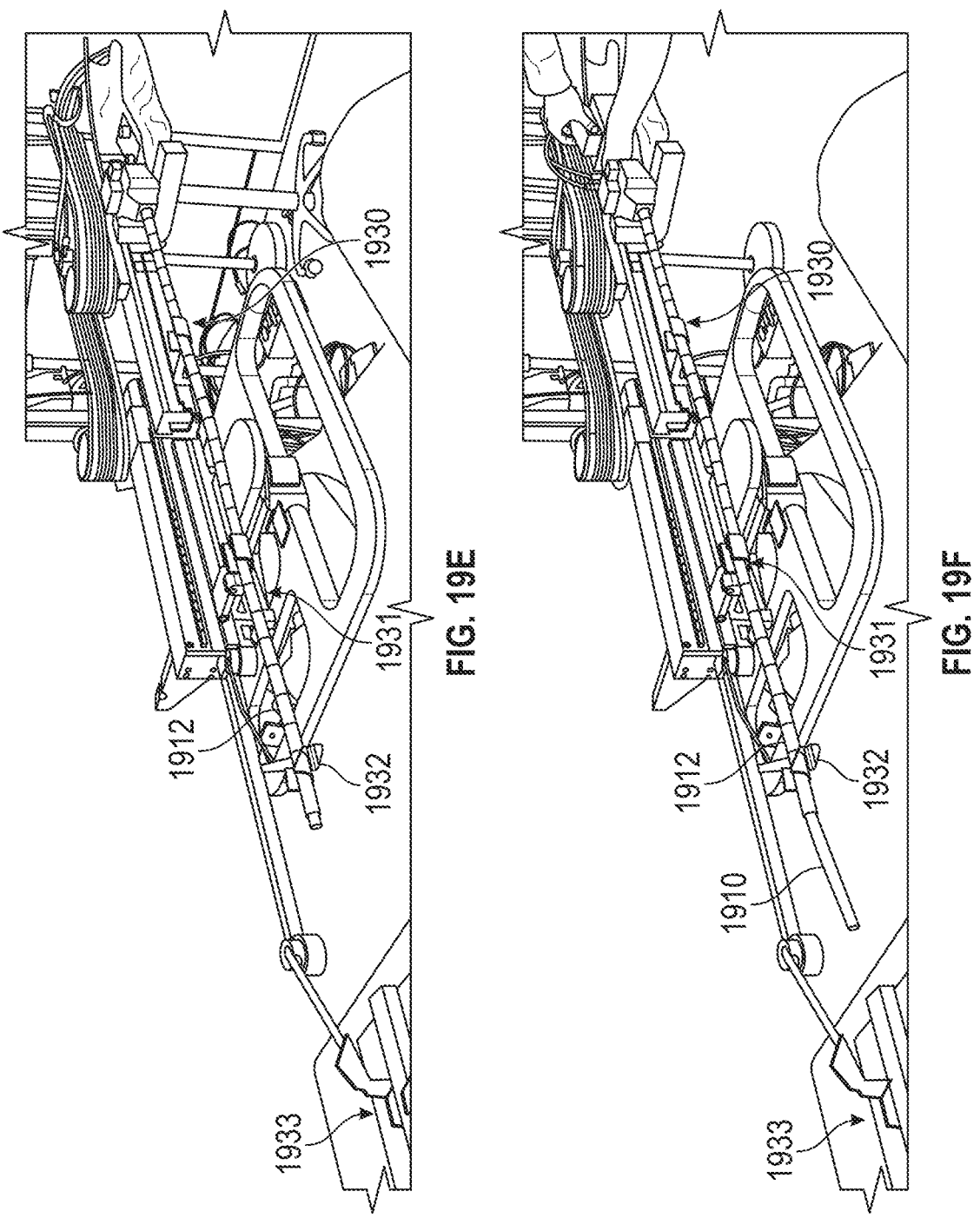
Figure 19G:
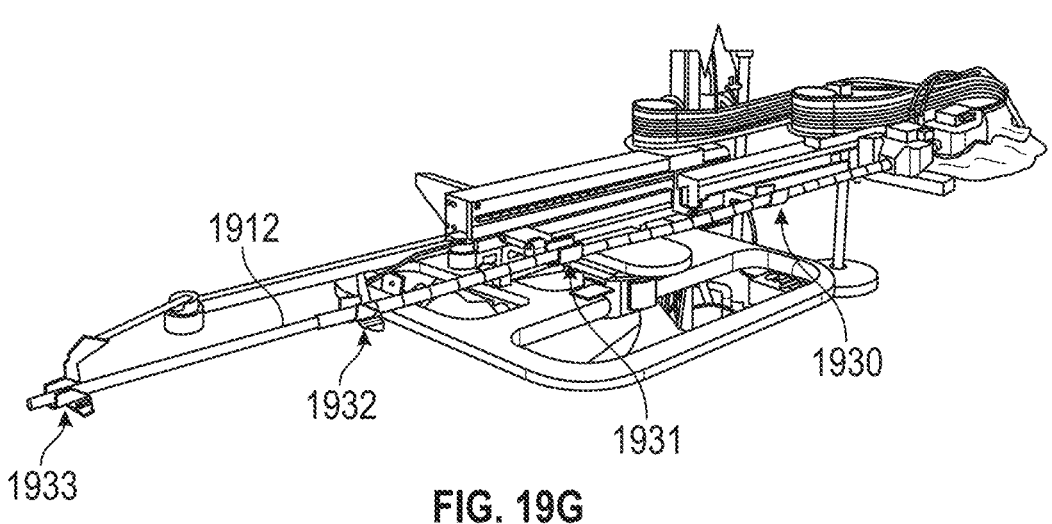

The apparatus may be prepared for deployment by attaching the telescoping apparatus (e.g., overtube and endoscope). For example, as shown in FIG. 19B, the link assembly may be retracted proximally, either manually or automatically, by extending the inner link 1909 in a proximal direction, as shown. The fourth support 1933 may then be extended from the out link 1905, as shown in FIG. 19C. Both the third support 1932 and the fourth support may then be moved down (e.g., unfolded) so that the seating regions of the supports are in-line with the seating regions of the first 1930 and second 1931 supports. This is illustrated in FIGS. 19C and 19D. The telescoping apparatus (e.g., overtube and endoscope) may then be attached, as shown in FIGS. 19E-19F. In FIG. 19E the telescoping apparatus is attached with the overtube coupled at the proximal end to the overtube mount and the elongate, rigidizing, body 1912 of the overtube supported within the seating regions of the supports 1930, 1931, 1932, 1933. In FIG. 19F the inner member of the telescoping assembly, e.g., an endoscope or an endoscope covered in a sheath (e.g., a rigidizing sheath), is inserted into the body, by inserting the inner member 1910 through the lumen of the overtube from the proximal end and out of the distal end of the overtube. The proximal end of the inner member may be coupled to the mount (e.g., inner endoscope mount). In this example the inner member may initially be supported by the fourth support after loading, as shown as shown in FIG. 19G. In FIG. 19G the entire assembly is shown loaded and ready for deployment.

Figure 19H:
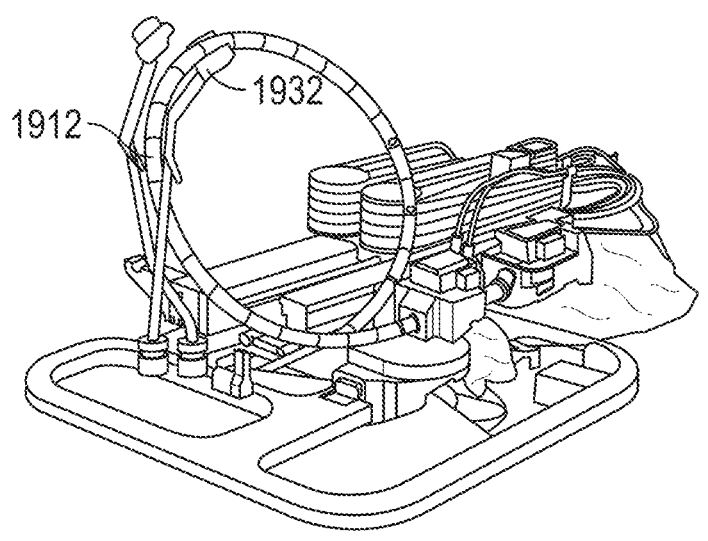

However, in some cases it may be desirable to pre-load the apparatus with the telescoping assembly (e.g., overtube and endoscope) and then move it into position near the patient, so that it may be aligned with the patient. FIG. 19H shows an example in which the apparatus is preloaded on the robotic assembly as just described, and the supports are moved to the pre-deployment configuration by moving the third and fourth supports in an upright configuration and retracting the link assembly into the compact configuration. In this example the telescoping assembly may held by one or more hooks or other regions on the supports to until the cart including the apparatus can be positioned near the patient and used to control operation of the apparatus.

When loading the apparatus, the user may decide how far to retract the system. For example, in some cases the fourth support does not need to be lowered into position, and only the third support arm is lowered for loading. This may depend on the size of the room being used.

Figure 20A:
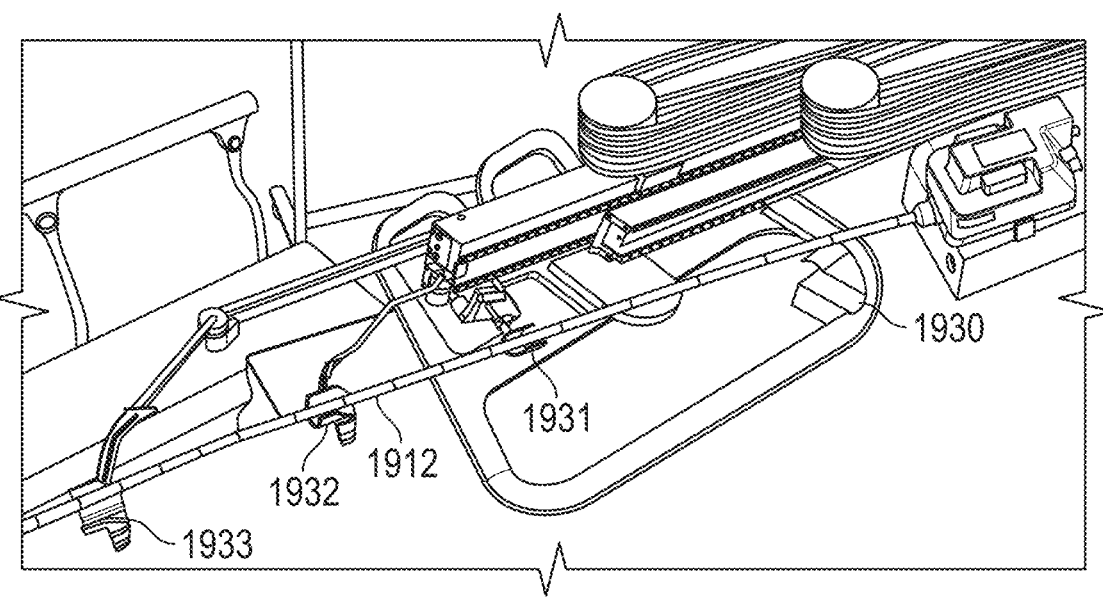
FIGS. 20A-20I illustrate operation of the supports as the nested telescoping apparatus is inserted and/or withdrawn.

FIGS. 20A-20I illustrate the operation of the apparatus of FIGS. 19A-19H after installing the overtube and endoscope. FIG. 20A shows the apparatus ready for the patient (e.g., on a gurney) so that the apparatus can be aligned with the patient. The apparatus may be positioned closed to the gurney and patient, initially with the overtube/endoscope in the staged pre-deployed configuration shown in FIG. 19H. Once the patient is in position, the device may be inserted into the patient and operated to robotically (or optionally manually) advance and retracted, including steered.

Figure 20B:
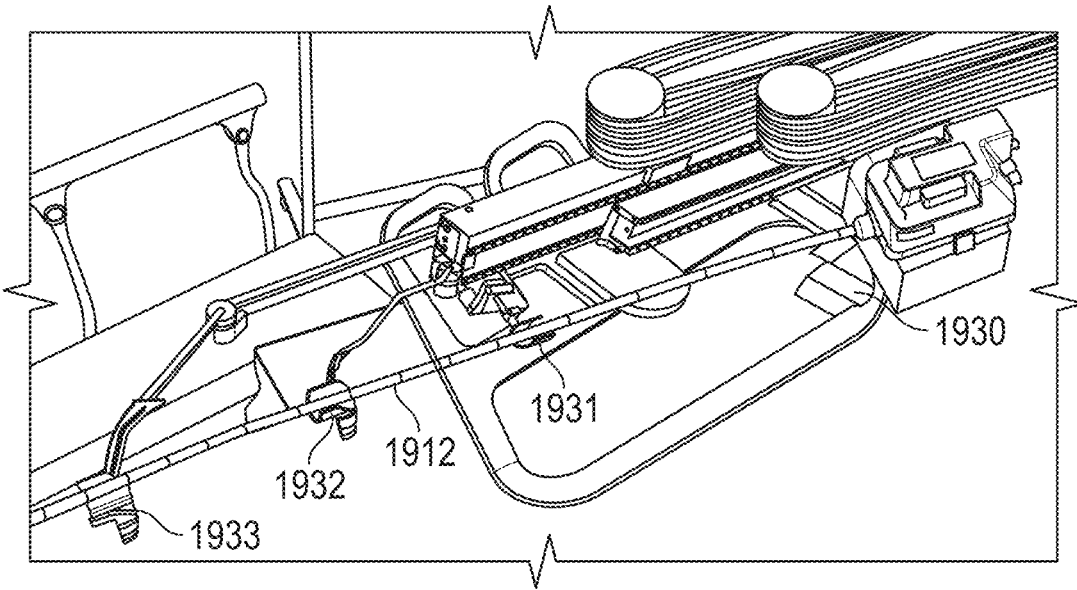
Figure 20C:
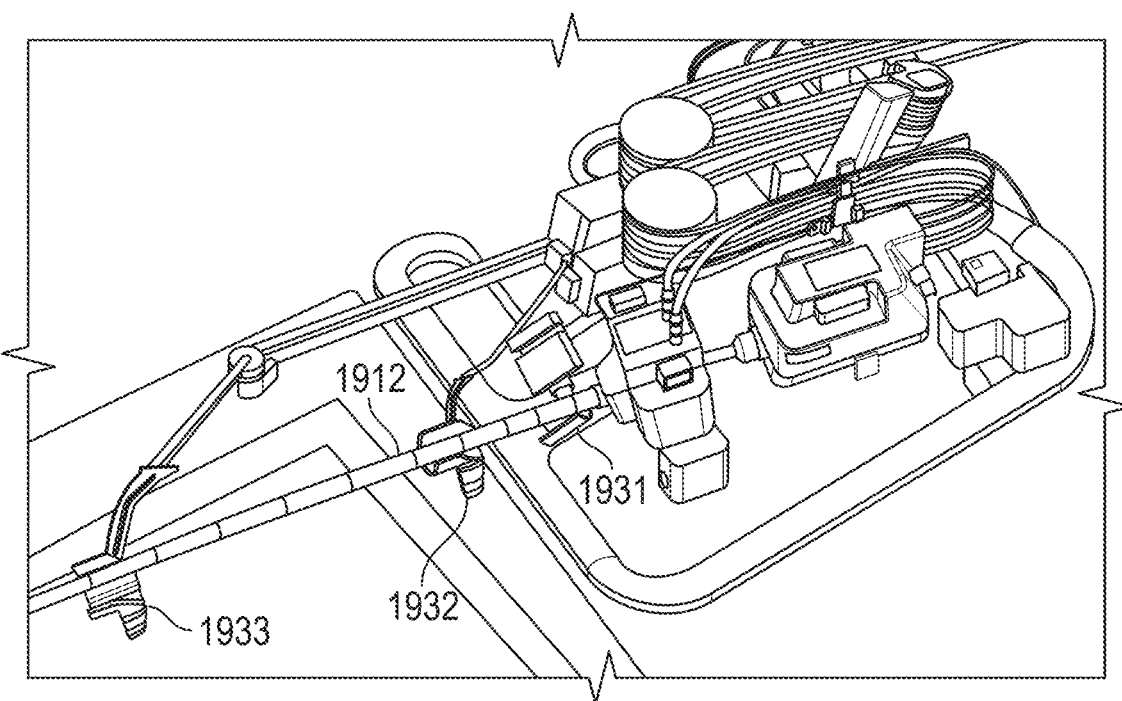
Figure 20D:
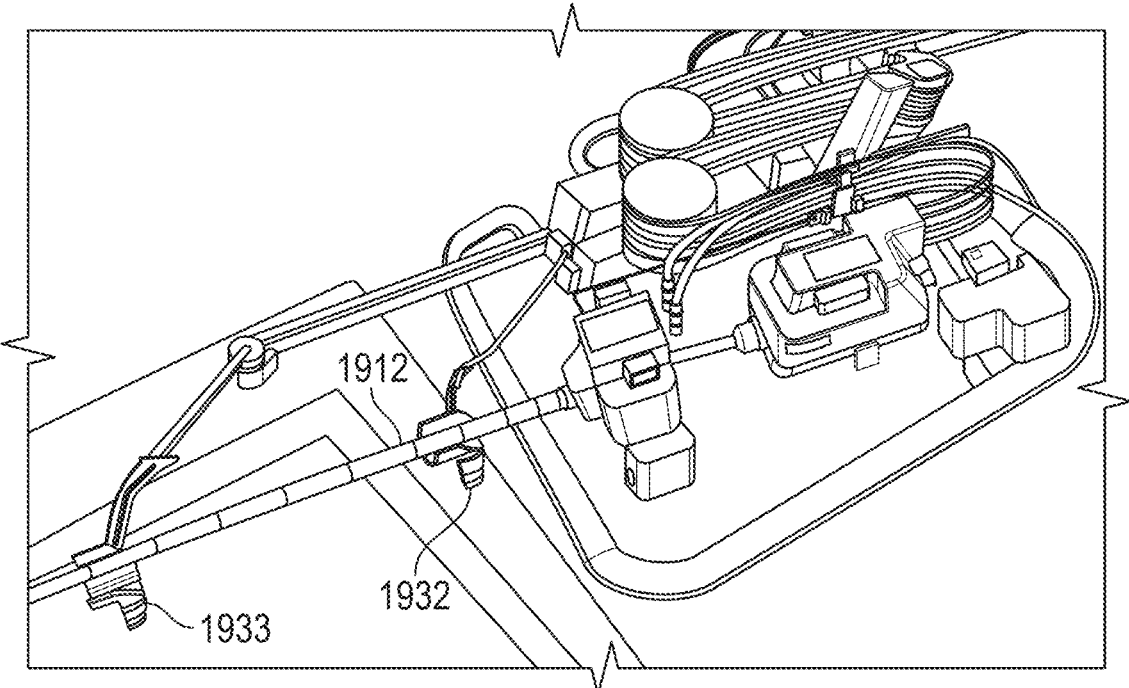
Figure 20E:
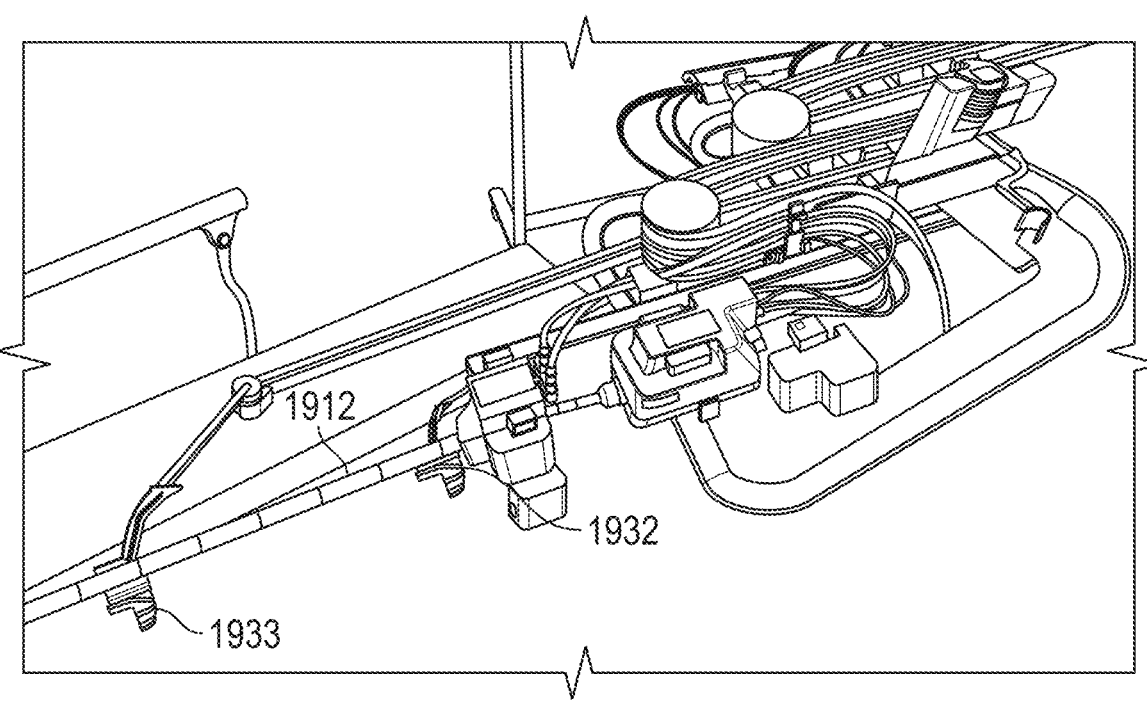
Figure 20F:
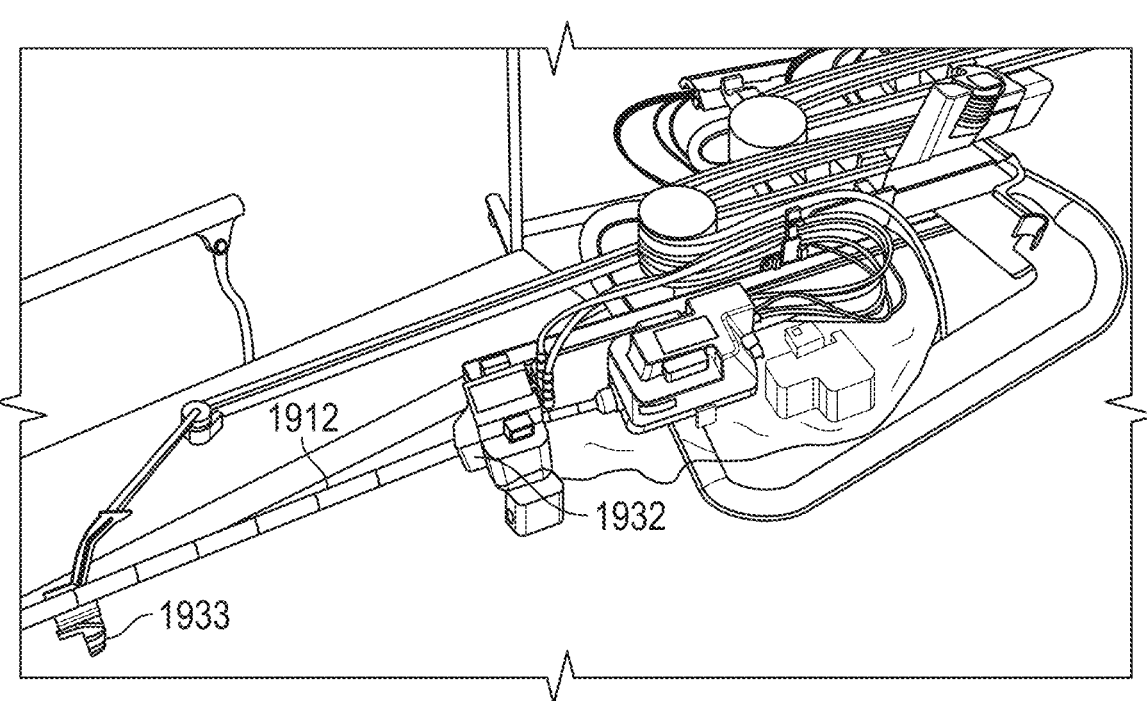

As described below, in any of these methods and apparatuses, the apparatus may be aligned using a targeting component (e.g., laser) integrated with the apparatus, e.g., in line with the insertion axis for the apparatus. In FIGS. 20B-20C the apparatus is inserted into the patient and may be advanced (both the overtube and endoscope) by moving the links of the link assembly from a proximally retracted position (shown in FIG. 20) to a more distal position as shown. As the links are moved proximally the elongate body of the overtube 1912 (and endoscope within the overtube) slides distally within the support seating regions. In FIG. 20A-20B the first support 1930 is deflected down and away from the link assembly as it is advanced distally. Similarly as the link assembly is advanced further distally, in FIGS. 20C-20D, the second support 1931 is deflected down and away from the link assembly. Further advancing the link assembly, and therefore the overtube/endoscope (telescoping apparatus) distally causes the third support 1932 to be deflected down, as shown in FIG. 20E and then laterally, as shown in FIG. 20F, so that the support does not interfere with the advancement of the link assembly and the telescoping apparatus.

Figure 20G:
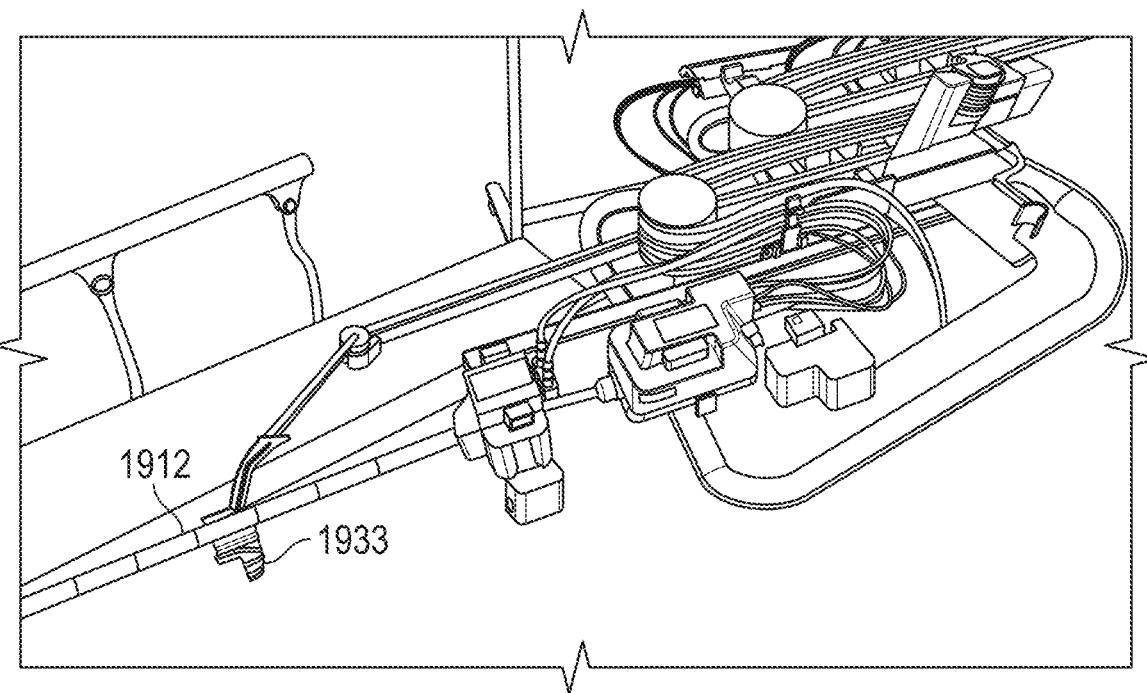
Figure 20H:
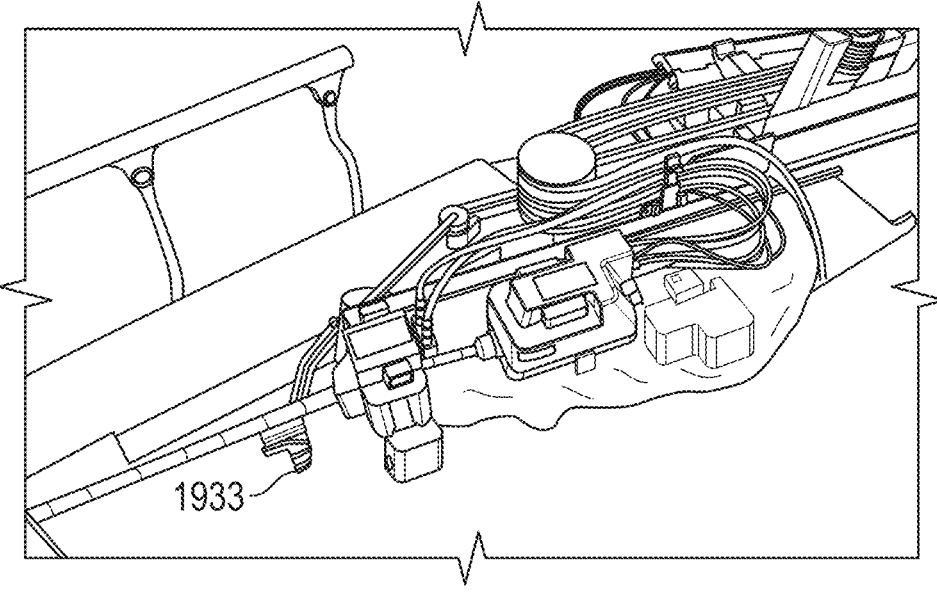
Figure 20I:
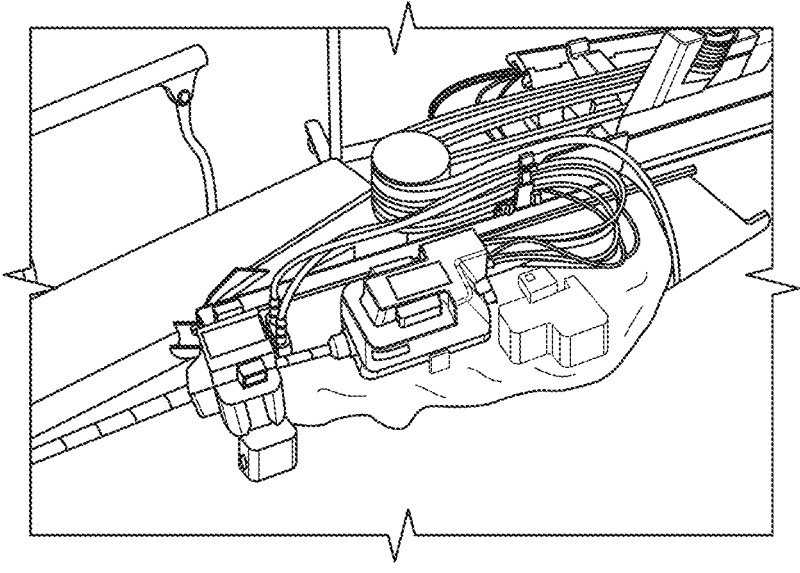

FIG. 20G shows the link assembly extending the overtube/endoscope further distally, until it approaches the fourth support 1933, as shown in FIGS. 20H and 20I, causing the fourth support to be driven down slightly, without contacting the table/bed, and then deflecting laterally, as shown in FIG. 20I. The same steps may be repeated in reverse as the apparatus is withdrawn proximally, allowing the fourth support to be moved laterally back and rotated back up so that the support seating region is in-line with the insertion/withdrawal axis of the overtube/endoscope, followed by the third support moving laterally back and rotated back up so that the support seating region is in-line with the insertion/withdrawal axis of the overtube/endoscope, then the second support rotating back up so that the support seating region is in-line with the insertion/withdrawal axis of the overtube/endoscope, and the first support rotating back up so that the support seating region is in-line with the insertion/withdrawal axis of the overtube/endoscope. This process may be performed robotically, by one or more drives driving the link assembly as described above, and/or during a manual or manual override procedure. At any point during the insertion and/or withdrawal, the endoscope may be moved separately from the overtube (and vice versal) by moving the respective mounts.

Figure 21A:
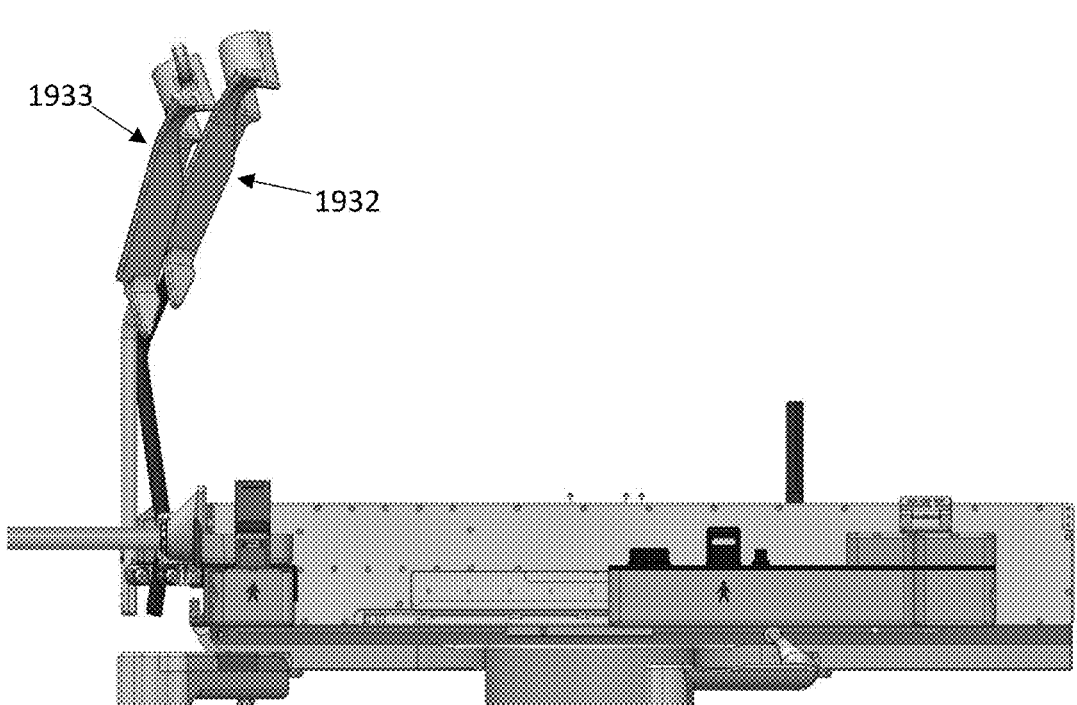
FIGS. 21A and 21B show side and front views, respectively, of a portion of an apparatus, including a link assembly with supports, as described herein. In this configuration of the link assembly and supports, two of the supports are shown in a stored configuration, folded out of the plane of the insertion axis.
Figure 21B:
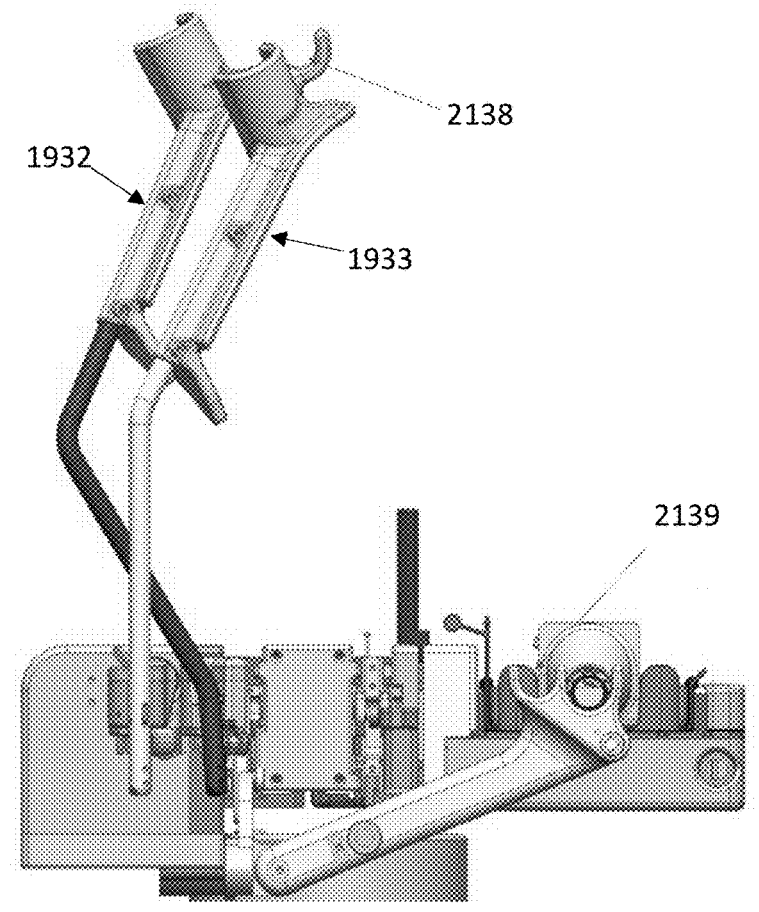

As mentioned, any of these apparatuses may include a pre-deployment configuration in which one or more of the supports are moved out of the plane of movement of the link assembly. For example, FIGS. 21A and 21B show top and front views, respectively, of an apparatus including a link assembly having four supports, including supports (e.g., the third 1932 and fourth 1933 supports) that are configured to be folded up in the pre-deployment configuration. In the pre-deployed configuration the third and/or fourth support 1932, 1933 includes a hook or other attachment 2138 that is configured to hold the looped over telescoping apparatus (e.g., overtube/endoscope) in the staged, pre-deployed configuration. FIG. 21B shows a hook 2138 on the fourth support but it may optionally be on the third. In addition, the second support 1931 also includes an attachment 2139, shown as an adjacent seating region, for holding the telescoping apparatus (which may be referred to as a staged device tip pocket). The pre-deployment configuration with staging of the telescoping apparatus is shown in FIG. 19H, for example, and in FIG. 22.

Figure 22:
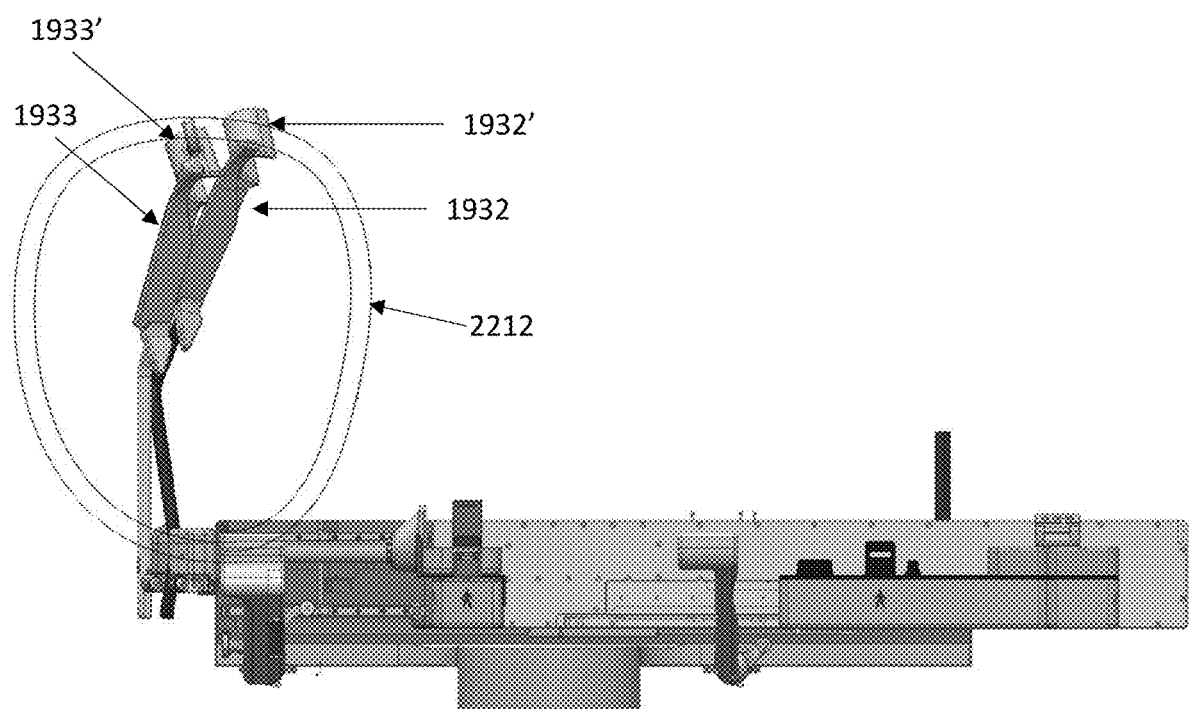
FIG. 22 shows another view (e.g., side view) of an apparatus similar to that shown in FIGS. 21A-21B, including a nested telescoping apparatus shown schematically illustrated in a pre-loaded configuration ready to be positioned and deployed relative to a patient.

In FIG. 22, the telescoping apparatus 2212 is shown with the telescoping assembly in the pre-loaded and stored configuration, ready to be deployed. As described above, this maintains the telescoping assembly ready for deployment so that the entire apparatus, including the link assembly and overtube/endoscope can be positioned adjacent to patient for deployment. Once positioned, the supports 1932, 1933 can be moved down from the stored position shown in FIG. 22 so that the seating regions 1932', 1933' are in-line with the insertion/withdrawal axis.

Figure 23:
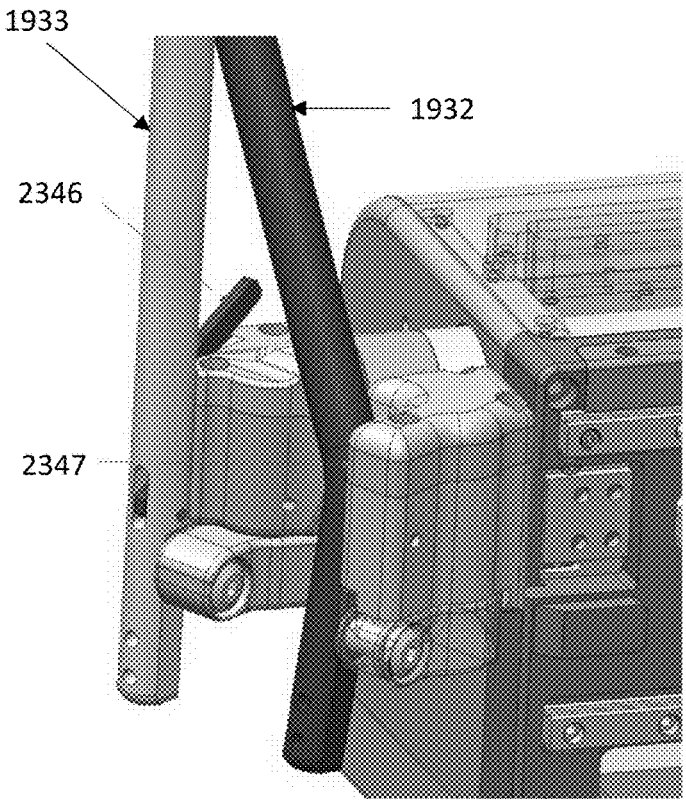
FIG. 23 is an enlarged view of the connection region of two of the supports of the apparatus showing connection to the link assembly.

FIG. 22 is a rear view that shows the attachment between the supports and the first link of the link assembly; the fourth support 1933 is connected to an extendable arm that extends from the first link. In the stored configuration shown in FIGS. 22 and 23, this extendable arm is retraced into the link assembly and is not visible. The connection for the fourth support 1933 and/or the third support 1932 may include a latch (e.g., support release latch) 2346. In some cases the attachment, e.g., for the third support, may be retained by a bias or other mechanical and/or electrical/magnetic retainer to prevent accidental deployment. For example, in FIG. 23, the attachment for the third support to the link assembly includes a spring ball detent 2347 preventing accidental deployment; to deploy the support, the user may apply force to overcome the detent and rotate the support so that the seating region is in-line with the deployment axis.

Any of the apparatuses described herein may include a targeting guide to assist in aligning the insertion axis of the robot with the patient, e.g., with the insertion region on the patient (e.g., the patient's anus/rectum). For example, any of these apparatuses may include an optical sight (e.g., laser sight, LED sight, etc.) configured for targeting on the link assembly, e.g., on the inner/third link, on one of the supports, on the mount (e.g., endoscope mount, overtube mount, etc.). In some cases the optical sight is a low-power (e.g., class I) visible light laser (e.g., red light, blue light, white light, etc.) that projects a beam of light indicating where the insertion axis from the apparatus will contact the patient. The optical sight may be configured to be moved into the insertion axis and/or out of the insertion axis. When setting up the apparatus, e.g., from a pre-deployed configuration, the optical sight may be moved into (or may be automatically in) position relative to the insertion axis. In some cases this may displace the pre-loaded telescoping assembly of the overtube/endoscope. In some cases the optical sight may be used prior to coupling the telescoping overtube/endoscope.

Figure 24:
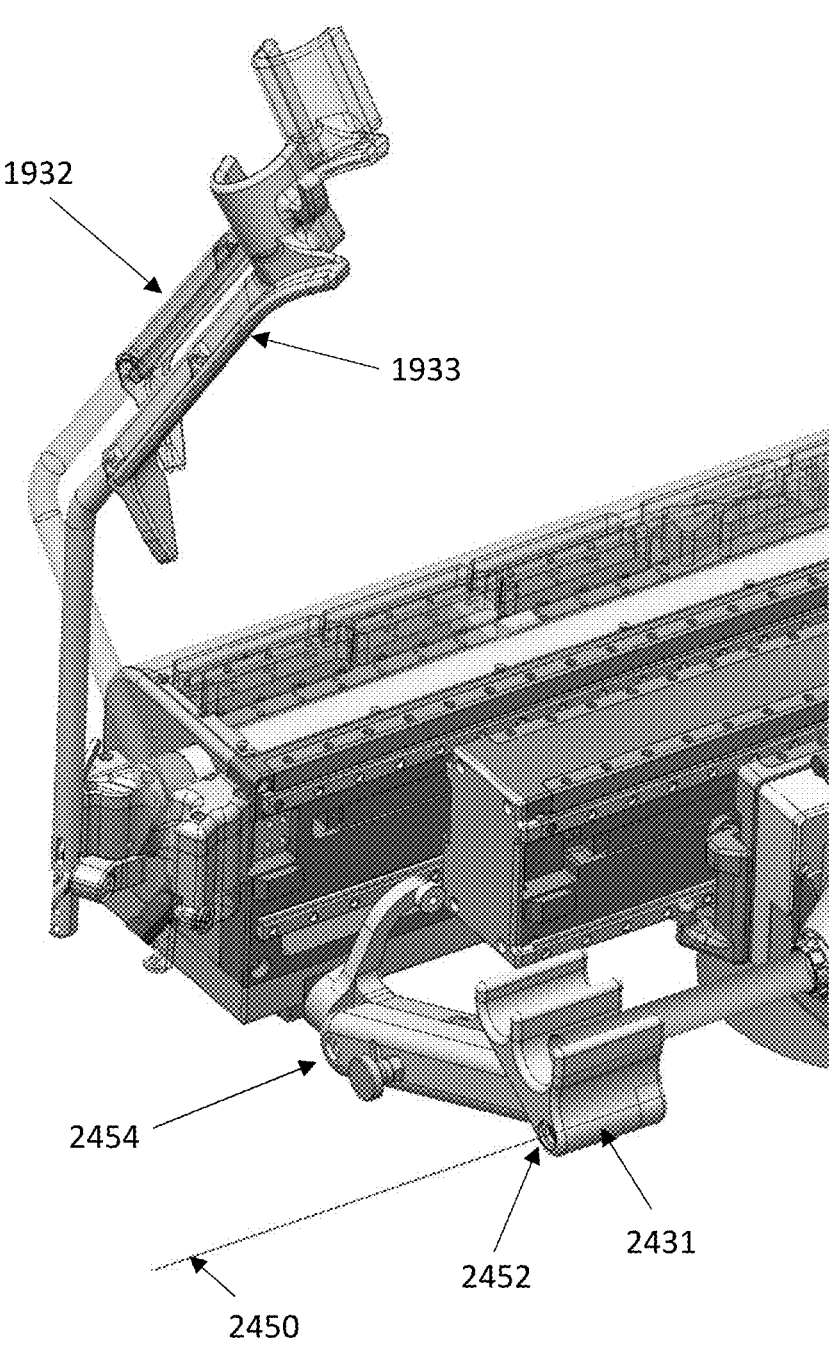
FIG. 24 schematically illustrates an example of an optical sight (sighting device) that may be incorporated into any of the apparatuses described herein to assist in aligning the insertion axis of the apparatus with the patient.

FIG. 24 illustrates one example of an apparatus including an optical sight 2452 that is, in this example, coupled to the second support 2431. The second support is configured so that it may be manually or automatically moved, e.g., pivoted, so that the overtube/endoscope is displaced and the optical sight is moved into the insertion axis. For example, the second support may include a pivot 2454 that allows second support to move the seating region holding the pre-loaded telescoping apparatus (e.g., the overtube/endoscope) into or out of the insertion axis, so that the light 2450 (e.g., laser) is emitted as a beam that will indicate the location of contact with the insertion axis, e.g., on the patient's body. For example, the optical sight may be moved into position and used to align the apparatus. In some cases the projected light may be projected as an image, e.g., of crosshairs. The apparatus may be configured to manually or automatically (or semi-automatically) confirm the targeting to the entry point of the patient. The base of the apparatus, which may be moveable, may be locked in position once targeting is confirmed, and the optical sight (e.g., laser) may be turned off and moved out of the way of the insertion axis so that it does not interfere with the overtube/endoscope.

In some cases the apparatus (e.g., the optical sight) may be configured to provide range data, and the system may confirm the distance to the patient is sufficient or insufficient (e.g., and that the apparatus should be moved closer/farther from the patient).

At the end of a procedure, the nested telescoping apparatus (e.g., overtube/endoscope) may be removed, and the supports may be wiped down with the rest of the system, and the supports (e.g., the third and fourth support arms may be stowed vertically, as described above).

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like. For example, any of the methods described herein may be performed, at least in part, by an apparatus including one or more processors having a memory storing a non-transitory computer-readable storage medium storing a set of instructions for the processes(s) of the method.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An apparatus for deploying a flexible tubular member, the apparatus comprising:

a base;

a bidirectional telescoping link assembly connected to the base and comprising: a plurality of links that are adjacent to each other, wherein adjacent pairs of links are configured to move in a coordinated manner so that the plurality of links extend proximally from a compact neutral configuration to a proximal extended configuration and extend distally from the compact neutral configuration to a distal extended configuration, wherein the compact neutral configuration has a length that less than a length of the proximal extended configuration and less a length of the distal extended configuration;

a driver configured to drive movement of the links of the telescoping link assembly; and a mount assembly coupled to the link assembly, wherein the mount assembly is configured to couple to the flexible tubular member and further wherein the mount assembly comprises a mounting surface and one or more actuators configured to steer the flexible tubular member.

2. The apparatus of claim 1, wherein the plurality of links are vertically adjacent to each other.

3. The apparatus of claim 1, further comprising one or more synchronizing members coupled to each link of the plurality of links configured to coordinate movement of all of the links when force is applied to one of the links.

4. The apparatus of claim 1, wherein the mount assembly comprises an overtube mount and an endoscope mount, wherein the endoscope mount is configured to move proximally and/or distally relative to the overtube mount.

5. The apparatus of claim 1, wherein the link assembly is configured to extend from the compact configuration to a length of 1 m or longer.

6. The apparatus of claim 1, wherein a vertical distance from the mount assembly to lowermost surface of the link assembly is less than 20 cm.

7. The apparatus of claim 1, wherein the plurality of links are configured so that adjacent pairs of links are each slidably coupled together by a ball screw nut assembly.

8. The apparatus of claim 1, wherein the plurality of links are configured so that adjacent pairs of links are each slidably coupled together by a pair of opposing flexible bands that extend around one or more surfaces of shuttle in opposite directions.

9. The apparatus of claim 8, further comprising pairs of shuttles between adjacent links of adjacent pairs of links that are coupled together on a synchronization belt.

10. A method of deploying an endoscope nested with an overtube, the method comprising:

advancing and/or retracting the overtube together with the endoscope by moving one or more links of a bidirectional telescoping link assembly, wherein the overtube is coupled to an overtube mount on a first link of the bidirectional telescoping link assembly and wherein the endoscope is coupled to an endoscope mount on the first link, and wherein the bidirectional link assembly comprises a plurality of links, wherein the plurality of links are adjacent to each other, and wherein advancing the overtube comprises extending the one or more links of the bidirectional telescoping link assembly distally from a compact neutral configuration to a distally extended configuration and wherein retracting the overtube comprises retracting one or more links of the bidirectional telescoping link assembly proximally from the compact neutral configuration to a proximally extended configuration; and moving the endoscope into or out of the overtube by changing the relative positions of the endoscope mount and the overtube mount on the first link.

11. The method of claim 10, wherein extending the plurality of links comprises using a driver to drive movement of the links of the telescoping link assembly.

12. The method of claim 10, further comprising coupling the overtube to the overtube mount.

13. The method of claim 10, further comprising coupling the endoscope nested within the overtube to the endoscope mount.

14. A method of deploying an endoscope nested with an overtube, the method comprising:

advancing and/or retracting the overtube together with the endoscope by moving a first link of a bidirectional telescoping link assembly, wherein the overtube is coupled to an overtube mount on the first link and wherein the endoscope is coupled to an endoscope mount on the first link, and wherein the bidirectional link assembly comprises a plurality of links, including the first link, that are slidably coupled together and are adjacent to each other, and wherein advancing the overtube comprises extending one or more of the plurality of links distally from a compact neutral configuration to a distally extended configuration, and wherein retracting the overtube comprises retracting one of or more of the plurality of links proximally from the compact neutral configuration to a proximally extended configuration; and moving the endoscope into or out of the overtube by changing the relative positions of the endoscope mount and the overtube mount on the first link.

15. The method of claim 14, wherein advancing and/or retracting comprises extending or retracting the one or more links of the plurality of links using a driver to drive movement of the links of the telescoping link assembly.

16. The method of claim 14, further comprising coupling the overtube to the overtube mount.

17. The method of claim 14, further comprising coupling the endoscope nested within the overtube to the endoscope mount.

18. An apparatus, the apparatus comprising:

a telescoping link assembly comprising: a plurality of vertical links that are adjacent to each other, wherein the plurality of vertical links comprises one or more adjacent pairs of vertical links and wherein each vertical link of adjacent pairs of vertical links are each configured to move relative to each other and relative to a base link;

a first mount coupled to a first link of the plurality of vertical links of the telescoping link assembly, wherein the first mount is configured to engage an overtube; and a second mount coupled to the first link and configured to engage an endoscope nested with the overtube, wherein the overtube and endoscope are configured to be moved axially by distally advancing or proximally retracting one or more of the vertical links of the telescoping link assembly relative to the base link.

19. The apparatus of claim 18, further comprising a plurality of supports movably coupled to the telescoping link assembly, wherein each support of the plurality of supports comprises a seating region configured to hold the overtube and endoscope in-line with a distal-to-proximal line extending from the telescoping link assembly.

20. The apparatus of claim 19, wherein each support of the plurality of supports are configured to be deflected so that the seating region of each support is moved out of the distal-to-proximal line as the plurality of the links of the telescoping link assembly are extended distally.

21. The apparatus of claim 19, wherein at least one of the supports of the plurality of supports is configured to be deflected down and laterally as the plurality of the links of the telescoping link assembly are extended distally.

22. The apparatus of claim 18, further comprising a driver configured to drive movement of the vertical links of the telescoping link assembly.

23. The apparatus of claim 19, wherein at least one of the supports of the plurality of supports are configured to move from a deployed configuration in which the seating regions of the supports are configured to hold the overtube and endoscope in-line with the distal-to-proximal line, to a pre-deployed configuration in which the supports are raised vertically out of a plane of the distal-to-proximal line.

24. The apparatus of claim 19, wherein at least one of the supports of the plurality of supports is coupled to an extender on the link assembly that is configured to extend distally from the link assembly.

25. The apparatus of claim 18, wherein the first and/or second mount are configured to move relative to each other on the first link to adjust the relative positions of the endoscope and the overtube.

\* \* \* \* \*